(12) United States Patent
Hale et al.

(10) Patent No.: US 12,037,380 B2
(45) Date of Patent: Jul. 16, 2024

(54) MODIFIED IMMUNOGLOBULIN Fc REGIONS

(71) Applicant: Mabsolve Limited, Oxford (GB)

(72) Inventors: Geoffrey Hale, Oxford (GB); Ian Wilkinson, Oxford (GB)

(73) Assignee: MABSOLVE LIMITED, Oxford (GB)

( * ) Notice: Subject to any disclaimer, the term of this patent is extended or adjusted under 35 U.S.C. 154(b) by 0 days.

(21) Appl. No.: 18/057,420

(22) Filed: Nov. 21, 2022

(65) Prior Publication Data

US 2023/0235013 A1 Jul. 27, 2023

Related U.S. Application Data

(63) Continuation of application No. PCT/GB2021/051233, filed on May 20, 2021.

(30) Foreign Application Priority Data

May 21, 2020 (GB) .................................... 2007613

(51) Int. Cl.
| | | |
|---|---|---|
| *C07K 16/00* | (2006.01) | |
| *C07K 19/00* | (2006.01) | |
| *C07K 14/705* | (2006.01) | |
| *C07K 14/735* | (2006.01) | |
| *C12N 15/63* | (2006.01) | |

(52) U.S. Cl.
CPC .............. *C07K 16/00* (2013.01); *C07K 19/00* (2013.01); *C07K 14/70535* (2013.01); *C07K 2317/52* (2013.01); *C07K 2317/71* (2013.01); *C07K 2319/30* (2013.01); *C12N 15/63* (2013.01)

(58) Field of Classification Search
CPC . C07K 16/00; C07K 2317/52; C07K 2319/30
See application file for complete search history.

(56) References Cited

U.S. PATENT DOCUMENTS

| | | |
|---|---|---|
| 5,648,260 A | 7/1997 | Winter et al. |
| 6,194,551 B1 | 2/2001 | Idusogie et al. |
| 6,737,056 B1 | 5/2004 | Presta |
| 7,597,889 B1 | 10/2009 | Armour et al. |
| 7,662,925 B2 | 2/2010 | Lazar et al. |
| 7,960,512 B2 | 6/2011 | Stavenhagen et al. |
| 8,399,618 B2 | 3/2013 | Lazar et al. |
| 8,409,568 B2 | 4/2013 | Gao et al. |
| 8,871,204 B2 | 10/2014 | Brezski et al. |
| 8,883,147 B2 | 11/2014 | Lazar et al. |
| 8,961,967 B2 | 2/2015 | Strohl et al. |
| 8,969,526 B2 | 3/2015 | Baehner et al. |
| 9,040,041 B2 | 5/2015 | Desjarlais et al. |
| 9,718,893 B2 | 8/2017 | Jung et al. |
| 9,771,426 B2 | 9/2017 | Georgiou et al. |
| 9,969,800 B2 | 5/2018 | Igawa et al. |
| 10,011,660 B2 | 7/2018 | Tsui et al. |
| 2006/0235208 A1 | 10/2006 | Lazar et al. |
| 2007/0041966 A1 | 2/2007 | Armour et al. |
| 2007/0219133 A1 | 9/2007 | Lazar et al. |
| 2009/0060906 A1 | 3/2009 | Barry et al. |
| 2011/0059078 A1 | 3/2011 | Coyle et al. |
| 2012/0282254 A1 | 11/2012 | Kirby et al. |
| 2012/0294796 A1 | 11/2012 | Johnson et al. |
| 2014/0105889 A1 | 4/2014 | Igawa et al. |
| 2015/0071948 A1 | 3/2015 | Lazar et al. |
| 2015/0232567 A1 | 8/2015 | Lazar et al. |
| 2015/0337053 A1 | 11/2015 | McCarthy et al. |
| 2016/0229908 A1 | 8/2016 | Igawa et al. |
| 2016/0297886 A1 | 10/2016 | Georgiou et al. |
| 2017/0029521 A1 | 2/2017 | Van De Winkel et al. |
| 2017/0073421 A1 | 3/2017 | Kjaergaard et al. |
| 2018/0360981 A1* | 12/2018 | Lazar ................. C07K 16/2887 |
| 2019/0100587 A1 | 4/2019 | Brack et al. |
| 2019/0352421 A1 | 11/2019 | Adams et al. |
| 2023/0235073 A1* | 7/2023 | Aznar Benitah .. C07K 16/2896 424/133.1 |

FOREIGN PATENT DOCUMENTS

| | | |
|---|---|---|
| EP | 0307434 A1 | 3/1989 |
| EP | 1423431 A2 | 6/2004 |
| EP | 1873166 A1 | 1/2008 |
| EP | 1931709 A2 | 6/2008 |
| EP | 2486141 A1 | 8/2012 |
| EP | 2647707 A1 | 10/2013 |
| EP | 2691417 A1 | 2/2014 |
| EP | 2794658 A1 | 10/2014 |

(Continued)

OTHER PUBLICATIONS

Alegre et al., "Effect of a single amino acid mutation on the activating and immunosuppressive properties of a "humanized" OKT3 monoclonal antibody," J Immunol. 1992;148(11):3461-8.

Angal et al., "A single amino acid substitution abolishes the heterogeneity of chimeric mouse/human (IgG4) antibody," Mol Immunol. Jan. 1993;30(1):105-8.

Armour et al., "Recombinant human IgG molecules lacking Fcgamma receptor I binding and monocyte triggering activities," Eur J Immunol. Aug. 1999;29(8):2613-24.

Bajaj et al., "Stability Testing of Pharmaceutical Products," J Appl Pharm Sci. Mar. 2012;2(3):129-38.

Beck and Reichert, "Therapeutic Fc-fusion proteins and peptides as successful alternatives to antibodies," MAbs. Sep.-Oct. 2011;3(5):415-6.

Boesch et al., "Highly parallel characterization of IgG Fc binding interactions," MAbs. Jul.-Aug. 2014;6(4):915-27.

(Continued)

*Primary Examiner* — Zachary C Howard

(74) *Attorney, Agent, or Firm* — Dechert LLP; Andrew T. Wilkins

(57) ABSTRACT

Provided are proteins comprising a variant IgG Fc region, wherein the proteins exhibit significantly reduced binding to human FcγRI when compared with a reference protein comprising the amino acid substitutions L234A/L235A/P329G. Also provided are compositions, methods of treatment and methods to reduce Fc-induced effector functions in a parent protein.

28 Claims, 12 Drawing Sheets

Specification includes a Sequence Listing.

(56) References Cited

FOREIGN PATENT DOCUMENTS

| | | |
|---|---|---|
| WO | WO-1988007089 A1 | 9/1988 |
| WO | WO-1994028027 A1 | 12/1994 |
| WO | WO-1999058572 A1 | 11/1999 |
| WO | WO-2000042072 A2 | 7/2000 |
| WO | WO-2006033386 A1 | 3/2006 |
| WO | WO-2006047350 A2 | 5/2006 |
| WO | WO-2006053301 A2 | 5/2006 |
| WO | WO-2006076594 A2 | 7/2006 |
| WO | WO-2006105338 A2 | 10/2006 |
| WO | WO-2008092117 A2 | 7/2008 |
| WO | WO-2008145142 A1 | 12/2008 |
| WO | WO-2009100309 A2 | 8/2009 |
| WO | WO-2010063785 A2 | 6/2010 |
| WO | WO-2011066501 A1 | 6/2011 |
| WO | WO-2012022982 A2 | 2/2012 |
| WO | WO-2012130831 A1 | 10/2012 |
| WO | WO-2012168199 A1 | 12/2012 |
| WO | WO-2013165690 A1 | 11/2013 |
| WO | WO-2013186719 A1 | 12/2013 |
| WO | 2014020056 A1 | 2/2014 |
| WO | WO-2014108483 A1 | 7/2014 |
| WO | WO-2015132364 A1 * | 9/2015 ........... A61K 39/395 |
| WO | WO-2016207858 A1 | 12/2016 |
| WO | WO-2017019565 A2 | 2/2017 |
| WO | WO-2017040380 A2 | 3/2017 |
| WO | WO-2017046994 A1 | 3/2017 |
| WO | WO-2017079369 A2 | 5/2017 |
| WO | WO-2018044948 A1 | 3/2018 |
| WO | WO-2018089300 A1 | 5/2018 |
| WO | WO-2018187799 A1 | 10/2018 |
| WO | WO-2018200422 A1 | 11/2018 |
| WO | 2019211472 A1 | 11/2019 |
| WO | 2020052692 A2 | 3/2020 |
| WO | WO-2020086776 A1 | 4/2020 |
| WO | WO-2021176424 A1 | 9/2021 |

OTHER PUBLICATIONS

Bolt et al., "The generation of a humanized, non-mitogenic CD3 monoclonal antibody which retains in vitro immunosuppressive properties," Eur J Immunol. Feb. 1993;23(2):403-11.

Borrok et al., "An "Fc-Silenced" IgG1 Format With Extended Half-Life Designed for Improved Stability," J Pharm Sci. Apr. 2017;106(4):1008-1017.

Brinkmann and Kontermann, "The making of bispecific antibodies," MAbs. Feb./Mar. 2017;9(2):182-212.

Brinks et al., "Preclinical models used for immunogenicity prediction of therapeutic proteins," Pharm Res. Jul. 2013;30(7):1719-28.

Bruhns et al., "Specificity and affinity of human Fcgamma receptors and their polymorphic variants for human IgG subclasses," Blood. Apr. 16, 2009;113(16):3716-25.

Bryson et al., "Prediction of immunogenicity of therapeutic proteins: validity of computational tools," BioDrugs. Feb. 1, 2010;24(1):1-8.

Chen et al., "Immunogenicity of the outer domain of a HIV-1 clade C gp120," Retrovirology. May 17, 2007;4:33.

Choi et al., "A heterodimeric Fc-based bispecific antibody simultaneously targeting VEGFR-2 and Met exhibits potent antitumor activity," Mol Cancer Ther. Dec. 2013;12(12):2748-59.

Choi et al., "Crystal structures of immunoglobulin Fc heterodimers reveal the molecular basis for heterodimer formation," Mol Immunol. Jun. 2015;65(2):377-83.

Choi et al., "Engineering of Immunoglobulin Fc Heterodimers Using Yeast Surface-Displayed Combinatorial Fc Library Screening," PLoS One. Dec. 16, 2015;10(12):e0145349.

Combined Search and Examination Report from GB2007613.9 dated Jan. 13, 2021.

Costa et al., "Glycosylation: impact, control and improvement during therapeutic protein production," Crit Rev Biotechnol. Dec. 2014;34(4):281-99.

Dall'Acqua et al., "Modulation of the effector functions of a human IgG1 through engineering of its hinge region," J Immunol. Jul. 15, 2006;177(2):1129-38.

Datta-Mannan and Wroblewski, "Application of FcRn binding assays to guide mAb development," Drug Metab Dispos. Nov. 2014;42(11):1867-72.

De Jong et al., "A Novel Platform for the Potentiation of Therapeutic Antibodies Based on Antigen-Dependent Formation of IgG Hexamers at the Cell Surface," PLoS Biol. Jan. 6, 2016;14(1):e1002344.

De Nardis et al., "A new approach for generating bispecific antibodies based on a common light chain format and the stable architecture of human immunoglobulin G1," J Biol Chem. Sep. 1, 2017;292(35):14706-14717.

Den Engelsman et al., "Strategies for the assessment of protein aggregates in pharmaceutical biotech product development," Pharm Res. Apr. 2011;28(4):920-33.

Deng et al., "Pharmacokinetics of humanized monoclonal antitumor necrosis factor-{alpha} antibody and its neonatal Fc receptor variants in mice and cynomolgus monkeys," Drug Metab Dispos. Apr. 2010;38(4):600-5.

Dhanda et al., "IEDB-AR: immune epitope database-analysis resource in 2019," Nucleic Acids Res. Jul. 2, 2019;47(W1):W502-W506.

Dumet et al., "Insights into the IgG heavy chain engineering patent landscape as applied to IgG4 antibody development," MAbs. 2019;11(8):1341-1350.

Edelman et al., "The covalent structure of an entire gammaG immunoglobulin molecule," Proc Natl Acad Sci U S A. May 1969;63(1):78-85.

Examination Report from CA3179582 dated Feb. 10, 2023.

Fan et al., "A novel therapeutic strategy to rescue the immune effector function of proteolytically inactivated cancer therapeutic antibodies," Mol Cancer Ther. Mar. 2015;14(3):681-91.

Finco et al., "Cytokine release assays: current practices and future directions," Cytokine. Apr. 2014;66(2):143-55.

Findlay et al., "Endothelial cells co-stimulate peripheral blood mononuclear cell responses to monoclonal antibody TGN1412 in culture," Cytokine. Jul. 2011;55(1):141-51.

Findlay et al., "Improved in vitro methods to predict the in vivo toxicity in man of therapeutic monoclonal antibodies including TGN1412," J Immunol Methods. Jan. 31, 2010;352(1-2):1-12.

First Examination Report from AU 2021277578 dated Dec. 22, 2022.

Fleri et al., "The Immune Epitope Database and Analysis Resource in Epitope Discovery and Synthetic Vaccine Design," Front Immunol. Mar. 14, 2017;8:278.

Greenbaum et al., "Functional classification of class II human leukocyte antigen (HLA) molecules reveals seven different supertypes and a surprising degree of repertoire sharing across supertypes," Immunogenetics. Jun. 2011;63(6):325-35.

Greenwood et al., "Structural motifs involved in human IgG antibody effector functions," Eur J Immunol. 1993;23(5):1098-104.

Gregorio et al., "A User's Guide to Cell-Free Protein Synthesis," Methods Protoc. Mar. 12, 2019;2(1):24.

Grimaldi et al., "Cytokine release: A workshop proceedings on the state-of-the-science, current challenges and future directions," Cytokine. Sep. 2016;85:101-8.

Gunasekaran et al., "Enhancing antibody Fc heterodimer formation through electrostatic steering effects: applications to bispecific molecules and monovalent IgG," J Biol Chem. Jun. 18, 2010;285(25):19637-46.

Hale et al., "Removal of T cells from bone marrow for transplantation: a monoclonal antilymphocyte antibody that fixes human complement," Blood. Oct. 1983;62(4):873-82.

Hezareh et al., "Effector function activities of a panel of mutants of a broadly neutralizing antibody against human immunodeficiency virus type 1," J Virol. Dec. 2001;75(24):12161-8.

Hinton et al., "Engineered human IgG antibodies with longer serum half-lives in primates," J Biol Chem. Feb. 20, 2004;279(8):6213-6.

Horton et al., "Antibody-mediated coengagement of Fc?RIIb and B cell receptor complex suppresses humoral immunity in systemic lupus erythematosus," J Immunol. Apr. 1, 2011;186(7):4223-33.

(56) References Cited

OTHER PUBLICATIONS

Horton et al., "Potent in vitro and in vivo activity of an Fc-engineered anti-CD19 monoclonal antibody against lymphoma and leukemia," Cancer Res. 2008;68(19):8049-57.
Hsiao et al., "Proteolytic single hinge cleavage of pertuzumab impairs its Fc effector function and antitumor activity in vitro and in vivo," Breast Cancer Res. 2018;20(43).
Idusogle et al., "Mapping of the C1q binding site on rituxan, a chimeric antibody with a human IgG1 Fc," J Immunol. Apr. 15, 2000;164(8):4178-84.
International Preliminary Report on Patenability from PCT/GB/2021/051233 dated Aug. 24, 2022.
Ishino et al., "Engineering a monomeric Fc domain modality by N-glycosylation for the half-life extension of biotherapeutics," J Biol Chem. Jun. 7, 2013;288(23):16529-16537.
Jafari et al., "Fc-fusion Proteins in Therapy: An Updated View," Curr Med Chem. 2017;24(12):1228-1237.
Jawa et al., "T-cell dependent immunogenicity of protein therapeutics: Preclinical assessment and mitigation," Clin Immunol. Dec. 2013;149(3):534-55.
Jefferis, "Glycosylation of recombinant antibody therapeutics," Biotechnol Prog. Jan.-Feb. 2005;21(1):11-6.
Jensen et al., "Improved methods for predicting peptide binding affinity to MHC class II molecules," Immunology. Jul. 2018;154(3):394-406.
Joubert et al., "Use of In Vitro Assays to Assess Immunogenicity Risk of Antibody-Based Biotherapeutics," PLoS One. Aug. 5, 2016;11(8):e0159328.
Kanda et al., "Comparison of biological activity among nonfucosylated therapeutic IgG1 antibodies with three different N-linked Fc oligosaccharides: the high-mannose, hybrid, and complex types," Glycobiology. Jan. 2007;17(1):104-18.
Kim et al., "Mapping the site on human IgG for binding of the MHC class I-related receptor, FcRn," Eur J Immunol. Sep. 1999;29(9):2819-25.
King et al., "Removing T-cell epitopes with computational protein design," Proc Natl Acad Sci U S A. Jun. 10, 2014;111(23):8577-82.
Kuo and Aveson, "Neonatal Fc receptor and IgG-based therapeutics," MAbs. Sep.-Oct. 2011;3(5):422-30.
Labrijn et al., "Efficient generation of stable bispecific IgG1 by controlled Fab-arm exchange," Proc Natl Acad Sci U S A. Mar. 26, 2013;110(13):5145-50.
Lazar et al., "Engineered antibody Fc variants with enhanced effector function," Proc Natl Acad Sci U S A. Mar. 14, 2006;103(11):4005-10.
Leaver-Fay et al., "Computationally Designed Bispecific Antibodies using Negative State Repertoires," Structure. Apr. 5, 2016;24(4):641-651.
Lee et al., "An engineered human Fc domain that behaves like a pH-toggle switch for ultra-long circulation persistence," Nat Commun. Nov. 6, 2019;10(1):5031.
Lin et al., "The antitumor activity of the human FOLR1-specific monoclonal antibody, farletuzumab, in an ovarian cancer mouse model is mediated by antibody-dependent cellular cytotoxicity," Cancer Biol Ther. Nov. 2013;14(11):1032-8.
Liu, "Pharmacokinetics of monoclonal antibodies and Fc-fusion proteins," Protein Cell. Jan. 2018;9(1):15-32.
Loureiro et al., "Adjuvant-Free Immunization with Hemagglutinin-Fc Fusion Proteins as an Approach to Influenza Vaccines," J Virol. Mar. 2011;85(6):3010-4.
Lund et al., "Multiple interactions of IgG with its core oligosaccharide can modulate recognition by complement and human Fc gamma receptor I and influence the synthesis of its oligosaccharide chains," J Immunol. Dec. 1, 1996;157(11):4963-9.
Lund et al.,"Human Fc gamma RI and Fc gamma RII interact with distinct but overlapping sites on human IgG," J Immunol. 1991;147(8):2657-62.
Mekhaiel et al., "Polymeric human Fc-fusion proteins with modified effector functions," Sci Rep. 2011;1:124.

Merchant et al., "An efficient route to human bispecific IgG," Nat Biotechnol. Jul. 1998;16(7):677-81.
Michaelson et al., "Structural difference in the complement activation site of human IgG1 and IgG3," Scand J Immunol. Dec. 2009;70(6):553-64.
Mimoto et al., "Engineering to Improve the Function of Therapeutic Antibodies," Curr Pharm Biotechnol. 2016;17(15):1298-1314.
Moore et al., "A novel bispecific antibody format enables simultaneous bivalent and monovalent co-engagement of distinct target antigens," MAbs. Nov.-Dec. 2011;3(6):546-57.
Moore et al., "A robust heterodimeric Fc platform engineered for efficient development of bispecific antibodies of multiple formats," Methods. Feb. 1, 2019;154:38-50.
Moore et al., "Engineered Fc variant antibodies with enhanced ability to recruit complement and mediate effector functions," MAbs. Mar.-Apr. 2010;2(2):181-9.
Morgan et al., "The N-terminal end of the CH2 domain of chimeric human IgG1 anti-HLA-DR is necessary for C1q, Fc gamma RI and Fc gamma RIII binding," Immunology. 1995;86(2):319-24.
Neville et al., "Analysis of fluorescently labeled glycosphingolipid-derived oligosaccharides following ceramide glycanase digestion and anthranilic acid labeling," Anal Biochem. Aug. 15, 2004;331(2):275-82.
Nielson et al., "Prediction of MHC class II binding affinity using SMM-align, a novel stabilization matrix alignment method," BMC Bioinformatics. Jul. 4, 2007;8:238.
Niesen et al., "The use of differential scanning fluorimetry to detect ligand interactions that promote protein stability," Nat Protoc. 2007;2(9):2212-21.
Niles et al., "A homogeneous assay to measure live and dead cells in the same sample by detecting different protease markers," Anal Biochem. Jul. 15, 2007;366(2):197-206.
Oganesyan et al., "Structural characterization of a human Fc fragment engineered for lack of effector functions," Acta Crystallogr D Biol Crystallogr. Jun. 2008;64(Pt 6):700-4.
Partial Search Report from PCT/GB/2021/051233 dated May 20, 2021.
Paul et al., "Development and validation of a broad scheme for prediction of HLA class II restricted T cell epitopes," J Immunol Methods. Jul. 2015;422:28-34.
PCT International Search Report and Written Option from PCT/GB/2021/051233, dated Nov. 25, 2021.
Petkova et al., "Enhanced half-life of genetically engineered human IgG1 antibodies in a humanized FcRn mouse model: potential application in humorally mediated autoimmune disease," Int Immunol. Dec. 2006;18(12):1759-69.
Proetzel and Roopenian, "Humanized FcRn mouse models for evaluating pharmacokinetics of human IgG antibodies," Methods. Jan. 1, 2014;65(1):148-53.
Ramadhany et al., "Antibody with an engineered Fc region as a therapeutic agent against dengue virus infection," Antiviral Res. 2015;124(39):61-68.
Reddy et al., "Elimination of Fc receptor-dependent effector functions of a modified IgG4 monoclonal antibody to human CD4," J Immunol. 2000;164(4):1925-33.
Reusch et al., "Comparison of methods for the analysis of therapeutic immunoglobulin G Fc-glycosylation profiles—part 1: separation-based methods," MAbs. 2015;7(1):167-79.
Reusch et al., "Comparison of methods for the analysis of therapeutic immunoglobulin G Fc-glycosylation profiles—Part 2: Mass spectrometric methods," MAbs. 2015;7(4):732-42.
Ridgway et al., "Knobs-into-holes' engineering of antibody CH3 domains for heavy chain heterodimerization," Protein Eng. Jul. 1996;9(7):617-21.
Rose et al., "Quantitative analysis of the interaction strength and dynamics of human IgG4 half molecules by native mass spectrometry," Structure. Sep. 7, 2011;19(9):1274-82.
Römer et al., "Preculture of PBMCs at high cell density increases sensitivity of T-cell responses, revealing cytokine release by CD28 superagonist TGN1412," Blood. Dec. 22, 2011;118(26):6772-82.
Saunders, "Conceptual Approaches to Modulating Antibody Effector Functions and Circulation Half-Life," Front Immunol. 2019;10:1296.

(56) References Cited

OTHER PUBLICATIONS

Schlothauer et al., "Novel human IgG1 and IgG4 Fc-engineered antibodies with completely abolished immune effector functions," 2016;29(10):457-466.
Search Report from GB2007613.9 dated Jan. 8, 2021.
Second Examination Report from GB2007613.9 dated Aug. 24, 2021.
Senisterra and Finerty, "High throughput methods of assessing protein stability and aggregation," Mol Biosyst. Mar. 2009;5(3):217-23.
Shan et al., "Generation and Characterization of an IgG4 Monomeric Fc Platform," PLoS One. 2016;11(8):e0160345.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.
Shire, "Formulation and manufacturability of biologics," Curr Opin Biotechnol. 2009;20(6):708-14.
Sidney et al., "Quantitative peptide binding motifs for 19 human and mouse MHC class I molecules derived using positional scanning combinatorial peptide libraries," Immunome Res. Jan. 25, 2008;4:2.
Simeon and Chen, "In vitro-engineered non-antibody protein therapeutics," Protein Cell. Jan. 2018;9(1):3-14.
Stapleton et al., "Human IgG lacking effector functions demonstrate lower FcRn-binding and reduced transplacental transport," Mol Immunol. Mar. 2018;95:1-9.
Strohl, "Current progress in innovative engineered antibodies," Protein Cell. 2018;9(1):86-120.
Strop et al., "Generating bispecific human IgG1 and IgG2 antibodies from any antibody pair," J Mol Biol. 2012;420(3):204-19.
Sturniolo et al., "Generation of tissue-specific and promiscuous HLA ligand databases using DNA microarrays and virtual HLA class II matrices," Nat Biotechnol. Jun. 1999;17(6):555-61.
Tam et al., "Functional, Biophysical, and Structural Characterization of Human IgG1 and IgG4 Fc Variants with Ablated Immune Functionality," Antibodies (Basel). Sep. 1, 2017;6(3):12.
Third Examination Report from GB2007613.9 dated Dec. 15, 2021.
Vaccaro et al., "Engineering the Fc region of immunoglobulin G to modulate in vivo antibody levels," Nat Biotechnol. Oct. 2005;23(10):1283-8.
Vafa et al., "An engineered Fc variant of an IgG eliminates all immune effector functions via structural perturbations," Methods. Jan. 1, 2014;65(1):114-26.
Vessillier et al., "Cytokine release assays for the prediction of therapeutic mAb safety in first-in man trials—Whole blood cytokine release assays are poorly predictive for TGN1412 cytokine storm," J Immunol Methods. Sep. 2015;424:43-52.
Vidarsson et al., "IgG subclasses and allotypes: from structure to effector functions," Front Immunol. 2014;5:520.
Von Kreudenstein et al., "Improving biophysical properties of a bispecific antibody scaffold to aid developability: quality by molecular design," MAbs. Sep.-Oct. 2013;5(5):646-54.
Wang et al., "IgG Fc engineering to modulate antibody effector functions," Protein Cell. 2018;9(1):63-73.
Wang et al., "A systematic assessment of MHC class II peptide binding predictions and evaluation of a consensus approach," PLoS Comput Biol. Apr. 4, 2008;4(4):e1000048.
Werner et al., "Glycosylation of therapeutic proteins in different production systems," Acta Paediatr. 2007;96(455):17-22.
Wilkinson et al., "Monovalent IgG4 molecules: immunoglobulin Fc mutations that result in a monomeric structure," MAbs. May-Jun. 2013;5(3):406-17.
Wing et al., "Ex-vivo whole blood cultures for predicting cytokine-release syndrome: dependence on target antigen and antibody isotype," Ther Immunol. Aug. 1995;2(4):183-90.
Wolf et al., "A whole blood in vitro cytokine release assay with aqueous monoclonal antibody presentation for the prediction of therapeutic protein induced cytokine release syndrome in humans," Cytokine. Dec. 2012;60(3):828-37.
Wozniak-Knopp et al., "Designing Fcabs: well-expressed and stable high affinity antigen-binding Fc fragments," Protein Eng Des Sel. Sep. 1, 2017;30(9):657-671.
Written Opinion of the International Preliminary Examining Authority from PCT/GB/2021/051233 dated Jul. 14, 2022.
Written Opinion of the International Preliminary Examining Authority from PCT/GB/2021/051233 dated Mar. 31, 2022.
Xu et al., "In vitro characterization of five humanized OKT3 effector function variant antibodies," Cell Immunol. Feb. 25, 2000;200(1):16-26.
Yang et al., "Engineering of Fc Fragments with Optimized Physicochemical Properties Implying Improvement of Clinical Potentials for Fc-Based Therapeutics," Front Immunol. Jan. 8, 2018;8:1860.
Yeung et al., "Engineering human IgG1 affinity to human neonatal Fc receptor: impact of affinity improvement on pharmacokinetics in primates," J Immunol. Jun. 15, 2009;182(12):7663-71.
Ying et al., "Monomeric IgG1 Fc molecules displaying unique Fc receptor interactions that are exploitable to treat inflammation-mediated diseases," MAbs. 2014;6(5):1201-10.
Ying et al., "Soluble monomeric IgG1 Fc," J Biol Chem. Jun. 1, 2012;287(23):19399-408.
Zalevsky et al., "Enhanced antibody half-life improves in vivo activity," Nat Biotechnol. Feb. 2010;28(2):157-9.
Zhou, "Site-Specific Antibody Conjugation for ADC and Beyond," Biomedicines. Nov. 9, 2017;5(4):64.
Jain, et. al. "Biophysical properties of the clinical-stage antibody landscape." Proc Natl Acad Sci U S A. Jan. 31, 2017;114(5):944-949. doi: 10.1073/pnas.1616408114. Epub Jan. 17, 2017. PMID: 28096333; PMCID: PMC5293111.
Second Office Action from CA 3,179,582 dated Jun. 12, 2023.

\* cited by examiner

Figure 1A. Amino acid sequences of IgG Fc regions

| | 216 | 217 | 218 | 219 | 220 | 221 | 222 | 223 | 224 | 225 | 226 | 227 | 228 | 228a | 228b | 228c | 228d | 228e | 228f | 229 | 230 |
|---|---|---|---|---|---|---|---|---|---|---|---|---|---|---|---|---|---|---|---|---|---|
| human IgG1 | E | P | K | S | C | D | K | T | H | T | C | P | P | | | | | | | C | P |
| human IgG2 | E | R | K | C | C | V | E | - | - | - | C | P | P | | | | | | | C | P |
| human IgG4 | E | S | K | - | - | - | Y | G | P | P | C | P | S | | | | | | | C | P |
| mouse IgG2a | E | P | R | G | P | T | I | K | - | P | C | P | P | C | | | | | | K | C P |
| rat IgG2b | E | R | R | N | G | G | I | G | H | K | C | P | T | C | P | T | C | H | K | C | P |
| rabbit IgG | A | P | S | T | C | S | K | P | - | T | C | P | P | | | | | | | - | - |

| | 231 | 232 | 233 | 234 | 235 | 236 | 237 | 238 | 239 | 240 | 241 | 242 | 243 | 244 | 245 | 246 | 247 | 248 | 249 | 250 |
|---|---|---|---|---|---|---|---|---|---|---|---|---|---|---|---|---|---|---|---|---|
| human IgG1 | A | P | E | L | L | G | G | P | S | V | F | L | F | P | P | K | P | K | D | T |
| human IgG2 | A | P | P | V | A | - | G | P | S | V | F | L | F | P | P | K | P | K | D | T |
| human IgG4 | A | P | E | F | L | G | G | P | S | V | F | L | F | P | P | K | P | K | D | T |
| mouse IgG2a | A | P | N | L | L | G | G | P | S | V | F | I | F | P | P | K | I | K | D | V |
| rat IgG2b | V | P | E | L | L | G | G | P | S | V | F | I | F | P | P | K | P | K | D | I |
| rabbit IgG | - | P | E | L | L | G | G | P | S | V | F | I | F | P | P | K | P | K | D | T |

| | 251 | 252 | 253 | 254 | 255 | 256 | 257 | 258 | 259 | 260 | 261 | 262 | 263 | 264 | 265 | 266 | 267 | 268 | 269 | 270 |
|---|---|---|---|---|---|---|---|---|---|---|---|---|---|---|---|---|---|---|---|---|
| human IgG1 | L | M | I | S | R | T | P | E | V | T | C | V | V | V | D | V | S | H | E | D |
| human IgG2 | L | M | I | S | R | T | P | E | V | T | C | V | V | V | D | V | S | H | E | D |
| human IgG4 | L | M | I | S | R | T | P | E | V | T | C | V | V | V | D | V | S | Q | E | D |
| mouse IgG2a | L | M | I | S | L | S | P | I | V | T | C | V | V | V | D | V | S | E | D | D |
| rat IgG2b | L | L | I | S | Q | N | A | K | V | T | C | V | V | V | D | V | S | E | E | E |
| rabbit IgG | L | M | I | S | R | T | P | E | V | T | C | V | V | V | D | V | S | E | D | D |

| | 271 | 272 | 273 | 274 | 275 | 276 | 277 | 278 | 279 | 280 | 281 | 282 | 283 | 284 | 285 | 286 | 287 | 288 | 289 | 290 |
|---|---|---|---|---|---|---|---|---|---|---|---|---|---|---|---|---|---|---|---|---|
| human IgG1 | P | E | V | K | F | N | W | Y | V | D | G | V | E | V | H | N | A | K | T | K |
| human IgG2 | P | E | V | Q | F | N | W | Y | V | D | G | V | E | V | H | N | A | K | T | K |
| human IgG4 | P | E | V | Q | F | N | W | Y | V | D | G | V | E | V | H | N | A | K | T | K |
| mouse IgG2a | P | D | V | Q | I | S | W | F | V | N | N | V | E | V | H | T | A | Q | T | Q |
| rat IgG2b | P | D | V | Q | F | S | W | F | V | N | N | V | E | V | H | T | A | Q | T | Q |
| rabbit IgG | P | E | V | Q | F | T | W | Y | I | N | N | E | Q | V | R | T | A | R | P | P |

Figure 1B. Amino acid sequences of IgG Fc regions

| | | 291 | 292 | 293 | 294 | 295 | 296 | 297 | 298 | 299 | 300 | 301 | 302 | 303 | 304 | 305 | 306 | 307 | 308 | 309 | 310 |
|---|---|---|---|---|---|---|---|---|---|---|---|---|---|---|---|---|---|---|---|---|---|
| human | IgG1 | P | R | E | E | Q | Y | N | S | T | Y | R | V | V | S | V | L | T | V | L | H |
| human | IgG2 | P | R | E | E | Q | F | N | S | T | F | R | V | V | S | V | L | T | V | V | H |
| human | IgG4 | P | R | E | E | Q | F | N | S | T | Y | R | V | V | S | V | L | T | V | L | H |
| mouse | IgG2a | T | H | R | E | D | Y | N | S | T | L | R | V | V | S | A | L | P | I | Q | H |
| rat | IgG2b | P | R | E | E | Q | Y | N | S | T | F | R | V | V | S | A | L | P | I | Q | H |
| rabbit | IgG | L | R | E | Q | Q | F | N | S | T | I | R | V | V | S | T | L | P | I | A | H |

| | | 311 | 312 | 313 | 314 | 315 | 316 | 317 | 318 | 319 | 320 | 321 | 322 | 323 | 324 | 325 | 326 | 327 | 328 | 329 | 330 |
|---|---|---|---|---|---|---|---|---|---|---|---|---|---|---|---|---|---|---|---|---|---|
| human | IgG1 | Q | D | W | L | N | G | K | E | Y | K | C | K | V | S | N | K | A | L | P | A |
| human | IgG2 | Q | D | W | L | N | G | K | E | Y | K | C | K | V | S | N | K | G | L | P | A |
| human | IgG4 | Q | D | W | L | N | G | K | E | Y | K | C | K | V | S | N | K | G | L | P | S |
| mouse | IgG2a | Q | D | W | M | S | G | K | E | F | K | C | K | V | N | N | K | D | L | P | A |
| rat | IgG2b | Q | D | W | M | S | G | K | E | F | K | C | K | V | N | N | K | A | L | P | S |
| rabbit | IgG | E | D | W | L | R | G | K | E | F | K | C | K | V | H | N | K | A | L | P | A |

| | | 331 | 332 | 333 | 334 | 335 | 336 | 337 | 338 | 339 | 340 | 341 | 342 | 343 | 344 | 345 | 346 | 347 | 348 | 349 | 350 |
|---|---|---|---|---|---|---|---|---|---|---|---|---|---|---|---|---|---|---|---|---|---|
| human | IgG1 | P | I | E | K | T | I | S | K | A | K | G | Q | P | R | E | P | Q | V | Y | T |
| human | IgG2 | P | I | E | K | T | I | S | K | T | K | G | Q | P | R | E | P | Q | V | Y | T |
| human | IgG4 | S | I | E | K | T | I | S | K | A | K | G | Q | P | R | E | P | Q | V | Y | T |
| mouse | IgG2a | P | I | E | R | T | I | S | K | P | K | G | S | V | R | A | P | Q | V | Y | V |
| rat | IgG2b | P | I | E | K | T | I | S | K | P | K | G | L | V | R | K | P | Q | V | Y | V |
| rabbit | IgG | P | I | E | K | T | I | S | K | A | R | G | Q | P | L | E | P | K | V | Y | T |

| | | 351 | 352 | 353 | 354 | 355 | 356 | 357 | 358 | 359 | 360 | 361 | 362 | 363 | 364 | 365 | 366 | 367 | 368 | 369 | 370 |
|---|---|---|---|---|---|---|---|---|---|---|---|---|---|---|---|---|---|---|---|---|---|
| human | IgG1 | L | P | P | S | R | D | E | L | T | K | N | Q | V | S | L | T | C | L | V | K |
| human | IgG2 | L | P | P | S | R | E | E | M | T | K | N | Q | V | S | L | T | C | L | V | K |
| human | IgG4 | L | P | P | S | Q | E | E | M | T | K | N | Q | V | S | L | T | C | L | V | K |
| mouse | IgG2a | L | P | P | P | E | E | E | M | T | K | K | Q | V | T | L | T | C | M | V | T |
| rat | IgG2b | M | G | P | P | T | E | Q | L | T | E | Q | T | V | S | L | T | C | L | T | S |
| rabbit | IgG | M | G | P | P | R | E | E | L | S | S | R | S | V | S | L | T | C | M | I | N |

Figure 1C. Amino acid sequences of IgG Fc regions

| | | 371 | 372 | 373 | 374 | 375 | 376 | 377 | 378 | 379 | 380 | 381 | 382 | 383 | 384 | 385 | 386 | 387 | 388 | 389 | 390 |
|---|---|---|---|---|---|---|---|---|---|---|---|---|---|---|---|---|---|---|---|---|---|
| human | IgG1 | G | F | Y | P | S | D | I | A | V | E | W | E | S | N | G | Q | P | E | N | N |
| human | IgG2 | G | F | Y | P | S | D | I | A | V | E | W | E | S | N | G | Q | P | E | N | N |
| human | IgG4 | G | F | Y | P | S | D | I | A | V | E | W | E | S | N | G | Q | P | E | N | N |
| mouse | IgG2a | D | F | M | P | E | D | I | Y | V | E | W | T | N | N | G | K | T | E | L | N |
| rat | IgG2b | G | F | L | P | N | D | I | G | V | E | W | T | S | N | G | H | I | E | K | N |
| rabbit | IgG | G | F | Y | P | S | D | I | S | V | E | W | E | K | N | G | K | A | E | D | N |

| | | 391 | 392 | 393 | 394 | 395 | 396 | 397 | 398 | 399 | 400 | 401 | 402 | 403 | 404 | 405 | 406 | 407 | 408 | 409 | 410 |
|---|---|---|---|---|---|---|---|---|---|---|---|---|---|---|---|---|---|---|---|---|---|
| human | IgG1 | Y | K | T | T | P | [P] | V | L | D | S | D | G | S | F | F | L | Y | S | K | L |
| human | IgG2 | Y | K | T | T | P | P | M | L | D | S | D | G | S | F | F | L | Y | S | K | L |
| human | IgG4 | Y | K | T | T | P | P | V | L | D | S | D | G | S | F | F | L | Y | S | R | L |
| mouse | IgG2a | Y | K | N | T | E | P | V | L | D | S | D | G | S | Y | F | M | Y | S | K | L |
| rat | IgG2b | Y | K | N | T | E | P | V | M | D | S | D | G | S | F | F | M | Y | S | K | L |
| rabbit | IgG | Y | K | T | T | P | A | V | L | D | S | D | G | S | Y | F | L | Y | S | K | L |

| | | 411 | 412 | 413 | 414 | 415 | 416 | 417 | 418 | 419 | 420 | 421 | 422 | 423 | 424 | 425 | 426 | 427 | 428 | 429 | 430 |
|---|---|---|---|---|---|---|---|---|---|---|---|---|---|---|---|---|---|---|---|---|---|
| human | IgG1 | T | V | D | K | S | R | W | Q | Q | G | N | V | F | S | C | S | V | [M] | H | E |
| human | IgG2 | T | V | D | K | S | R | W | Q | Q | G | N | V | F | S | C | S | V | M | H | E |
| human | IgG4 | T | V | D | K | S | R | W | Q | E | G | N | V | F | S | C | S | V | M | H | E |
| mouse | IgG2a | R | V | E | K | K | N | W | V | E | R | N | S | Y | S | C | S | V | V | H | E |
| rat | IgG2b | N | V | E | R | S | R | W | D | S | R | A | P | F | V | C | S | V | V | H | E |
| rabbit | IgG | S | V | P | T | S | E | W | Q | R | G | D | V | F | T | C | S | V | M | H | E |

| | | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|
| human | IgG1 | A | L | H | N | H | Y | T | Q | K | S | L | S | L | S | P | G | K |
| human | IgG2 | A | L | H | N | H | Y | T | Q | K | S | L | S | L | S | P | G | K |
| human | IgG4 | A | L | H | N | H | Y | T | Q | K | S | L | S | L | S | L | G | K |
| mouse | IgG2a | G | L | H | N | H | H | T | T | K | S | F | S | R | T | P | G | K |
| rat | IgG2b | G | L | H | N | H | H | V | E | K | S | I | S | R | P | P | G | K |
| rabbit | IgG | A | L | H | N | H | Y | T | Q | K | S | I | S | R | S | P | G | K |

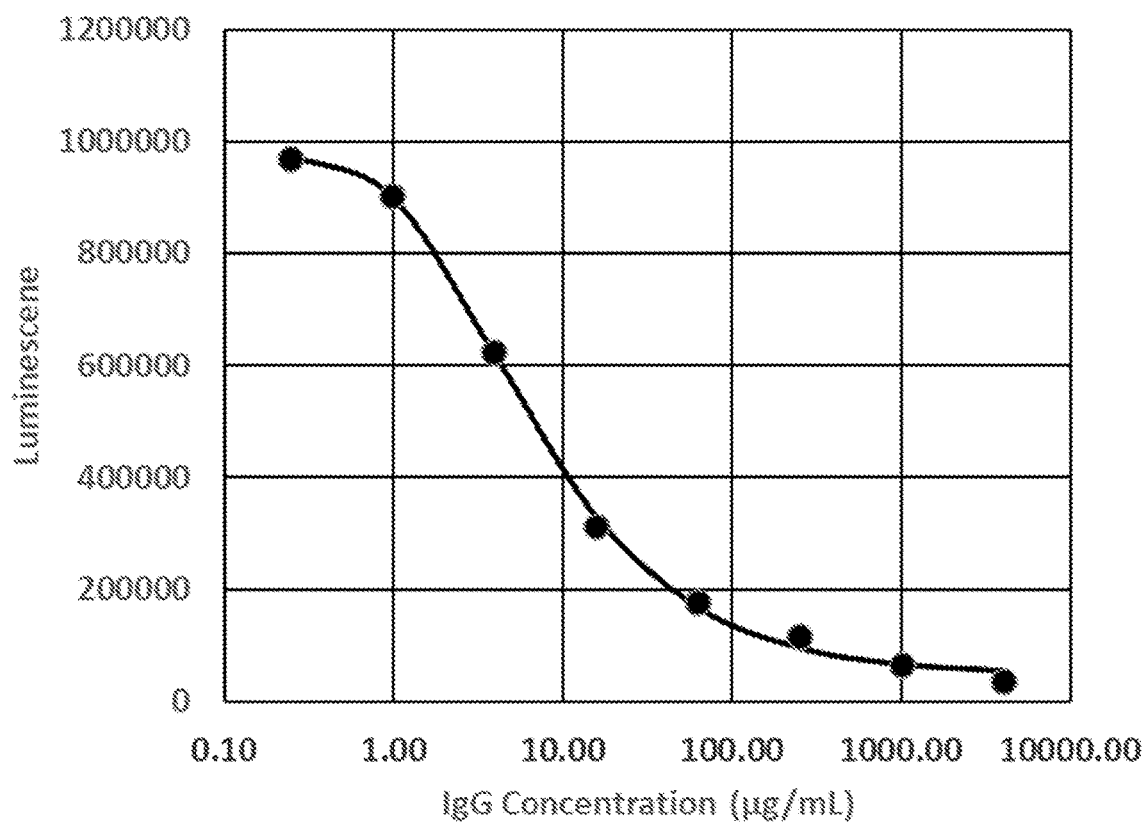
Figure 2. NanoBiT® FcRn Immunoassay Calibration Curve

Figure 3. ADCC with FcγRIII
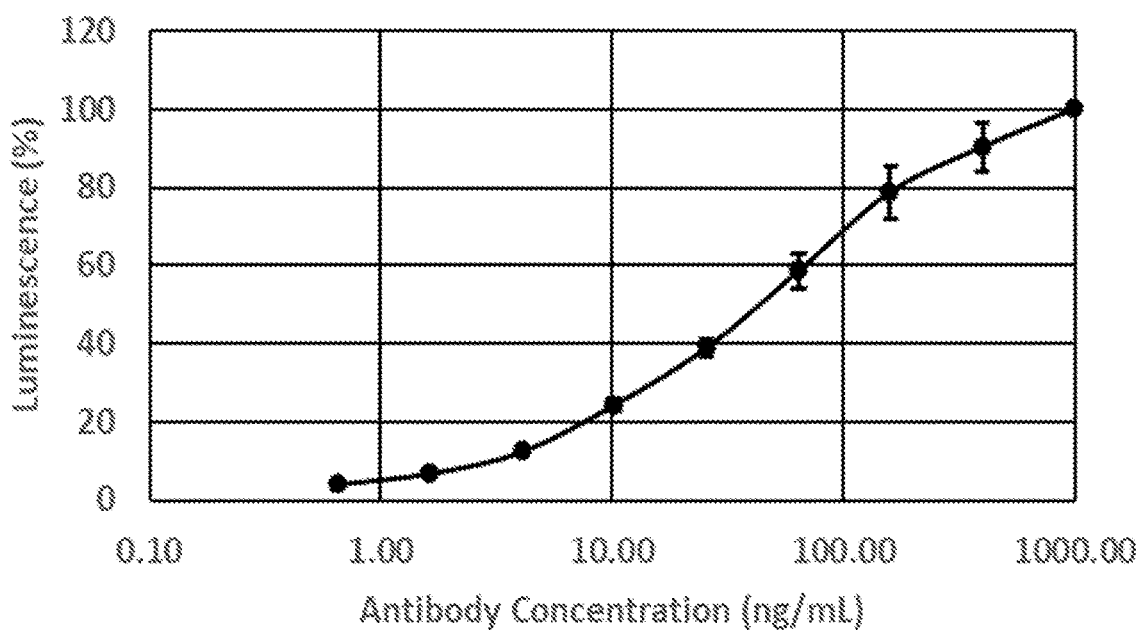

Figure 4. ADCP with FcγRII
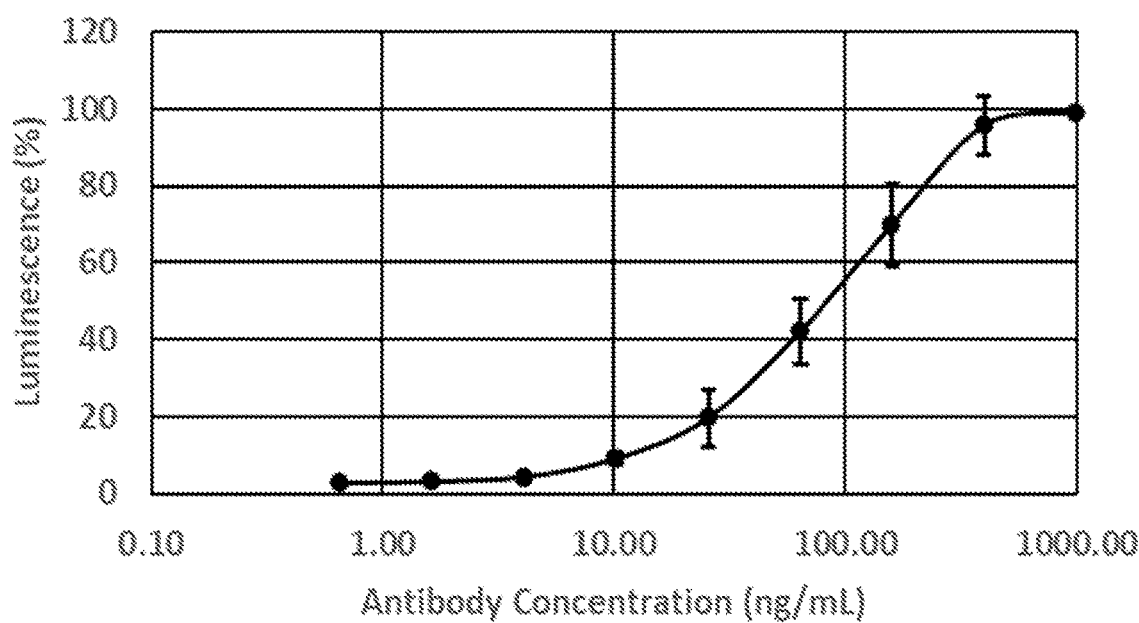

Figure 5A. Cytokine release: GM-CSF and IFNg
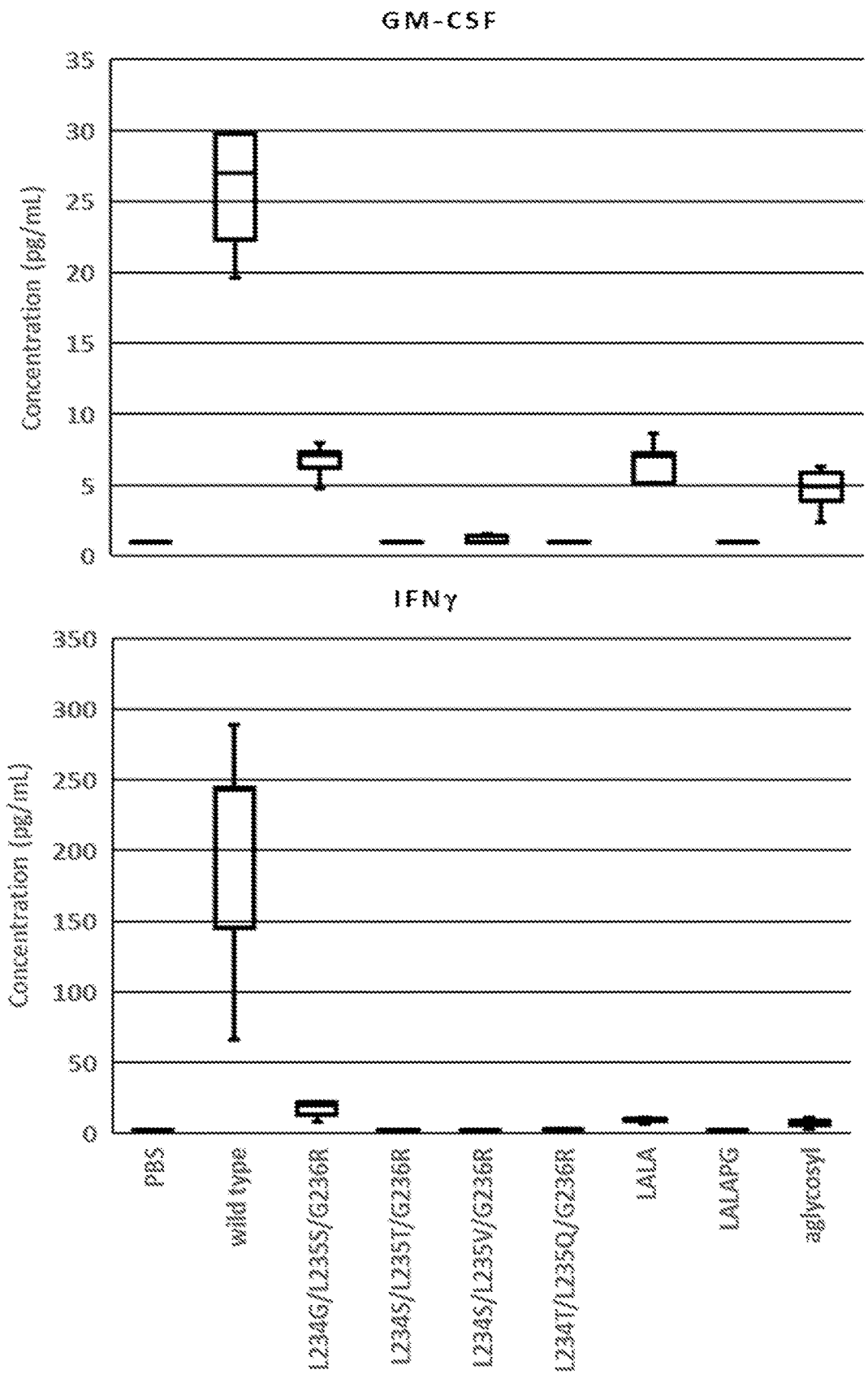

Figure 5B. Cytokine release: IL-2 and IL-4
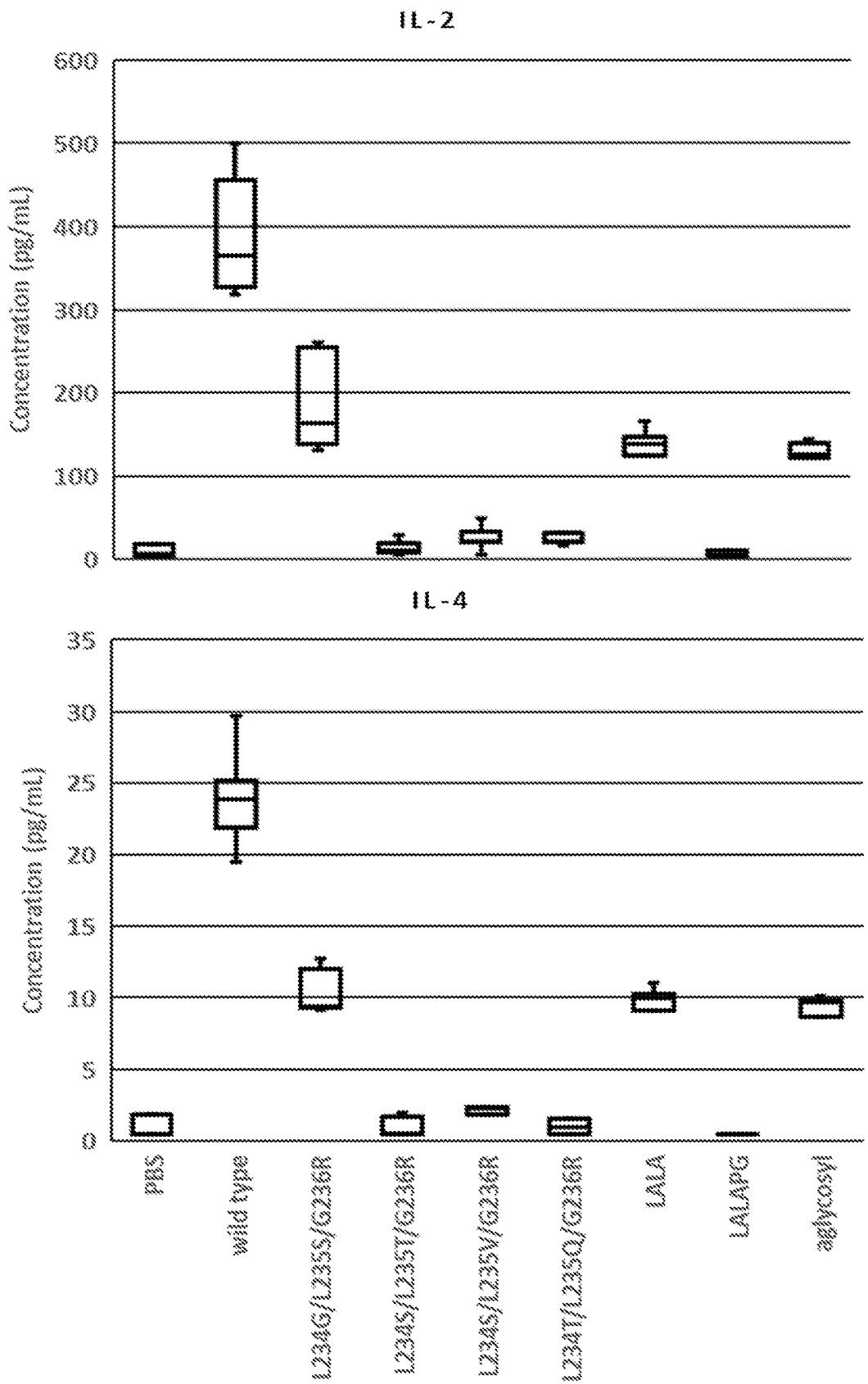

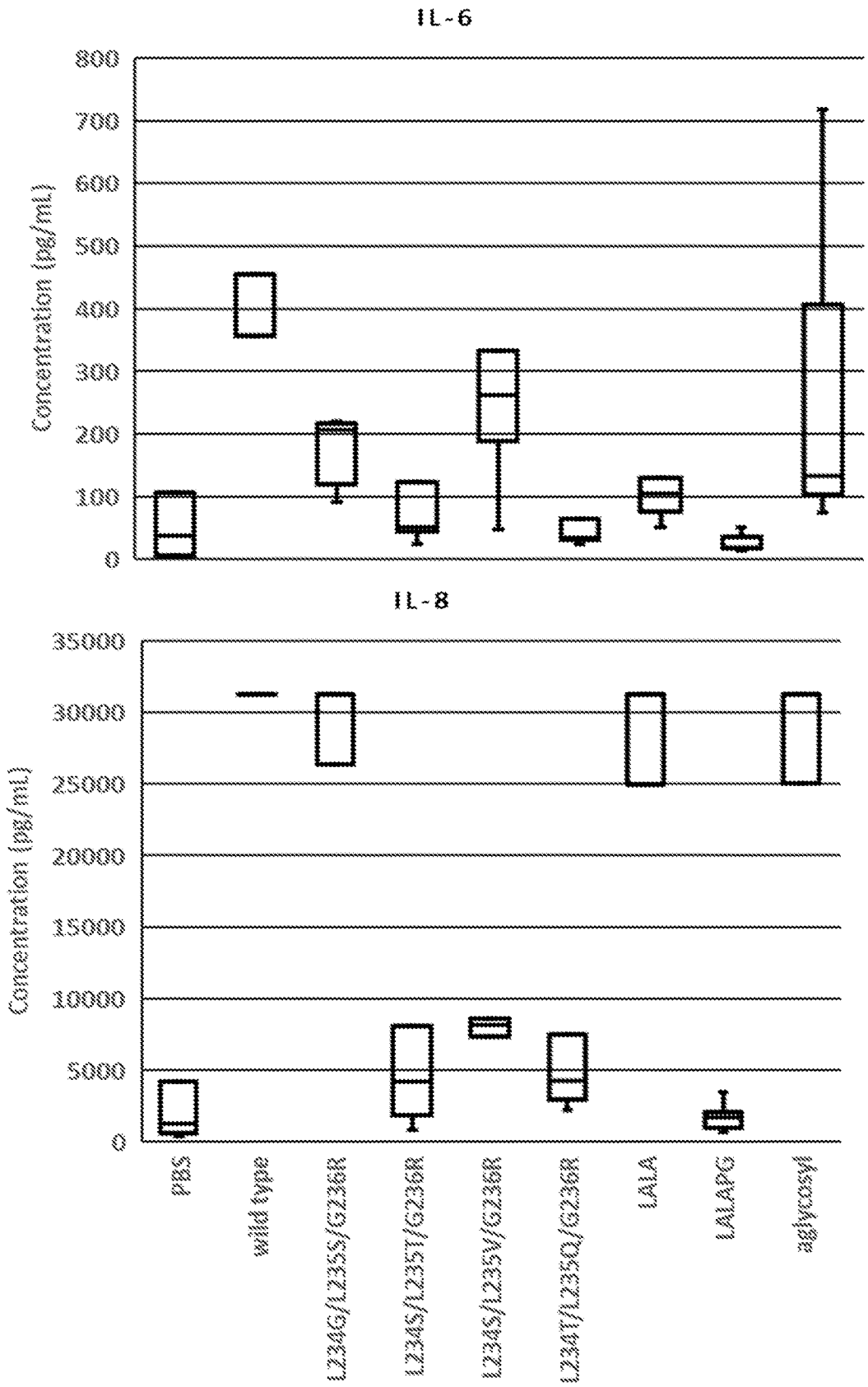
Figure 5C. Cytokine release: IL-6 and IL-8

Figure 5D. Cytokine release: IL-10 and TNFa
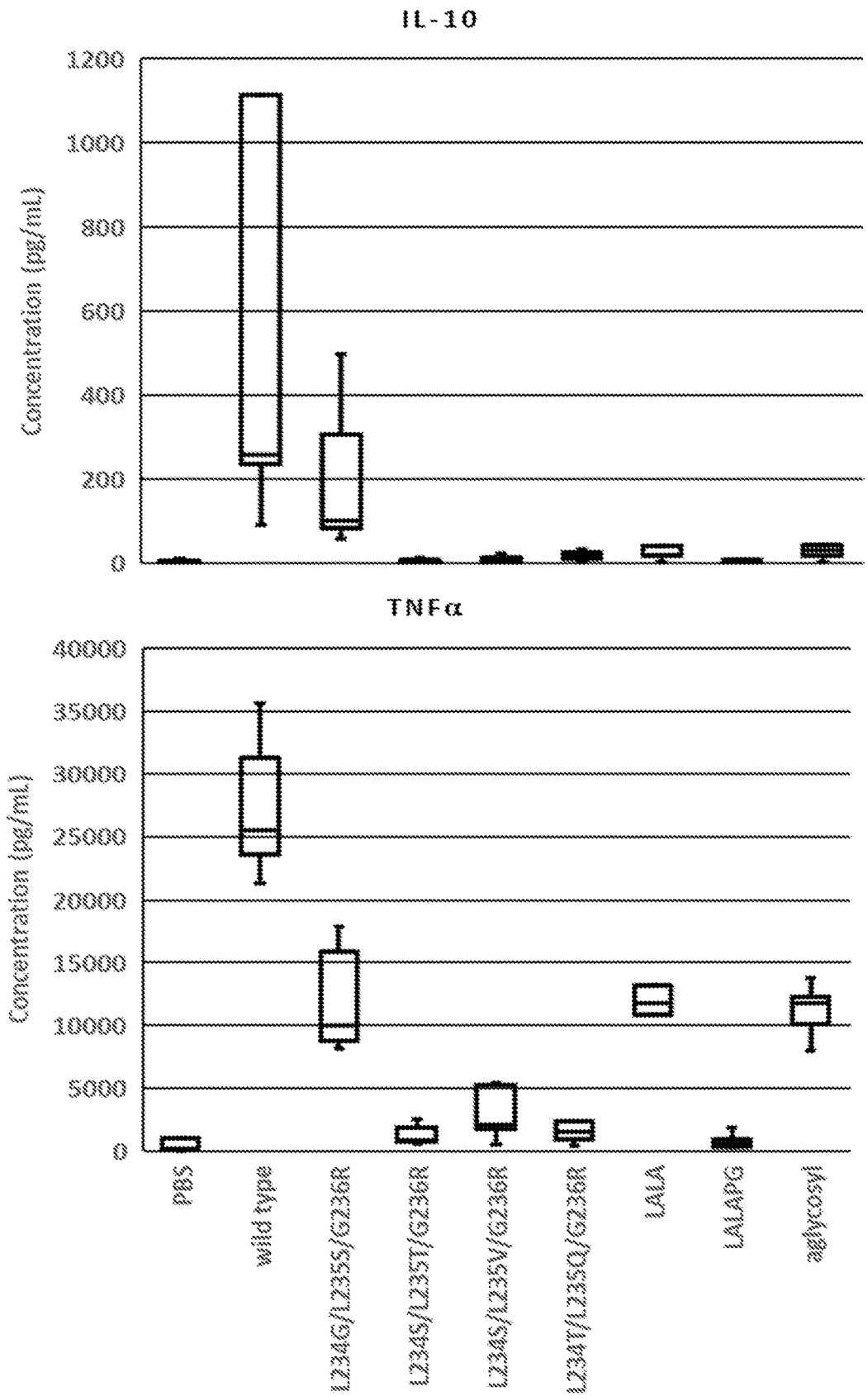

Figure 6A. Carbohydrate analysis by hydrophilic interaction liquid chromatography
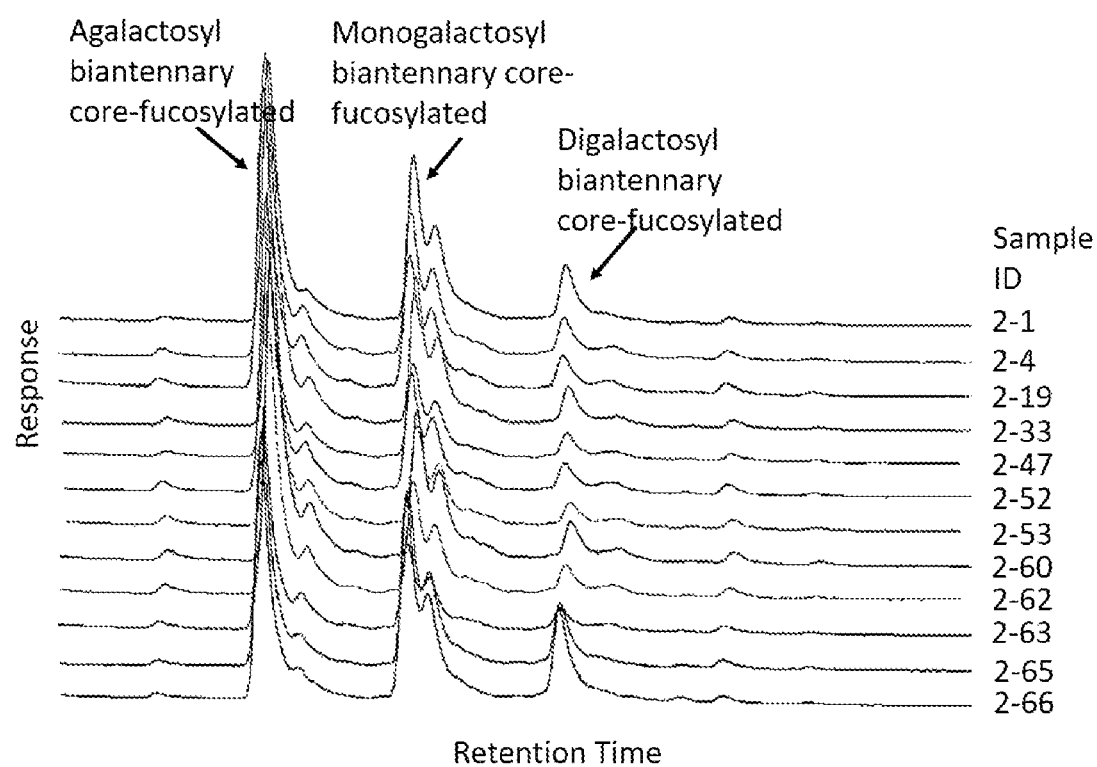

Figure 6B. Carbohydrate analysis by hydrophilic interaction liquid chromatography
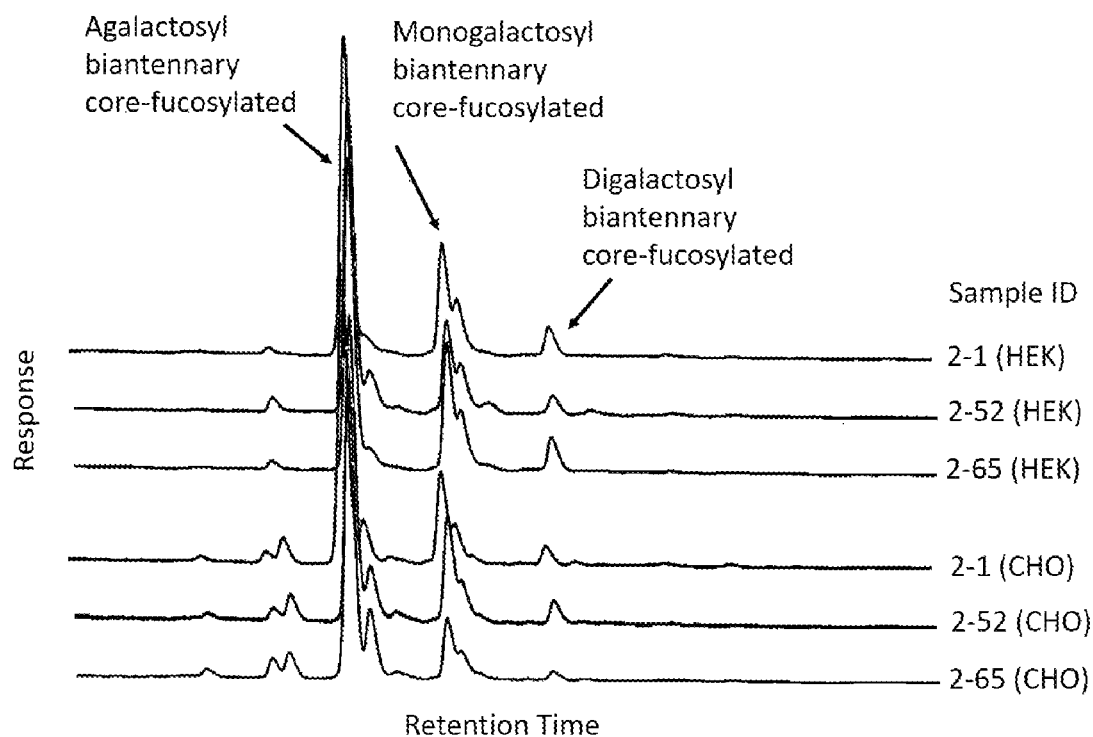

MODIFIED IMMUNOGLOBULIN Fc REGIONS

CROSS-REFERENCE TO RELATED APPLICATIONS

This application is a continuation of PCT International Application No. PCT/GB2021/051223, filed May 20, 2021, which claims the benefit of GB Patent Application No. GB 2007613.9 filed May 21, 2020. The entirety of each application is incorporated herein by reference thereto.

INCORPORATION BY REFERENCE OF SEQUENCE LISTING

This application contains a Sequence Listing in computer readable form (filename: P000249WOUS_Sequence_ Listing: 31,974 bytes, created Nov. 18, 2022), which is incorporated herein by reference in its entirety and forms part of the disclosure.

FIELD OF THE INVENTION

The present invention relates to proteins which comprise a variant immunoglobulin Fc region having mutations which essentially eliminate binding to Fc receptors.

BACKGROUND

Antibodies are typically made up of regions which are structurally and functionally distinct. Variable regions are responsible for binding antigens whereas constant regions interact with a number of ligands, such as C1q and Fc receptors, and endow the antibody with particular physiological capabilities or effector functions.

In humans there are three classes of Fcγ receptors which interact with IgG to initiate immune responses: FcγRI (CD64), FcγRII (CD32) and FcγRIII (CD16) (Bruhns 2009). One or more of these receptors are found on the surface of almost all white blood cells with the exception of T cells. The responses they mediate include release of cytokines, B cell activation and differentiation, endocytosis, phagocytosis and cytotoxicity. Each receptor is characterized by an alpha chain that binds to the IgG Fc region and is associated with a signalling motif, either in a cytoplasmic portion of the alpha chain or in an associated membrane protein.

FcγRI binds to human IgG1 and IgG3 with relatively high affinity and to IgG4 with lower affinity, is found on monocytes and macrophages and is involved with phagocytosis of immune complexes and release of immune mediators. FcγRII exists in three forms with differing functions and cellular distributions. They have low affinity for IgG1 and IgG3 but bind aggregated IgG more avidly. FcγRIIA is expressed on monocytes, granulocytes and platelets. It has an ITAM motif in its cytoplasmic tail which mediates cellular activation. One allele also binds IgG2. FcγRIIB is found in B cells and has an ITIM motif which blocks cellular activation. There are two forms of FcγRIII. Both have moderate affinity for monomeric IgG1 and IgG3. FcγRIIIA, like the other FcRs, is a transmembrane glycoprotein. It is found on monocytes, macrophages, NK cells and some T cells and is associated with separate membrane proteins having ITAM motifs. FcγRIIIB is a lipid-anchored glycoprotein found on neutrophils. There are different alleles of both forms of FcγRIII which differ in binding to IgG and/or functional activity.

SUMMARY OF INVENTION

Surprisingly, we have identified proteins containing a variant Fc region which comprise new sets of amino acid substitutions that result in significantly lower binding to FcγRI than seen with known variant Fc regions which do have discernible binding to FcγRI. We provide proteins comprising a variant IgG Fc domain or region, wherein the proteins exhibit significantly reduced binding to human FcγRI when compared with a reference protein comprising the amino acid substitutions L234A/L235A/P329G. Also provided are compositions, methods of treatment and methods to reduce Fc-induced effector functions in a parent protein.

In a first aspect of the invention, a protein comprising a variant Fc region or variant Cγ2 domain is provided, wherein the variant Fc region or variant Cγ2 domain comprises: (a) an amino acid substitution at position 234 or an amino acid substitution at position 235 or amino acid substitutions at both positions 234 and 235; and (b) an amino acid alteration to arginine (R) at position 236, wherein the amino acid numbering is according to the EU index as in Kabat, and wherein the binding of the protein to human FcγRI is significantly reduced compared with the binding of a LALAPG reference protein.

In a second aspect of the invention, a protein comprising a variant IgG Fc region is provided, wherein the variant IgG Fc region comprises a combination of amino acid substitutions selected from the group defined in claim 19, wherein the amino acid numbering is according to the EU index as in Kabat.

In a third aspect of the invention, a nucleic acid comprising a sequence encoding the protein as defined above is provided.

In further aspects, a composition, vector or host cell comprising a nucleic acid as defined above is provided.

In a further aspect, there is provided a method of making a protein as defined above, comprising (a) culturing a host cell as defined above; and (b) isolating the protein.

In a further aspect, a conjugate or a composition comprising a protein as defined above is provided.

In a further aspect, a method to reduce Fc-mediated effector function of a protein comprising an IgG Fc region is provided, the method comprising: (a) design, synthesis and expression of a gene encoding the protein as defined above and (b) isolation of the protein.

In a further aspect, a method of treating a mammal is provided, comprising administering to the mammal an effective amount of a protein, conjugate, composition or a vector, as defined above.

In a further aspect, a protein, conjugate, composition or a vector, as defined above, is provided for use as a medicament, wherein reduced effector function of the said protein: (a) reduces the likelihood of adverse clinical effects, (b) increases the likelihood of beneficial clinical effects or (c) facilitates the use of higher doses, more frequent doses or more doses when compared with a reference protein.

In a further aspect, a protein, conjugate, composition or a vector, as defined above, is provided for use in a test system for research or diagnosis or quality control, including for example for use in an enzyme-linked immunosorbent assay (ELISA), a fluorescence-based assay, an immunohistochemistry test or a diagnostic imaging test.

BRIEF DESCRIPTION OF THE FIGURES

The invention will now be described with reference to the following, non-limiting figures, wherein:

FIG. 1A, FIG. 1B, and FIG. 1C show an alignment of amino acid sequences of wild-type immunoglobulin Fc regions from human IgG1 (SEQ ID NO:1), human IgG2 (residues 99-326 of SEQ ID NO: 18), human IgG4 (residues 99-327 of SEQ ID NO: 19), mouse IgG2a (residues 98-330 of SEQ ID NO: 20), rat IgG2b (residues 96-333 of SEQ ID NO: 22) and rabbit IgG (residues 96-323 of SEQ ID NO:24). The residues are numbered according to the EU index. Amino acid residues which have been altered in various variants described herein are highlighted with a box.

FIG. 2 shows the dose response for human IgG in a NanoBiT® FcRn Immunoassay. The luminescence response (mean of duplicates) is plotted against the concentration of human IgG.

FIG. 3 shows the dose response for wild-type CD20 reference antibody in an ADCC assay. The luminescence response (mean of 8 replicates) is plotted together with the standard deviation of the means as a percentage of the response at a 1000 ng/mL FIG. 4 shows the dose response for wild-type CD20 reference antibody in an ADCP assay. The luminescence response (mean of 4 replicates) is plotted together with the standard deviation of the means as a percentage of the response at a 1000 ng/mL.

FIG. 5A to FIG. 5D show the release of cytokines from peripheral blood mononuclear cells from five healthy donors after stimulations with wild-type or variant CD3 antibodies at a final concentration of 10 µg/mL.

FIG. 6A and FIG. 6B show the analysis by hydrophilic interaction liquid chromatography of carbohydrates released from samples of wild-type and variant CD20 antibodies. Samples as described in Table 5 were prepared from HEK cells (FIG. 6A) or from HEK cells and CHO cells (FIG. 6B).

DETAILED DESCRIPTION

Definitions

The meaning of certain terms used in this invention may be different from the meanings of similar terms used in the literature. Definitions of such terms, in the context of this invention, are provided below.

Unless defined otherwise, all technical and scientific terms have the same meaning as commonly understood by one of ordinary skill in the art to which this invention is related. For example, the Dictionary of Microbiology and Molecular Biology, Third Edition 2006, John Wiley & Sons Ltd and the Oxford Dictionary of Biochemistry and Molecular Biology, Second edition 2006, Oxford University Press, provide general dictionaries of many of the terms used in this invention.

Amino acids may be referred to by either their commonly known three letter symbols or by the one-letter symbols recommended by the IUPAC-IUB Biochemical Nomenclature Commission. Nucleotides, likewise, may be referred to by their commonly accepted single-letter codes.

Throughout this specification and claims, the numbering of amino acid residues in immunoglobulins is that of human IgG1 EU myeloma protein (the "EU index").

Approximately. The terms "about" or "approximately" in relation to a numerical value X means, for example, X plus or minus 20%.

Affinity. The term "affinity" means the tendency for two molecules (for example an immunoglobulin Fc region and a Fc receptor) to associate (bind) non-covalently, that is by means of interactions that do not involve the formation of covalent chemical bonds. If two molecules have an affinity for each other that means there is a favourable tendency for them to associate specifically and non-covalently to form a complex or complexes. For the purposes of this application, the magnitude of the affinity may be defined in terms of ratios of concentrations of the free molecules and complexes to give an association constant for the interaction under certain conditions of temperature, salt concentration and pH. Alternatively, it may be defined as a relative affinity, being a ratio of measurements correlated with association constants for a molecule of interest (for example a variant Fc region) binding to a target molecule (for example a Fc receptor) and a reference molecule (for example a wild-type reference, LALAPG reference or LALA reference) binding to the same target molecule under the same experimental conditions.

Amino acid alteration. The term "amino acid alteration" refers to a change in the amino acid sequence of a predetermined amino acid sequence. Exemplary alterations include the substitution, insertion or deletion of an amino acid residue. A substitute or inserted amino acid residue is a naturally occurring amino acid residue (i.e. encoded by the genetic code).

Amino acid deletion. The term "amino acid deletion" refers to the deletion of at least one amino acid in a predetermined amino acid sequence. Throughout this specification and claims, amino acid deletions may be described thus: XnnnΔ, where X is the single letter code for the residue in the predetermined amino acid sequence, nnn is the position in that sequence as defined by the EU index and Δ (Greek delta) indicates that the specified amino acid residue is deleted.

Amino acid insertion. The term "amino acid insertion" refers to the insertion of at least one amino acid in a predetermined amino acid sequence. Throughout this specification and claims, amino acid insertions may be described thus: ΔnnnX, where Δ (Greek delta) indicates that the specified amino acid residue is absent in the predetermined amino acid sequence, nnn is the position in that sequence as defined by the EU index and X is the single letter code for the residue which is inserted.

Amino acid substitution. The term "amino acid substitution" refers to the replacement of at least one amino acid residue in a predetermined amino acid sequence. The replacement residue is a naturally occurring amino acid residue (i.e. encoded by the genetic code). Throughout this specification and claims, amino acid substitutions may be described thus: XnnnY, where X is the single letter code for the residue in the predetermined amino acid sequence, nnn is the position in that sequence as defined by the EU index and Y is the single letter code for the replacement amino acid residue.

Antibody. The term "antibody" includes an immunoglobulin molecule or fragment thereof with one or more protein chains comprising at least one domain which can potentially bind to an antigen (the "antigen-binding domain"). The immunoglobulin may be of any isotype (for example IgG, IgE, IgM, IgD, IgA or IgY), subtype (for example IgG1, IgG2, IgG2a, IgG2b, IgG2c, IgG3, IgG4, IgA1 and IgA2) or allotype or it may be a hybrid derived from more than one isotype, subtype or allotype. The immunoglobulin may be of any species (for example human, monkey, camel, llama, goat, sheep, rabbit, mouse, rat, mouse, hamster or chicken) or it may be a hybrid derived from more than one species. The antibody may be a polyclonal antibody or a monoclonal antibody. It may be naturally occurring or it may be non-naturally occurring (i.e. an isolated antibody). The antibody may be created by genetic engineering (for example a chimeric antibody, humanised antibody, camelised antibody, intrabody, bispecific antibody). It may be a fragment (for example Fab fragment, F(ab')2 fragment, Fv fragment, single-chain Fv fragment). According to this definition, "antibody" includes both polyclonal and monoclonal antibodies or any mixture of them. The protein of the invention can be an antibody or antibody fragment according to any of the definitions of "antibody" provided herein.

Antibody dependent cell-mediated cytotoxicity. Antibody dependent cell-mediated cytotoxicity (ADCC), also referred to as antibody dependent cellular cytotoxicity, is a mechanism of immune defence whereby an effector cell of the immune system actively lyses a target cell to which an antibody or any other protein comprising an Fc region is bound. ADCC is mediated through binding of an immunoglobulin Fc region to an Fc receptor on the effector cell. It may involve various types of Fc receptor and various types of effector cells but commonly is mediated through FcγRIIIA expressed on natural killer (NK) cells.

Antibody dependent cell-mediated phagocytosis. Antibody dependent cell-mediated phagocytosis (ADCP), is a mechanism of immune defence whereby an effector cell of the immune system phagocytoses a target cell to which an antibody or any other protein comprising an Fc region is bound. ADCP can be mediated by monocytes, macrophages, neutrophils or dendritic cells via FcγRIIA (CD32A), FcγRI (CD64), and/or FcγRIIIA (CD16A).

Binding. In the context of this invention "binding" refers to a reversible interaction, typically between macromolecules such as proteins. In the simplest case, the binding interaction between two macromolecules A and B can be represented by the equation:

$$A+B=AB$$

According to the law of mass action, the rate of the forward reaction is equal to a rate constant, $k_a$, multiplied by the concentrations of the separate reactants, i.e. $k_a \times [A] \times [B]$, and the rate of the back reaction is equal to a rate constant, $k_d$, multiplied by the concentration of the complex, i.e. $k_d \times [AB]$ (where square brackets indicate concentrations of the reactants). At equilibrium the rate of both reactions is the same, and the binding affinity can be defined in terms of the ratio of the rate constants either as an association constant, $K_a$:

$$K_a = \frac{k_a}{k_d} = \frac{[AB]}{[A][B]} \quad (L. \text{ mol}^{-1})$$

or as a dissociation constant, $K_d$:

$$K_d = \frac{k_d}{k_a} = \frac{[A][B]}{[AB]} \quad (\text{mol. } L^{-1})$$

$K_d$ is simply the inverse of $K_a$. More commonly in the literature $K_d$ is used as a measure of affinity. The strength of a binding interaction may be determined by the association constant $K_a$ or dissociation constant $K_d$. Alternatively, and particularly for comparison of the binding of different substances as in the examples of this invention, binding may be determined by measurement of a response related to the concentration of the complex (AB) at a fixed concentration of the reactants A and B. For example, binding may be measured by surface plasmon resonance (SPR) as the increase in SPR response following injection of a fixed concentration of one reactant (e.g. an antibody) over a surface to which is attached a fixed concentration of the other reactant (e.g. a Fc receptor). Or again, binding may be measured by an enzyme-linked immunosorbent assay (ELISA) as the absorbance given by enzymic conversion of a substrate (e.g. TMB) following a sequence of steps which may include for example: (a) adsorption of a reactant (e.g. antibody) to a microplate, (b) blocking non-specific binding sites, (c) incubation with a second reactant (e.g. C1q) labelled with an enzyme (e.g. horse-radish peroxidase).

Relative binding may be a ratio of binding measurements for a molecule of interest (for example a variant Fc region) binding to a target molecule (for example a Fc receptor) and a reference molecule (for example a wild-type reference, LALAPG reference, LALA reference) or buffer alone binding to the same target molecule under the same experimental conditions.

Charged amino acid residue. In the context of this invention, a "charged amino acid residue" is one of: aspartic acid (D), glutamic acid (E), histidine (H), lysine (K) or arginine (R). A negatively charged amino acid residue is either aspartic acid (D) or glutamic acid (E). A positively charged amino acid residue is either histidine (H), lysine (K) or arginine (R). A "net change in charged amino acid residues" as a consequence of amino acid substitutions or alterations is the absolute value of the difference between the net number of charged residues contained in a protein comprising a variant Fc region of this invention and the net number of charged residues contained its corresponding wild-type reference protein, wherein the net number of charged residues is the number of all the positively charged residues less the number of all the negatively charged residues.

Complement system. In the context of this invention, "complement system", otherwise known as "complement" refers to part of the innate immune system comprising a number of plasma proteins which may be recruited and activated by antibodies (or other proteins comprising an Fc region) to promote inflammation and attack the cell membrane of a target cell. The classical complement pathway is triggered by activation of the first component, the C1-complex. The C1-complex comprises three types of polypeptide chains, C1q, C1r and C1s. The Fc region of IgM or IgG antibodies binds to C1q to initiate the activation of C1r and C1s. A subsequent cascade of reactions can lead to the deposition of a membrane attack complex on the surface of the target cell.

Complement dependent cytotoxicity. Complement dependent cytotoxicity (CDC), also referred to as complement mediated cytotoxicity (CMC), is a mechanism of immune defence whereby a protein comprising an Fc region (including, for example, an antibody) bound to a target cell initiates the activation of the complement system, resulting in lysis of the target cell. CDC is mediated through the binding of an Fc region to C1q, resulting in activation of C1r and C1s, followed by a cascade of reactions which can lead to the deposition of a membrane attack complex on the surface of the target cell.

Composition. In the context of this invention a "composition" is a mixture which comprises both an active substance which is intended to have a pharmacological or physiological effect and an inactive substance which is not intended to have a pharmacological or physiological effect. The inactive substance may be helpful for providing a stable formulation of the active substance. A composition may be, for example, a drug product which comprises a drug substance.

Comprise. The term "comprise" means "include" as well as "consist of". For example, a composition "comprising" X and Y may consist exclusively of X and Y or may include something additional such as X+Y+Z.

Conjugate (noun). In the context of this invention a "conjugate" or a "conjugated protein" is a protein to which is covalently attached another substance. The other substance may itself comprise a protein or it may comprise any other kind of molecule or macromolecule. The other substance may be useful for various purposes, including for example: useful for treatment of a disease, useful for diagnosis of a disease, or useful for purification or analysis.

Consensus method. In the context of this invention, the term "consensus method" refers to the consensus method of the IEDB version 2.22 for determination of the binding of peptides to MHC Class II alleles as described by Wang 2008.

Constant region. The term "constant region" refers to immunoglobulin domains excluding variable domains. For example, a constant region may comprise the single constant domain of a light chain or three constant domains of IgA, IgD, or IgG heavy chain, or four constant domains of IgE or IgM heavy chain. A heavy chain constant region may include the flexible hinge region between the first and second constant domains. An IgA or IgM heavy chain constant region may include a J chain.

Culture medium. "Culture medium" is an aqueous mixture which is capable of supporting the growth of a cell.

Cytokine. A "cytokine" is a member of a large group of proteins which are secreted by cells and have a role in signalling between different cells. Many of them bind to receptors to modulate humoral or cellular immune responses and others are involved in a variety of ways in the growth and differentiation of numerous cell types. Cytokines include, for example, chemokines, interferons, interleukins, lymphokines, and tumour necrosis factors.

Cytokine release. In the context of this invention, the term "cytokine release" refers to the release of inflammatory cytokines from cells of the immune system which have been exposed to a protein comprising an Fc region. The inflammatory cytokines may include, for example, one or more of: GM-CSF, TNFα, IFNγ, IL-2, IL-4, IL-6, IL-8 and IL-10.

Domain A protein "domain" is a conserved part of a given protein sequence and tertiary structure that can evolve, function, and exist independently of the rest of the protein chain. Each domain forms a compact three-dimensional structure and often can be independently stable and folded. Many proteins consist of several structural domains. Antibodies commonly have several immunoglobulin domains in each polypeptide chain. Variable domains have a high degree of sequence variability and are responsible for binding to antigen. Constant domains are more highly conserved and are involved in the structural and functional integrity of the antibody.

Effector function. In the context of this invention "effector function" refers to any one or more physiological effects which may be mediated by an Fc region in vitro or in vivo. Such effects may include, for example, binding to C1q, activation of complement, complement-dependent cytotoxicity, binding to FcγRI, binding to FcγRII, binding to FcγRIII, antibody dependent cell-mediated cytotoxicity, antibody dependent cell-mediated phagocytosis or induction of cytokine release.

EU Index. The "EU index" or "EU index as in Kabat" or "EU numbering scheme" refers to the numbering of the EU myeloma protein (Edelman 1969; Kabat 1991).

Fc region. The term "Fc region" refers to the constant region of an immunoglobulin heavy chain excluding the first constant domain. For example, an Fc region may comprise the last two constant domains of IgA, IgD, or IgG heavy chain, or the last three constant domains of IgE and IgM. The Fc region may include the flexible hinge N-terminal to these domains. An IgA or IgM Fc region may include a J chain. Thus, an IgG Fc region typically comprises constant domains Cγ2 and Cγ3 and may also comprise the hinge between Cγ1 and Cγ2. Although the boundaries of the Fc region may vary, a human IgG Fc region with a hinge typically comprises residues E216 to its carboxyl-terminus. The human Cγ2 domain typically comprises residues A231 to K340. The human IgG Cγ3 domain typically comprises residues G341 to the carboxyl terminus. An Fc region may be monomeric, but is more commonly dimeric or multimeric.

Fc variant. The term "Fc variant" refers to a protein that comprises a variant Fc region. It may be an immunoglobulin comprising a variant Fc region or it may be a fusion protein where one of the protein components comprises a variant Fc region.

Fc receptor. An "Fc receptor" (FcR) is a protein found on the surface of certain types of cells, including for example, B lymphocytes, macrophages, natural killer cells, dendritic cells, neutrophils, basophils, eosinophils, platelets, which binds to the Fc region of immunoglobulins. There are several types of Fc receptor, classified according to the class of immunoglobulin which they bind to. For example, Fc-gamma receptors (FcγR) bind to IgG, Fc-epsilon receptors (FcεR) bind to IgE, and Fc-alpha receptors (FcαR) bind to IgA. There are various subtypes of FcγR in humans including for example, FcγRI (CD64), FcγRIIA (CD32A), FcγRIIB (CD32B), FcγRIIC (CD32C), FcγRIIIA (CD16A), FcγRIIIB (CD16B) with differing affinities and specificities for subclasses of IgG. Furthermore, there are various allelic forms and other variants. In addition to the FcγR, the neonatal Fc receptor (FcRn or Brambell receptor) is expressed on multiple cell types and is involved in transport of IgG, including across the placenta or in the mammary gland, as well as for control of IgG catabolism and homeostasis of IgG serum levels. Similar Fc receptors are found in other mammals, although the number and distribution of types, subtypes and alleles may differ according to the different species.

Fusion protein. A "fusion protein" (sometimes known as a chimeric protein) is a protein created through the joining of two or more genes that originally coded for separate proteins. Transcription and translation of this fusion gene results in single or multiple proteins with properties derived from each of the original proteins. Naturally occurring fusion proteins can be found in cancer cells. In the context of this invention, the term "fusion protein" is taken to mean a fusion protein created by genetic engineering, and which may include a gene or gene segment which is altered (compared with an original gene which coded for a separate protein). A fusion protein may comprise single or multiple proteins, any of which may be post-translationally modified.

Glycoform. A "glycoform" refers to any one of a number of different forms of a glycoprotein which differ with respect to the number, type or structure of the attached carbohydrates. Immunoglobulin Fc regions typically have carbohydrate attached to Asn297. Various structures of this carbohydrate give rise to different glycoforms of a protein comprising an Fc region. In the context of this invention a "spectrum of glycoforms" may be determined following release of the carbohydrates from a protein comprising an Fc region, followed by separation of the mixture of carbohydrates by a suitable chromatographic technique which resolves different structures and allows the comparison of different samples by graphical or numerical methods.

Heavy chain. The term "heavy chain" refers to a large protein subunit of an immunoglobulin. Heavy chains can be of any immunoglobulin isotype (for example IgG, IgE, IgM, IgD, IgA or IgY), subtype (for example IgG1, IgG2, IgG2a, IgG2b, IgG2c, IgG3, IgG4, IgA1 or IgA2) or allotype.

Host cell. A "host cell" is a cell which is capable of being transfected with nucleic acid to produce a cell which expresses the product of a gene comprised within the nucleic acid.

Immune Epitope Database. The "Immune Epitope Database" (IEDB) is a resource provided by the National Institute of Allergy and Infectious Disease which is available at the website of the Immune Epitope Database (Dhanda 2019). It catalogues experimental data on antibody and T cell epitopes studied in humans, and other animal species in the context of infectious disease, allergy, autoimmunity and transplantation. The IEDB also hosts tools to assist in the prediction and analysis of B cell and T cell epitopes, including peptides with a propensity to bind to MHC molecules.

Immunoglobulin. In the context of this invention "immunoglobulin" describes a molecule with one or more protein chains comprising at least one domain which can potentially bind to an antigen (the "antigen-binding domain") and at least one Fc region. The immunoglobulin may be of any isotype (for example IgG, IgE, IgM, IgD, IgA or IgY), subtype (for example IgG1, IgG2, IgG2a, IgG2b, IgG2c, IgG3, IgG4, IgA1 and IgA2) or allotype. The immunoglobulin may be of any species (for example human, monkey, camel, llama, goat, sheep, rabbit, mouse, rat, mouse, hamster or chicken) or it may be a hybrid derived from more than one species. The immunoglobulin may be a polyclonal immunoglobulin or a monoclonal immunoglobulin. It may be naturally occurring or may be created by genetic engineering (for example a chimeric antibody, humanised antibody, camelised antibody, intrabody).

Label. The term "label" refers to any organic or inorganic molecule or molecular complex which is capable of being covalently attached to a protein and is also capable of being detected by virtue of an intrinsic property which it possesses for example, colour, fluorescence, radioactivity, luminescence, catalytic activity, size, mass.

Light chain. The term "light chain" refers to a small protein subunit of an immunoglobulin. Light chains can be of any type (for example kappa or lambda), subtype or allotype.

Major Histocompatibility Complex. The "major histocompatibility complex" (MHC) is a set of genes that code for cell surface proteins essential for the vertebrate acquired immune system to recognize foreign molecules. The MHC gene family is divided into three subgroups: MHC class I, MHC class II, and MHC class III. MHC Class I molecules may be recognised by CD8 co-receptors while MHC Class II molecules may be recognised by CD4 co-receptors. Both comprise: (a) an alpha chain which binds an antigen-derived peptide and (b) a beta2 microglobulin chain. The combination of a peptide with a particular MHC molecule may be recognised by a T cell receptor and may potentially initiate immune functions of the T cell. In humans, the MHC molecules are also known as human leukocyte antigens (HLA). In the context of this invention, reference to "MHC" will be understood as reference to "human MHC" or "HLA", unless otherwise specified.

Nucleic acid. A nucleic acid is a biological macromolecule which comprises a linear strand of nucleotides linked by phosphodiester bonds. Nucleic acids include both deoxyribonucleic acid (DNA) and ribonucleic acid (RNA).

Pharmacokinetic parameters. Pharmacokinetics (PK) is a branch of pharmacology dedicated to determine the fate of substances administered to a living organism. It describes and measures the processes of absorption, distribution and elimination (i.e. metabolism and excretion). These processes can be modelled mathematically in a number of ways, including for example, compartmental and non-compartmental models. Various "pharmacokinetic parameters" (otherwise known as pharmacokinetic metrics) may be determined from an analysis of concentration (C) as a function of time (t) following the administration of a particular amount of drug (D). They include, for example, the following:

| Characteristic | Description | Symbol |
| --- | --- | --- |
| Maximum plasma concentration | Peak plasma concentration after drug administration | $C_{max}$ |
| Time of maximum concentration | Time to reach $C_{max}$ | $t_{max}$ |
| Volume of distribution | Apparent volume in which a drug is distributed | V |
| Area under the curve | The integral of the concentration-time curve over a defined period | $AUC_{0-t}$ $AUC_{0-\infty}$ |
| Elimination rate constant | The rate at which the drug is removed from the body (or the plasma) | k |
| Half life | The time required for the concentration of drug to reach half of its original value | $t_{1/2}$ |
| Clearance | The volume of plasma cleared of drug per unit time | CL |

Numerous pharmacokinetic parameters and methods for determining them are described in Rowland 1995.

Protein. A "protein" is a macromolecule which comprises one or more chains of amino acid residues linked together by peptide bonds. Proteins are typically produced by ribosomal translation of messenger RNA. They may additionally comprise any number of post-translational modifications. These may include, for example: lipidation, myristoylation, palmitoylation, isoprenylation, prenylation, farnesylation, geranylgeranylation, glypiation, lipoylation, attachment of flavin, attachment of heme, phosphopantetheinylation, Schiff base formation, acylation, acetylation, alkylation, amidation, amide bond formation, butyrylation, glycosylation, malonylation, hydroxylation, iodination, nucleotide addition, phosphorylation, adenylylation, uridylylation, proprionylation, formation of pyroglutamic acid, S-glutathionylation, S-nitrosylation, S-sulfenylation S-sulfinylation, S-sulfonylation, succinylation, sulfation, glycation, carbonylation, isopeptide bond formation, biotinylation, carbamylation, formation of disulfide bonds, pegylation.

Reference protein. In the context of this invention, a "reference protein" is a protein comprising an Fc region, with which a protein of this invention may be compared for one or more functional attributes, including for example, binding to a Fc receptor, binding to C1q, thermal stability, aggregation, glycosylation, immunogenicity, protease sensitivity. For example, a reference protein may be: (a) a protein comprising a human IgG1 Fc region with the amino acid sequence specified in SEQ ID NO: 1 ("wild-type reference" or "wild-type reference protein"), (b) a protein comprising a human IgG1 Fc region with the amino acid sequence specified in SEQ ID NO: 2 ("LALAPG reference" or "LALAPG reference protein") or (c) a protein comprising a human IgG1 Fc region with the amino acid sequence specified in SEQ ID NO: 3 ("LALA reference" or "LALA reference protein").

Significantly reduced. "Significantly reduced" in the context of this invention means reduced by a degree which has a probability of occurring by chance alone of less than 5%, as assessed by an appropriate statistical test.

Stability. In the context of this invention, "stability" refers to a lack of change in a measured property over a period of time.

Substantially reduced. "Substantially reduced" in the context of this invention means reduced by a considerable degree, for example reduced by 50%, 60%, 70%, 80%, 90%, 95%, 98%, 99% or 100%.

Surface plasmon resonance. "Surface plasmon resonance" (SPR) is the resonant oscillation of conduction electrons at the interface between negative and positive permittivity material stimulated by incident light. In the context of this invention, the term refers to a technique based on the principle of SPR for measuring non-covalent interactions between macromolecules such as proteins. There are numerous implementations of this technology including, for example, Biacore®.

Thermal stability. The term "thermal stability" refers to the ability of a substance, for example a protein, to resist an irreversible change in its chemical or physical structure at a high relative temperature. The thermal stability of a protein may be measured by determining the temperature at which an irreversible change occurs, for example unfolding, denaturation, aggregation or precipitation. Alternatively, it may be measured by determining the rate of such change which occurs at a particular temperature.

Variable region. The term "variable region" refers to one or more variable domains of immunoglobulin heavy or light chain(s). Although the boundaries of the variable domains may vary, human heavy chain variable domains usually comprise residues from the amino terminus to residue 117 and human light chain variable domains comprise residues from the amino terminus to R108 (kappa light chain) or G107a (lambda light chain).

Variant Fc region. The term "variant Fc region" refers to an Fc region that (a) has the same amino acid sequence as a naturally occurring Fc region except for amino acid alterations at one or more positions up to a maximum of twelve or (b) has the same amino acid sequence as any previously disclosed Fc region except for amino acid alterations at one or more of positions 234, 235 and 236 according to EU numbering.

Variant Cγ2 domain. The term "variant Cγ2 domain" refers to a Cγ2 domain that (a) has the same amino acid sequence as a naturally occurring Cγ2 domain except for amino acid alterations at one or more positions up to a maximum of twelve or (b) has the same amino acid sequence as any previously disclosed Cγ2 domain except for amino acid alterations at one or more of positions 234, 235 and 236 according to EU numbering.

Vector. In the context of this invention a "vector" is a polynucleotide used as a vehicle to artificially carry foreign genetic material into a cell, where it can be replicated and/or expressed. The cell may be a prokaryote but is preferably a eukaryote. The vector may be a plasmid, a viral vector, a cosmid or an artificial chromosome. A vector for expression of a protein in a eukaryotic host cell typically comprises: (a) sequences necessary for replication in bacteria including an origin of replication and an antibiotic resistance gene (for example for resistance to kanamycin or ampicillin), (b) sequences necessary for expression of the foreign genetic material in eukaryotic cells including a multicloning site for insertion of the foreign genetic material, at least one promoter sequence to drive expression of the foreign genetic material, a polyadenylation signal, a ribosome recognition site eg a Kozak sequence and optionally (c) a sequence coding for a marker selectable in eukaryotic cells, for resistance to an antibiotic such as G418, hygromycin or puromycin.

Applicability to Various IgG Fc Regions and Domains

Throughout this specification, for simplicity and clarity, reference is frequently made to variant Fc regions of human IgG1 antibodies which include one or more amino acid alterations at various positions (according to the EU numbering system). This is not intended to limit in any way the scope of the invention. Amino acid residues at the equivalent positions in other subclasses of human IgG, including IgG2, IgG3 and IgG4 or in any subclass of IgG from other species may be altered in the same way to produce the desired effects. Other species include, for example, birds and mammals, including, for example: primates, rodents, lagomorphs, carnivores, artiodactyls. Also included within the scope of this specification are naturally occurring allotypes of IgG as well as variants which comprise other mutations, for example those which might be introduced to modify binding to human FcRn or to improve other structural or functional properties, for example, stability or elimination of unwanted heterogeneity. Furthermore, the specification is not limited to variant Fc regions of intact antibodies, but also includes variant Fc regions comprised within any other proteins, for example: fusion proteins, immunoadhesins, immunocytokines, single chain antibodies, bispecific antibodies, multispecific antibodies, bispecific T-cell engagers, antibody-drug conjugates and enzyme replacement—Fc fusion proteins. In addition, this specification is not limited to variant Fc regions which are intact or complete but also includes variants comprising any part of an Fc region which would, in its wild-type form, be capable of binding to a Fcγ receptor, for example a Cγ2 domain or the combination of a hinge region and a Cγ2 domain. So, wherever the context allows, the term 'Fc region' should be understood to include not only an intact Fc region, but also any such part of an Fc region which would, in its wild-type form, be capable of binding to a Fcγ receptor.

Binding of Fc Regions to Fcγ Receptors

In many situations it is desirable to reduce, or preferably eliminate, the binding of IgG to Fcγ receptors, since the biological effects they mediate are unwanted, and may be harmful (e.g. see: Wang 2018). For example, when antibodies are being used to neutralize the activity of an antigen, concomitant activation of cellular responses may be undesirable. However, the Fc region has other useful properties, not least its ability to provide a long half-life by virtue of binding to FcRn. This feature is used in the development of fusion proteins where the Fc region imparts an extended half-life to other bioactive proteins. Nevertheless, activation of cellular responses may be undesirable. Therefore, researchers have developed variant forms of Fc having mutations which selectively reduce binding to FcγR.

Application of site-directed mutagenesis and X-ray crystallography of an Fc/FcγRIII complex has allowed the identification of amino acid residues in the Fc region which are involved in binding to Fc receptors. Many different residues have been identified, mutation of which may result in a decrease in binding to one or more of the Fc receptors. However, no single mutation has been found which completely eliminates FcγR binding, and therefore researchers have attempted to identify a combination of mutations (preferably as few as possible) which has that desirable effect. The sheer number of potential sites and the possibility to delete or convert them to any one of 19 alternative amino acid residues, means that the number of possible combinations of mutations is too vast to be exhaustively tested in practice. Nevertheless, certain combinations have been proposed to be able to 'completely abolish' immune effector functions (e.g. Schlothauer 2016). Surprisingly, we have now found that Fc variants comprising combinations of mutations which were formerly thought to be inert still have detectable binding activity. Therefore, there is a need for a minimal set of mutations that truly eliminates binding of human Fc to Fcγ receptors.

Amino Acid Alterations at a Single Site

Various investigators used site-directed mutagenesis to probe the role of individual amino acid residues in the binding of the human IgG1 Fc region to human FcγR. A non-exhaustive selection of results is summarised in Table 1.

TABLE 1

Examples of individual mutations in the Fc region of human IgG1 which have been said to result in reduced binding to FcγR. Amino acid residues are listed according to the single letter code and numbered according to the EU system. Variants are included if they were reported as giving reduced binding to all FcγR (Ref 1, Ref 2, Ref 3) or were reported as giving less than 50% binding to FcγRI, FcγRIIA and FcγRIIIA compared with the wild-type (Ref 4). Ref 1 WO2000042072, Table 6; Ref 2 Shields 2001, Table 1; Ref 3 US20060235208, paragraph 182; Ref 4 WO2006047350, FIG. 4.

| EU number | Wild-type | Variants showing reduced binding | | | |
|---|---|---|---|---|---|
| | | Ref 1 | Ref 2 | Ref 3 | Ref 4 |
| 225 | T | | | | K |
| 232 | P | | G | | |
| 233 | E | | P | | |
| 234 | L | | V | G, H | H, Q, T |
| 235 | L | | A | D, G, H | N, V |
| 236 | G | | Deleted | I, N, P, R | F, L, M, N, P, R |
| 237 | G | | | K, L, N, P | D, E, F, H, I, K, L, M, N, P, Q, R, S, T, V, W, Y |
| 238 | P | A | A | K | G, S, T |
| 239 | S | | | R | F, H, Y |
| 264 | V | | | | F, G, H |
| 265 | D | A | A | G | H, Y |
| 266 | V | | | | T |
| 267 | S | | | R | H |
| 269 | E | A | | R | F, G, H, I, K, L, M, N, P, R, S, T, V, W |
| 270 | D | A | | H | H, P, T |
| 271 | P | | | | V |
| 293 | E | | | | P |
| 295 | Q | | | | W |
| 296 | Y | | | | K |
| 297 | N | A | A | S | R |
| 299 | T | | | A, I, V | A, D, E, G, H, L, M, N, P, Q, R, V, W |
| 300 | Y | | | | R |
| 318 | E | | | | H |
| 325 | N | | | A, L | A, I, L, P |
| 327 | A | Q | Q | R | |
| 328 | L | | | R | |
| 329 | P | A | A | K | H, I, K, L, M, T |
| 330 | A | | | L, N, P, R, S | P |
| 331 | P | | | L | |
| 332 | I | | | | K, R |

Amino Acid Alterations at Multiple Sites

Thus, from the foregoing, there are at least 30 positions in the IgG1 Fc region where mutations can potentially reduce binding to FcγR. However, no one of them has been shown to completely eliminate binding to all of the receptors. In an effort to identify variants where binding is more effectively eliminated, researchers have tested combinations of mutations at different positions. For example, see: WO199958572, WO2006076594, WO2006047350, WO2006053301, WO2011066501, WO2013165690, WO2012130831, WO2014108483, US20060235208, U.S. Pat. Nos. 6,194,551, 8,969,526, U.S. Ser. No. 10/011,660; Xu 2000; Hezarah 2001, Shields 2001, Lin 2013; Dall'Acqua 2006, Oganesyan 2008, Schlothauer 2016, Tam 2017.

The potential number of combinations even of the identified mutations (Table 1) is extremely large (approximately $5 \times 10^{17}$). Clearly, it is completely impractical to manufacture and test all of them, let alone the vast number of combinations of alternative substitutions which might be made at each site. In practice, a much smaller number of combinations has been tested. A few of these have been used in therapeutic antibodies entering clinical trials as exemplified in Table 2.

TABLE 2

Examples of therapeutic IgG1 antibodies which include combinations of mutations in the Fc region that may reduce binding to FcγRs and/or C1q. Data were obtained from the antibody sequences reported in the WHO lists of recommended international proprietary names, WHO Drug Information volumes 16 to 33 (2002 to 2019).

| INN | Mutations in the Fc region |
|---|---|
| abelacimab | D265A, P329A |
| anifrolumab | L234F, L235E, P331S |
| anrukinzumab | L234A, G237A |
| bimagrumab | L234A, L235A |
| cemiplimab | L234A, L235A |
| cergutuzumab | L234A, L235A, P329G, Y349C, T366S, L368A, Y407V |
| crovalimab | L235R, G236R, S239K, A327G, A330S, P331S, M428L, N434A, Q438R, S440E |
| durvalumab | L234F, L235E, P331S |
| foralumab | L234A, L235E |
| lodelcizumab | L234A, L235A |
| olendalizumab | L234F, L235E, P331S |
| perakizumab | L234A, L235A |
| prolgolimab | L234A, L235A |
| refanezumab | L234A, L235A |
| risankizumab | L234A, L235A |
| spesolimab | L234A, L235A |
| teplizumab | L234A, L235A |
| tesidolumab | L234A, L235A |
| vedolizumab | L235A, G237A |

Binding of Fc Regions to FcRn

The neonatal Fc receptor (FcRn) is widely expressed in epithelial cells where it is responsible for mediating transport and recycling of IgG (Kuo 2011). FcRn-mediated transport of IgG begins with fluid phase pinocytosis of IgG at the cell membrane and binding to FcRn occurs under the acidic conditions of the endosome. From there it may be transcytosed to the opposite membrane surface (e.g. for transport across the placenta) or recycled back to the original membrane surface. As a result of the activity of FcRn, IgG has a much longer half-life than it otherwise would. This is a distinct advantage for the use of therapeutics which comprise an Fc region and it is desirable that any modifications which reduce the ability of IgG to bind to the Fcγ receptors (or to C1q), do not adversely affect binding to FcRn. Indeed, a number of investigators have sought to enhance binding to FcRn with the aim of increasing the half-life of the drug (e.g. Dall'Acqua 2006; Zalevsky 2010). Because the binding site for FcRn is located in the CH2-CH3 domain, distinct from the binding site for Fcγ receptors and for C1q, it is possible to identify different amino acid alterations which affect the binding of one type of receptor but not the other.

Measurement of Binding to Fc Receptors

Various different techniques have been used to measure binding of variant immunoglobulins to Fc receptors, including FcγR and FcRn. They include: Enzyme-linked immunoassay (ELISA) using soluble recombinant Fc receptors (e.g. WO2000042072; Shields 2001), flow cytometry using mammalian cells transfected with genes encoding Fc receptors (e.g. WO2000042072; Shields 2001), AlphaScreen® (a bead-based luminescent proximity assay) using tagged soluble recombinant Fc receptors (e.g. US20060235208; WO2006047350, WO2011066501), multiplex microsphere (Luminex®) assay (e.g. Boesch), surface plasmon resonance using a Proteon® system with soluble recombinant Fc receptors (e.g. WO2013165690), surface plasmon resonance using a Biacore® system with soluble recombinant Fc receptors (e.g. WO2011066501, WO2012130831; Schlothauer 2016). Other experimental techniques, and other implementations of the foresaid techniques are also known in the art. The variety of different experimental techniques, experimental conditions and diverse preparations of variant immunoglobulins and Fc receptors makes it difficult or impossible to reliably compare results from different studies in order to determine whether one particular combination of mutations is actually more effective than another for the purpose of silencing binding to the FcγR.

Binding of Fc Regions to C1q

Complement component 1q (C1q) is a protein complex comprised of six copies each of three protein chains, assembled into globular heads attached to a stalk. It binds to antibodies to initiate the cascade of reactions that results in activation of the complement system.

Amino Acid Alterations at a Single Site

Various investigators have used site-directed mutagenesis to probe the role of individual amino acid residues in the binding of the human IgG1 Fc region to human C1q. A non-exhaustive selection of results is summarised in Table 3. have tested combinations of mutations at different positions. For example, see: Borrok 2017; Lin 2013; Vafa 2014; Schlothauer 2016.

The potential number of combinations even of the identified mutations (Table 3) is substantial (approximately 276480). Clearly, it is completely impractical to manufacture and test all of them, let alone the vast number of combinations of alternative substitutions which might be made at each site or the even larger number of combinations of substitutions which might impact both on binding of C1q and binding of FcγR. In practice, only a small number of combinations has been tested. A few of these have been used in therapeutic antibodies entering clinical trials as exemplified in Table 2.

Measurement of Binding to C1q

Various different techniques have been used to measure binding of variant immunoglobulins to C1q. They include: Enzyme-linked immunoassay (ELISA) (e.g. Hezarah 2001; Dall'Acqua 2006; Oganesyan 2008; Schlothauer 2016), Flow cytometry (e.g. Kanda 2006), Multiplex microsphere (Luminex) assay (e.g. Boesch 2014), Surface plasmon resonance (e.g. Borrock 2017; Dall'Acqua 2006; Moore 2010). Other experimental techniques, and other implementations of the foresaid techniques are also known in the art. The variety of different experimental techniques, experimental conditions and diverse preparations of variant immunoglobulins and Fc receptors makes it impossible to reliably compare results from different studies in order to determine whether one particular combination of mutations is actually more effective than another for the purpose of silencing binding to C1q.

Variant Fc Regions with Reduced Binding to Human FcγR and Human C1q

Comparison of Fc Variants

It is impossible to reliably compare results from different published studies in order to determine whether one par-

TABLE 3

Examples of individual mutations in the Fc region of human IgG1 which have been said to result in reduced binding to C1q. Amino acid residues are listed according to the single letter code and numbered according to the EU system. Variants are included if they were reported as giving reduced binding to C1q. Ref 1 Michaelsen 2009; Ref 2 Idusogie 2000; Ref 3 Moore 2010; Ref 4 Lazar 2006; Ref 5 US6737056B1; Ref 6 Lund 1996.

|  |  | Variants showing reduced binding | | | | | |
| --- | --- | --- | --- | --- | --- | --- | --- |
| EU number | Wild-type | Ref 1 | Ref 2 | Ref 3 | Ref 4 | Ref 5 | Ref 6 |
| 234 | L | A | | | | | |
| 235 | L | A | | | | | |
| 241 | F | | | | | | A |
| 264 | V | | | | | | A |
| 265 | D | | A | | | | |
| 268 | H | | | G | | | |
| 270 | D | A | A, L, V | H | | K, V | |
| 272 | E | | | R | | | |
| 295 | Q | | | G | | | |
| 322 | K | A | A, E, L, M, N | | | A | |
| 325 | N | | | L | | | |
| 328 | L | | | M | | | |
| 329 | P | A | A, G | | | A | |
| 330 | A | | | | L | | |
| 331 | P | G | A | D, L | | A | |

Amino Acid Alterations at Multiple Sites

Thus, from the foregoing, there are at least 14 positions in the IgG1 Fc region where mutations can reduce binding to C1q. However, no one of them has been shown to completely eliminate binding. In an effort to identify variants where binding is more effectively eliminated, researchers ticular combination of mutations is actually more effective than another for the purpose of silencing binding to FcγR or C1q. Therefore, as described in Example 1, we prepared a set of variant immunoglobulins representing variants known in the art but all based on the same IgG1 antibody (Table 4). Binding to human FcγR was measured by surface plasmon resonance as described in Example 2. Surprisingly, all of the previously known variants gave a measurable degree of binding to human FcγRI with responses significantly above background (Table 8), even those where binding to FcγR was previously described as "fully ablated . . . reduced to an undetectable level" (WO2013165690), "completely inert" (WO2014108483), "completely abolished" (Schlothauer 2016; Hezarah 2001), "silent" (Tam 2017) or "no detectable binding" (Vafa 2014). Furthermore, as shown in Example 6, several of the previously known variants, including L234A/L235A, L234F/L235E/P331S and L234F/L235Q/K322Q also gave responses significantly above background in ADCC and ADCP assays (Table 20 and Table 21).

TABLE 4

List of variant immunoglobulin Fc regions. Each variant was constructed using the same immunoglobulin light chain and IgG1 heavy chain with the mutations indicated. Exemplary antibodies can be found in Table 2 or in the following references: (1) Lin 2013; (2) Tam 2017; (3) Armour 1999; (4) Horton 2011. (5) Bolt 1993.

| Sample | Mutations in the Fc region | Exemplar | Reference |
| --- | --- | --- | --- |
| 2-65 | L234A, L235A (LALA) | bimagrumab | WO1988007089 |
| 2-66 | L234A, L235A, P329G (LALAPG) | cergutuzumab | WO2012130831 |
| 2-67 | N297Q (aglycosyl) | otelixizumab (5) | Bolt 1993 |
| 2-68 | G236R, L328R | XENP6187 (4) | US20060235208 |
| 2-69 | L234A, G237A | anrukinzumab | US2009060906 |
| 2-71 | L234A, L235E | foralumab | WO2018044948 |
| 2-73 | D265A, P329A | abelacimab | WO2016207858 |
| 2-74 | L234A, L235A, K322A | farletuzumab variant (1) | Lin 2013 |
| 2-75 | L234F, L235E, P331S | durvalumab | WO2009100309 |
| 2-76 | L234F, L235Q, K322Q | L3 | WO2013165690 |
| 2-77 | L234A, L235A, G237A, P238S, H268A, A330S, P331S | Ab1 (anti-TNFα) (2) | WO2011066501 |
| 2-78 | E233P, L234V, L235A, G236⊗, A327G, A330S, P331S | Campath variant (3) | WO1999058572 |

Characterisation of New Fc Variants

We now prepared a novel set of Fc variants, as described in Example 1 and compared them to known variants. The results enable us to identify a small number of amino acid residues wherein amino acid substitutions can be combined to give variant Fc regions which have significantly lower levels of binding to human FcγRI than known variants. We have identified variant Fc regions which comprise two or three amino acid substitutions that substantially reduce or completely abolish detectable binding to human Fcγ receptors as measured using surface plasmon resonance (e.g. see Example 2) or by cell-based assay for ADCC or ADCP (e.g. see Example 6). In most instances, the same amino acid substitutions also substantially reduce or completely abolish detectable binding to human C1q as measured using ELISA (e.g. see Example 4). In some of the experimental tests to be described, a protein comprising a variant Fc region comprising amino acid substitutions is to be compared with a blank sample containing buffer alone. In other tests, a protein comprising a variant Fc region comprising amino acid substitutions is to be compared with a reference protein. In such case the proteins to be compared are manufactured using essentially the same cell line and essentially the same culture conditions and are purified in essentially the same way in order that the results of comparative tests may be valid. Preferably, any component parts of the test proteins and the reference protein other than the Fc region are essentially identical. For example, if the test proteins are antibodies, then both the test proteins and the reference proteins preferably have the same variable regions. Depending on the purpose of the test, the reference protein may comprise a naturally-occurring (wild-type) Fc region (e.g. SEQ ID NO: 1), or it may comprise a variant Fc region with amino acid alterations corresponding to a previously-described Fc variant, preferably L234A/L235A/P329G (LA-LAPG) (e.g. SEQ ID NO: 2).

Binding of the new variants to human FcRn, as measured by surface plasmon resonance, is not substantially reduced compared with the binding of a wild-type reference protein (e.g. see Example 3). Furthermore, the thermal stability of the new variants, as measured by size exclusion chromatography after incubation for up to 14 days at 40° C. (e.g. see Example 7) or by differential scanning fluorimetry (e.g. see Example 8, Example 12) or by light scattering (e.g. see Example 12) is not substantially reduced compared with the thermal stability of a wild-type reference protein.

Proteins Comprising a Variant Fc Region with Significantly Reduced Binding Activity Accordingly, in some aspects a protein is provided which comprises a variant Fc region comprising:
  a) an amino acid substitution at position 234 or an amino acid substitution at position 235 or amino acid substitutions at both positions 234 and 235 and
  b) an amino acid alteration to arginine (R) at position 236
wherein the binding of the protein to human FcγRI is significantly reduced compared with the binding of a reference protein and wherein the reference protein comprises a variant human IgG1 Fc region comprising the amino acid substitutions L234A, L235A and P329G.

An 'amino acid alteration' at position 236 means either an amino acid substitution (e.g. for a Fc region from human IgG1, IgG3, IgG4) or an amino acid insertion (e.g. for a Fc region from human IgG2).

In some embodiments, a protein is provided which comprises a variant Fc region comprising:
  a) an amino acid substitution at position 234 or amino acid substitutions at both positions 234 and 235; and
  b) an amino acid alteration to arginine (R) at position 236
wherein the binding of the protein to human FcγRI is significantly reduced compared with the binding of a reference protein and wherein the reference protein comprises a variant human IgG1 Fc region comprising the amino acid substitutions L234A, L235A and P329G.

In all of the following embodiments of the above aspects, the protein comprising a variant Fc region comprises an amino acid alteration to arginine (R) at position 236 and the binding of the protein to human FcγRI is significantly reduced compared with the binding of the said reference protein.

In some embodiments the amino acid at position 234 is substituted to any one of A, D, E, G, H, K, Q, R, S or T. In some embodiments the amino acid at position 235 is substituted to any one of A, D, E, G, H, I, K, Q, S, T or V.

In some embodiments the amino acid at position 234 is substituted to any one of A, D, E, G, H, K, Q, R, S or T and the amino acid at position 235 is substituted to any one of A, D, E, G, H, I, K, Q, R, S, T or V.

Some amino acid substitutions or alterations result in charge changes. For example, substitution of an uncharged residue (e.g. A, F, G, L) with a negatively charged residue (e.g. D, E) results in a net increase in negative charge. Conversely, substitution with a positively charged residue (e.g. H, K, R) results in a net increase in positive charge. Substitution at one site with a negatively charged residue and at another with a positively charged residue will result in no change in the net number of charged residues. Other combinations will be apparent to a person skilled in the art. Changes in the net number of charged residues affects the isoelectric point of a protein and this may have adverse effects on its manufacturability, stability, solubility, half-life in vivo or on other physicochemical or biological properties. It is desirable that such changes should be minimised. Therefore, in some embodiments of this invention, the net change in charged amino acid residues as a consequence of amino acid substitutions and alterations at any of positions 234, 235 and 236 is no more than one. For example, in some embodiments, amino acid alterations at position 234, 235 and 236 may be selected from: 0/0/+, 0/−/+, −/0/+, −/−/+, −/+ or +/−/+, where "0" indicates either no change or substitution with an uncharged amino acid, "−" indicates substitution with a negatively charged amino acid and "+" indicates substitution with a positively charged amino acid. Embodiments which are less desirable, because they would change the net number of charged residues by 2 or 3, include 0/+/+, +/0/+ and +/+/+. In some embodiments, any substitution to a positively charged amino acid at position 234 or 235 is avoided.

In some embodiments, a protein is provided which comprises a variant Fc region, wherein the variant Fc region comprises: (a) an amino acid substitution at position 234 or an amino acid substitution at position 235 or amino acid substitutions at both positions 234 and 235; and (b) an amino acid alteration to arginine (R) at position 236, wherein the amino acid numbering is according to the EU index as in Kabat, and wherein the binding of the protein to human FcγRI is significantly reduced compared with the binding of a LALAPG reference protein and wherein the net change in charged amino acid residues as a consequence of the said amino acid substitutions and alteration is no more than one.

In some embodiments, the amino acid at position 234 is substituted to any one of H, K or R and the amino acid at position 235 is substituted to one of D or E, or the amino acid at position 234 is substituted to one of D or E and the amino acid at position 235 is substituted to any one H, K or R. In some embodiments, the amino acid at position 234 is substituted to any one of A, D, E, G, Q, S or T. In some embodiments the amino acid at position 235 is substituted to any one of A, D, E, G, I, Q, S, T or V.

In some embodiments, the amino acid at position 234 is unaltered and the amino acid at position 235 is substituted to any one of E, Q, S or T.

In some embodiments, the binding of the protein comprising a variant Fc region to human FcγRI is less than 50%, preferably less than 40%, less than 30%, less than 20%, less than 10% or less than 5% of the binding of a reference protein comprising a variant human IgG1 Fc region comprising the amino acid substitutions L234A, L235A and P329G. Binding of the protein to human FcγRI may be measured by any suitable method that is sufficiently sensitive to detect small differences in binding. Preferably, binding is measured by surface plasmon resonance, for example as described in Example 2. In some embodiments, the protein comprising a variant Fc region has a binding response to human FcγRI, when measured by surface plasmon resonance, of less than 40 response units (RU), preferably less than 30 RU, less than 20 RU, less than 10 RU, or less than 5 RU, as measured by surface plasmon resonance under conditions where the comparable wild-type protein gives a binding response of greater than 2000 RU or a reference protein comprising a variant human IgG1 Fc region comprising the amino acid substitutions L234A, L235A and P329G gives a binding response of greater than 40 RU.

In some embodiments, a protein is provided which comprises a variant Fc of a wild-type human IgG1 Fc region comprising:
a) an amino acid substitution at position 234 or an amino acid substitution at position 235 or amino acid substitutions at both positions 234 and 235 and
b) an amino acid substitution to arginine (R) at position 236 wherein the binding of the protein to human FcγRI is significantly reduced compared with the binding of a reference protein and wherein the reference protein comprises a variant human IgG1 Fc region comprising the amino acid substitutions L234A, L235A and P329G.

In some embodiments, a protein is provided which comprises a variant Fc of a wild-type human IgG1 Fc region comprising:
a) an amino acid substitution at position 234 or amino acid substitutions at both positions 234 and 235 and
b) an amino acid substitution to arginine (R) at position 236 wherein the binding of the protein to human FcγRI is significantly reduced compared with the binding of a reference protein and wherein the reference protein comprises a variant human IgG1 Fc region comprising the amino acid substitutions L234A, L235A and P329G.

In some embodiments, a protein is provided which comprises a variant Fc region, wherein the variant Fc region comprises: (a) an amino acid substitution at position 234 or an amino acid substitution at position 235 or amino acid substitutions at both positions 234 and 235; and (b) an amino acid alteration to arginine (R) at position 236, wherein the amino acid numbering is according to the EU index as in Kabat, and wherein the binding of the protein to human FcγRI is significantly reduced compared with the binding of a LALAPG reference protein and wherein the net change in charged amino acid residues as a consequence of the said amino acid substitutions and alteration is no more than one.

In some embodiments, the binding of the protein to human C1q is effectively undetectable (that is, not significantly greater than the binding of a sample of buffer alone). In some embodiments, the binding of the protein to human C1q is substantially reduced compared to a comparable wild-type reference protein. In some embodiments, the binding of the protein to human C1q is less than 20%, preferably less than 10%, less than 5%, less than 2% or less than 1% of the binding of a wild-type reference protein. In some embodiments, the binding of the protein to human C1q is not significantly different from the binding of a LALAPG reference protein. Binding of the protein to human C1q may be measured by any suitable method that is sufficiently sensitive to detect small differences in binding. Preferably binding is measured by ELISA, for example as described in Example 4. In some embodiments, the protein comprising a variant Fc region has a specific binding response to human C1q measured by ELISA of less than 0.1 absorbance units (AU), preferably less than 0.05 AU, less than 0.02 AU, less than 0.01 AU, or less than 0.015 AU, as measured by ELISA under conditions where the comparable wild-type protein gives a specific binding response of greater than 1.0 AU, wherein a 'specific binding response' is the binding response of a test sample less the binding response of buffer alone.

In some embodiments, the protein comprising a variant Fc region retains binding to human FcRn and in some embodiments the binding to FcRn is reduced by no more than 50%, 40%, 30%, 20%, 10% or 5% compared with a wild-type reference protein. In some embodiments, there is no significant difference between the binding of the protein comprising a variant Fc region to human FcRn and the binding of a wild-type reference protein. In some embodiments, the protein comprising a variant Fc region has greater binding activity to human FcRn than a wild-type reference protein. Binding of the protein to human FcRn may be measured by any suitable method that is sufficiently sensitive to detect differences in binding including, for example, by surface plasmon resonance as described in Example 3 or by a NanoBiT® competition immunoassay as described in Example 3.

Proteins Comprising a Variant Fc Region with Substantially Reduced ADCC

In some embodiments, the protein comprising a variant Fc region exhibits a substantially reduced ADCC activity compared with the corresponding wild-type reference protein. In some embodiments, the ADCC activity of the protein comprising a variant Fc region is less than 20%, preferably less than 10%, less than 5%, less than 2% or less than 1% of the ADCC activity of the corresponding wild-type reference protein. In some embodiments the ADCC activity of the protein comprising a variant Fc region is not significantly different from the ADCC activity of assay buffer. In some embodiments, the protein comprising a variant Fc region has no detectable ADCC activity at concentrations up to 10 µg/mL. In some embodiments, the ADCC activity of the protein comprising a variant Fc region is not significantly different from the ADCC activity of a LALAPG reference protein comprising the amino acid substitutions L234A, L235A and P329G. In some embodiments, the ADCC activity of the protein comprising a variant Fc region is significantly less than the ADCC activity of a reference protein comprising the amino acid substitutions L234A and L235A. In some embodiments, the ADCC activity of the protein comprising a variant Fc region is less than 50%, preferably less than 20%, less than 10%, less than 5%, less than 2% or less than 1% of the ADCC activity of a reference protein comprising the amino acid substitutions L234A and L235A. ADCC activity may be measured by any suitable method that is sufficiently sensitive to detect differences in activity, for example, by a cell-based luminescence assay as described in Example 6.

Proteins Comprising a Variant Fc Region with Substantially Reduced ADCP

In some embodiments, the protein comprising a variant Fc region exhibits a substantially reduced ADCP activity compared with the corresponding wild-type reference protein. In some embodiments, the ADCP activity of the protein comprising a variant Fc region is less than 20%, preferably less than 10%, less than 5%, less than 2% or less than 1% of the ADCP activity of the corresponding wild-type reference protein. In some embodiments the ADCP activity of the protein comprising a variant Fc region is not significantly different from the ADCP activity of assay buffer. In some embodiments, the protein comprising a variant Fc region has no detectable ADCP activity at concentrations up to 10 µg/mL. In some embodiments, the ADCP activity of the protein comprising a variant Fc region is not significantly different from the ADCP activity of a reference protein comprising the amino acid substitutions L234A, L235A and P329G. In some embodiments, the ADCP activity of the protein comprising a variant Fc region is significantly less than the ADCP activity of a reference protein comprising the amino acid substitutions L234A and L235A. In some embodiments, the ADCP activity of the protein comprising a variant Fc region is less than 50%, preferably less than 20%, less than 10%, less than 5%, less than 2% or less than 1% of the ADCP activity of a reference protein comprising the amino acid substitutions L234A and L235A. ADCP activity may be measured by any suitable method that is sufficiently sensitive to detect differences in activity for example, by a cell-based luminescence assay as described in Example 6.

Proteins Comprising a Variant Fc Region with Substantially Reduced CDC

In some embodiments, the protein comprising a variant Fc region exhibits a substantially reduced CDC activity compared with the corresponding wild-type reference protein. In some embodiments, the CDC activity of the protein comprising a variant Fc region is less than 20%, preferably less than 10%, less than 5%, less than 2% or less than 1% of the CDC activity of the corresponding wild-type reference protein. In some embodiments the CDC activity of the protein comprising a variant Fc region is not significantly different from the CDC activity of assay buffer. In some embodiments, the protein comprising a variant Fc region has no detectable CDC activity at concentrations up to 10 µg/mL. In some embodiments, the CDC activity of the protein comprising a variant Fc region is not significantly different from the CDC activity of a reference protein comprising the amino acid substitutions L234A, L235A and P329G. CDC activity may be measured by any suitable method that is sufficiently sensitive to detect differences in activity for example, by a 51Cr release assay (e.g. Hale 1983) or by a luminescence assay (e.g. Niles 2007).

Proteins Comprising a Variant Fc Region with Substantially Reduced Toxicity

Certain proteins comprising Fc regions, notably certain monoclonal antibodies (for example muromonab, alemtuzumab, theralizumab) are known to induce toxicological effects in humans which are associated with the release of inflammatory cytokines (for example gamma-interferon, tumour necrosis factor, interleukin-6). Such toxicological effects (sometimes called "cytokine storm") may often be caused by, or exacerbated by the binding of Fc regions to Fcγ receptors. Various in vitro assays are known in the art, which are (to a greater or lesser extent) predictive of such toxicological effects (e.g. Finco 2014; Grimaldi 2016; Vessilier 2015). For example, in the so-called "whole blood" assay, a test sample is incubated with unfractionated blood (preferably anticoagulated with heparin) and the release of inflammatory cytokines is measured (e.g. Wing 1995; Wolf 2012). Alternatively, a test sample may be incubated with peripheral blood mononuclear cells (PBMC) and the release of inflammatory cytokines is measured (e.g. Vessilier 2015). Inflammatory cytokines may include some or all of: GM-CSF, IFNγ, IL-2, IL-4, IL-6, IL-8, IL-10, TNFα or other cytokines know to be associated with an inflammatory response. In some assays, the test sample may be immobilised, for example by binding to a microplate (e.g. Findlay 2010) or on epithelial cells (e.g. Findlay 2011). In others assays, sensitivity may be increased by preculture of PBMC at high density (e.g. Romer 2011). Cytokine-release activity may be measured by determining the concentrations of one or more cytokines in the culture supernatant of cells exposed to the test samples for periods between 1 hour and 72 hours. Cytokine-release activity may be measured using a single donor, or more than one donor, or may be an average of any number of donors. In some embodiments, the protein comprising a variant Fc region exhibits a substantially reduced cytokine-release activity compared with the wild-type reference protein. In some embodiments, the cytokine-release activity of the protein comprising a variant Fc region is less than 20%, preferably less than 10%, less than 5%, less than 2% or less than 1% of the cytokine-release activity of the corresponding wild-type reference protein. In some embodiments the cytokine-release activity of the protein comprising a variant Fc region is less than or not significantly different from the cytokine release activity of diluent. In some embodiments, the cytokine-release activity of the protein comprising a variant Fc region is not significantly different from the cytokine-release activity of a LALAPG reference protein. Cytokine release activity may be measured by any suitable method that is sufficiently sensitive to detect differences in activity, for example as described in Example 9.

Proteins Comprising a Variant Fc Region with Minimal Immunogenicity

Critical steps in immune responses to proteins include proteolytic processing and binding of peptides to major histocompatibility complex (MHC) Class II for presentation on the surface of antigen-presenting cells. Such peptide-MHC complexes may be recognized by specific receptors on CD4+ T cells, resulting in activation of the T cells to provide help for antibody responses by B cells. The propensity to create new peptides with a high likelihood of binding to MHC Class II may be determined by various method, including both "in silico" methods (e.g. Jensen 2018; Nielson 2007; Sidney 2008; Sturniolo 1999; Bryson 2010; Jawa 2013; King 2014) or "in vitro" methods (e.g. Brinks 2013; Jawa, 2013; Joubert 2016)

In some embodiments, the protein comprising a variant Fc region comprises amino acid substitutions which do not have a propensity to create new peptides with a high likelihood of binding to human MHC Class II as determined by an "in silico" method. In some embodiments the protein comprising a variant Fc region does not contain any new peptides (compared with a wild-type reference protein) with a rank score of ≤ 10% when assessed using the IEDB MHC-II Binding Predictions tool (Fleri 2017). An example is provided in Example 5. Amino acid substitutions which create new peptides with a higher likelihood of binding to human MHC Class II include: L234F, L234I, L234M, L234W, L234Y, L235F, L235W and L235Y (see Table 19). In some embodiments the protein comprises amino acid substitutions at residue 234 which do not include phenylalanine (F), isoleucine (I), methionine (M), tryptophan (W) or tyrosine (Y). In some embodiments the protein comprises amino acid substitutions at residue 235 which do not include phenylalanine (F), tryptophan (W) or tyrosine (Y). In some embodiments the protein comprises amino acid substitutions which do not include any of the above substitutions.

In some embodiments, the protein comprises amino acid substitutions which do not have a propensity to create new peptides with a high likelihood of being presented on the surface of human antigen-presenting cells (for example, dendritic cells). The propensity to create new peptides with a high likelihood of being presented on the surface of human antigen-presenting cells may be determined by any suitable method (e.g. Brinks 2013; Jawa 2013; Joubert 2016). An example is provided in Example 13. Surprisingly, a peptide having only the amino acid substitution G236R was found to have an increased risk of immunogenicity compared with the corresponding wild-type peptide, whereas the addition of additional substitutions at positions 234 and 235 decreased this risk to no more than that of the corresponding wild-type peptide.

In some embodiments the protein comprising a variant Fc region has significantly reduced immunogenicity in vivo when compared with a corresponding wild-type reference protein. Immunogenicity in vivo may be measured by any suitable method known in the art. For example, subjects, such as mice, rats, rabbits, non-human primates or humans, may be immunised with one or more doses of the test samples. After a suitable period (e.g. 7 to 28 days) following immunisation, cellular and/or humoral immune responses may be measured (e.g. Chen 2007; Loureiro 2011). Preferably, a sufficient number of subjects (e.g. five or more) are immunised with each test substance so that statistical comparisons can be made of the measured immune responses between groups immunised with different proteins.

Proteins Comprising a Variant Fc Region Having Unaltered Glycosylation

Immunoglobulin Fc regions expressed by mammalian cells are normally glycosylated at N297 and exhibit a spectrum of different glycoforms which is characteristic of the manufacturing process, and especially the choice of host cell and the cell culture conditions (e.g. Jefferis 2005; Costa 2014; Werner 2007). There are many methods known in the art for characterising the spectrum of glycoforms exhibited by proteins which comprise an Fc region (for example see Reutsch 2015a; Reutsch 2015b). In some embodiments, the spectrum of glycoforms exhibited by the protein comprising a variant Fc region is indistinguishable from the spectrum of glycoforms exhibited by the corresponding wild-type reference protein. In some embodiments, the spectrum of glycoforms exhibited by the protein comprising a variant Fc region is not significantly different from the spectrum of glycoforms exhibited by the corresponding wild-type reference protein. In some embodiments, the spectrum of glycoforms exhibited by the protein comprising a variant Fc region is not substantially different from the spectrum of glycoforms exhibited by the corresponding wild-type reference protein. In each case the proteins to be compared are manufactured using essentially the same cell line and essentially the same culture conditions and are purified in essentially the same way. Examples are provided in Example 11.

Proteins Comprising a Variant Fc Region being Homogeneous and Stable During Manufacture and Storage It is desirable that proteins to be used in the manufacture of medicinal products should be homogeneous and stable for extended periods of time. Certain amino acid residues, including asparagine (N), cysteine (C), methionine (M), are potentially subject to post-translational modifications such as deamidation of asparagine or oxidation of cysteine or methionine and this may lead to undesirable heterogeneity or instability. Motifs which are particularly liable to deamidation include NG, NS, NH and QG. Other amino acid substitutions, namely glycine (G) and proline (P) may destabilise the protein backbone and potentially disrupt the three-dimensional structure. Motifs which are liable to isomerization of aspartic acid include DG, DP and DS. Motifs which are liable to peptide bond cleavage include TS, KK, RK and KR. In some embodiments, the protein comprises amino acid substitutions which do not include asparagine (N), cysteine (C) or methionine (M). In some embodiments, the protein comprises amino acid substitutions which do not include glycine (G) or proline (P). In some embodiments, the protein comprises amino acid substitutions which do not create two-amino acid motifs including NG, NS, NH, QG, DG, DP, DS, TS, KK, RK or KR.

Various amino acid substitutions may increase heterogeneity or instability by increasing the tendency of the protein to unfold or to form a less ordered form. Such a tendency may be determined by various techniques known in the art, including measuring the thermal stability of the protein, for example using differential scanning calorimetry (DSC), differential scanning fluorimetry (DSF), circular dichroism (CD), differential static light scattering (DSLS), isothermal denaturation (ITD) or thermal challenge assay (e.g. see Senisterra 2009). Examples are provided in Example 8 and Example 12. Other techniques which may be particularly suitable for rapid measurement of small quantities of samples include affinity-capture self-interaction nanoparticle spectroscopy (AC-SINS), clone self-interaction by biolayer interferometry (CSI-BLI), hydrophobic interaction chromatography (HIC), salt-gradient affinity-capture self-interaction nanoparticle spectroscopy (SGAC-SINS) and standup monolayer adsorption chromatography (e.g. Jain 2017 and references therein).

In some embodiments, the thermal stability of the protein comprising a variant Fc region is not significantly different from the thermal stability of the equivalent wild-type reference protein. In some embodiments, the thermal stability of the protein comprising a variant Fc region is within ±3°C, within ±2° C., or within ±1° C. of the thermal stability of the equivalent wild-type reference protein. In some embodiments, the thermal stability of the protein comprising a variant Fc region is greater than the thermal stability of the equivalent wild-type reference protein.

Various amino acid substitutions may increase the tendency of the protein to form dimers or higher order aggregates. Such a tendency may be determined by various techniques known in the art, including for example by size-exclusion chromatography (SEC), ultracentrifugation dynamic light scattering (DLS) and many others (e.g. see Engelsman 2011). In some embodiments, the proportion of monomer in the protein comprising a variant Fc region is within ±3%, ±2% or ±1% of the proportion of monomer in the equivalent wild-type reference protein. In some embodiments, the proportion of monomer in the protein comprising a variant Fc region is not significantly different from the proportion of monomer in the equivalent wild-type reference protein. In some embodiments, the proportion of monomer in the protein comprising a variant Fc region is greater than the proportion of monomer in the equivalent wild-type reference protein.

Biopharmaceutical preparations change as they age, but are considered to be stable for so long as their characteristics fall within the manufacturer's specifications. The number of days that the product remains stable at the recommended storage conditions is referred to as the shelf life. Experimental protocols commonly used for data collection to serve as the basis to estimate a product's shelf life are referred to as stability studies. Stability testing is commonly carried out by means of real-time stability studies under recommended storage conditions or accelerated stability studies under elevated stress conditions, for example of protein concentration, temperature, humidity, shaking or light exposure (e.g. see Bajaj 2012). In some embodiments, accelerated stability testing may be carried out at one or more protein concentrations in the range 1 mg/mL to 100 mg/mL. In some embodiments, accelerated stability testing may be carried out at one or more temperatures within the range 25° C. to 60° C. In some embodiments, the stability of the protein comprising a variant Fc region is within ±20%, within ±10%, within ±5% or within ±2% of the stability of the equivalent wild-type reference protein. In some embodiments, the stability of the protein comprising a variant Fc region is not significantly different from the stability of the equivalent wild-type reference protein. In some embodiments, the stability of the protein comprising a variant Fc region is greater than the stability of the equivalent wild-type reference protein. In each case, stability may be measured using any one or more of any suitable stability studies or tests, including real-time stability testing, accelerated stability testing at any suitable protein concentration or temperature, with any suitable experimental measurement, including for example, DSC, DSF, CD, thermal challenge assay, SEC, ultracentrifugation, DLS, measurements of binding activity either to antigens or to other ligands or receptors among others (see e.g. Senisterra 2009; Jain 2017). As is well known to those skilled in the art, there are many different protocols to implement these experimental techniques. For example, thermal stability may be measured by DSF using the fluorescent probe SYPRO® Orange but various other dyes may also be used (e.g. Niesen 2007). Or as a further example, binding to antigens or other ligands or receptors may be measured by surface plasmon resonance, enzyme-linked immunoassay, NanoBiT® immunoassay or many other types of ligand binding assays. Examples of stability measurements are provided in Example 7, Example 8 and Example 12.

Proteins Comprising a Variant Fc Region Having Unaltered Pharmacokinetics

Proteins which comprise an Fc region commonly have an extended half-life in vivo due to binding to the FcRn receptor. Various methods to measure half-life in vivo are well known in the art (e.g. see Liu 2018). Typically, they involve injection of the protein into a suitable animal (for example a mouse or rat), collection of blood samples at suitable intervals, measurement of the concentration of protein in the plasma (or serum), and mathematical analysis of the resulting data. Besides half-life, other pharmacokinetic parameters may be determined, including for example, volume of distribution, maximum plasma concentration, area under the curve and clearance.

In some embodiments, pharmacokinetic parameters exhibited by the protein comprising a variant Fc region are indistinguishable from pharmacokinetic parameters exhibited by the corresponding wild-type reference protein. In some embodiments, pharmacokinetic parameters exhibited by the protein comprising a variant Fc region are not significantly different from pharmacokinetic parameters exhibited by the corresponding wild-type reference protein. In some embodiments, pharmacokinetic parameters exhibited by the protein comprising a variant Fc region are not substantially different from pharmacokinetic parameters exhibited by the corresponding wild-type reference protein. In some embodiments the protein comprising a variant Fc region differs by less than 50%, preferably less than 20%, less than 10% or less than 5% from the half-life of a wild-type reference protein in one or more pharmacokinetic parameters. In each case the proteins to be compared are manufactured using essentially the same cell line and essentially the same culture conditions and are purified in essentially the same way. In each case "pharmacokinetic parameters" means any one or more of half-life, volume of distribution, maximum plasma concentration, area under the curve and clearance rate as determined using an appropriate mathematical method from concentration measurements on samples of blood, plasma or serum following administration of the protein to a mammal.

In some embodiments, pharmacokinetic parameters are measured following administration of test samples to mice which are transgenic for human FcRn, for example as described in Example 10.

Methods for Reducing Fc-Induced Effector Functions

In some aspects, a method is provided to substantially reduce Fc-induced effector functions of a protein comprising a Fc region by substantially reducing any one or more of the following: binding to one or more Fcγ receptors, binding to C1q, ADCC, ADCP, CDC. The method comprises:
    a) substituting the amino acid at position 234 or the amino acid at position 235 or the amino acids at both positions 234 and 235 and
    b) altering the amino acid at position 236 to arginine (R).
wherein the binding of the protein to human FcγRI is significantly reduced compared with the binding of a reference protein comprising the amino acid substitutions L234A, L235A and P329G.

In some embodiments, the resulting protein comprising a variant Fc region has one or more of the desirable properties recited in more detail above, namely: (a) similar or greater binding activity to FcRn compared with an wild-type reference protein, (b) substantially reduced ADCC compared with an wild-type reference protein, (c) substantially reduced CDC compared with an wild-type reference protein, (d) substantially reduced toxicity compared with an wild-type reference protein, (e) minimal immunogenicity compared with an wild-type reference protein, (f) unaltered glycosylation compared with an wild-type reference protein, (g) similar or improved homogeneity and/or stability during manufacture and/or storage compared with an wild-type reference protein, (h) similar pharmacokinetic parameters compared with an wild-type reference protein.

The required amino acid substitutions are accomplished using any of a range of techniques well known in the art. Typically these involve: (a) synthesis and/or assembly of DNA which encodes the protein having the desired amino acid substitutions, (b) expression of the protein encoded by the DNA using a suitable cellular or non-cell-based system, (c) isolation of the protein (d) testing the isolated protein for the desired reduction in Fc-induced effector function. Examples of steps (a), (b) and (c) are provided in Example 1. Examples of step (d) are provided in Example 2, Example 4, Example 5, Example 6, Example 9. Many possible variations on this method will be apparent to a person skilled in the art.

Proteins Comprising a Variant Fc Region with Particular Amino Acid Substitutions As shown in Example 2 and Table 8, we have identified proteins containing a variant Fc region which comprise new sets of amino acid substitutions that surprisingly result in significantly lower binding to FcγRI than seen with a comparable LALAPG reference protein (although it was previously reported to have 'completely abolished' FcγR and C1q interactions—see Schlothauer 2016). Any of these new sets of amino acid substitutions may be used to reduce binding to FcγRI compared with the LALAPG reference.

In some aspects a protein is provided which comprises a variant Fc region comprising a set of amino acid substitutions selected from: L234A/L235A/G236R, L234A/L235S/G236R, L234A/L235T/G236R, L234D/L235H/G236R, L234D/L235K/G236R, L234D/L235Q/G236R, L234D/L235S/G236R, L234D/L235T/G236R, L234E/L235D/G236R, L234E/L235H/G236R, L234E/L235I/G236R, L234E/L235V/G236R, L234G/L235H/G236R, L234G/L235Q/G236R, L234G/L235S/G236R, L234H/L235I/G236R, L234H/L235S/G236R, L234K/L235Q/G236R, L234K/L235R/G236R, L234K/L235S/G236R, L234K/L235T/G236R, L234K/L235V/G236R, L234Q/L235A/G236R, L234Q/L235D/G236R, L234Q/L235H/G236R, L234Q/L235Q/G236R, L234Q/L235R/G236R, L234Q/L235S/G236R, L234Q/L235T/G236R, L234Q/L235V/G236R, L234R/L235D/G236R, L234R/L235E/G236R, L234R/L235H/G236R, L234R/L235I/G236R, L234R/L235K/G236R, L234R/G236R, L234R/L235Q/G236R, L234R/L235R/G236R, L234R/L235T/G236R, L234S/L235D/G236R, L234S/L235E/G236R, L234S/L235G/G236R, L234S/L235H/G236R, L234S/L235I/G236R, L234S/G236R, L234S/L235R/G236R, L234S/L235T/G236R, L234S/L235V/G236R, L234T/L235A/G236R, L234T/L235I/G236R, L234T/L235K/G236R, L234T/L235Q/G236R, L234T/L235R/G236R, L234T/L235S/G236R, L234T/L235T/G236R, L234T/L235V/G236R.

In some aspects a protein is provided which comprises a variant Fc region comprising a set of amino acid substitutions selected from: L234A/L235A/G236R, L234A/L235S/G236R, L234A/L235T/G236R, L234D/L235H/G236R, L234D/L235K/G236R, L234D/L235Q/G236R, L234D/L235S/G236R, L234D/L235T/G236R, L234E/L235D/G236R, L234E/L235H/G236R, L234E/L235I/G236R, L234E/L235V/G236R, L234G/L235H/G236R, L234G/L235Q/G236R, L234G/L235S/G236R, L234H/L235I/G236R, L234H/L235S/G236R, L234K/L235Q/G236R, L234K/L235R/G236R, L234K/L235S/G236R, L234K/L235T/G236R, L234K/L235V/G236R, L234Q/L235A/G236R, L234Q/L235D/G236R, L234Q/L235H/G236R, L234Q/L235Q/G236R, L234Q/L235R/G236R, L234Q/L235S/G236R, L234Q/L235T/G236R, L234Q/L235V/G236R, L234R/L235D/G236R, L234R/L235E/G236R, L234R/L235H/G236R, L234R/L235I/G236R, L234R/L235K/G236R, L234R/G236R, L234R/L235Q/G236R, L234R/L235R/G236R, L234R/L235T/G236R, L234S/L235D/G236R, L234S/L235E/G236R, L234S/L235G/G236R, L234S/L235H/G236R, L234S/L235I/G236R, L234S/G236R, L234S/L235R/G236R, L234S/L235T/G236R, L234S/L235V/G236R, L234T/L235A/G236R, L234T/L235I/G236R, L234T/L235K/G236R, L234T/L235Q/G236R, L234T/L235R/G236R, L234T/L235S/G236R, L234T/L235T/G236R, L234T/L235V/G236R, L235T/G236R.

In some aspects a protein is provided which comprises a variant Fc region comprising a set of amino acid substitutions selected from: L234A/L235A/G236R, L234A/L235S/G236R, L234A/L235T/G236R, L234D/L235H/G236R, L234D/L235K/G236R, L234D/L235Q/G236R, L234D/L235S/G236R, L234D/L235T/G236R, L234E/L235D/G236R, L234E/L235H/G236R, L234E/L235I/G236R, L234E/L235V/G236R, L234G/L235Q/G236R, L234G/L235S/G236R, L234Q/L235A/G236R, L234Q/L235D/G236R, L234Q/L235Q/G236R, L234Q/L235S/G236R, L234Q/L235T/G236R, L234Q/L235V/G236R, L234R/L235D/G236R, L234R/L235E/G236R, L234S/L235D/

G236R, L234S/L235E/G236R, L234S/L235G/G236R, L234S/L235I/G236R, L234S/G236R, L234S/L235T/G236R, L234S/L235V/G236R, L234T/L235A/G236R, L234T/L235I/G236R, L234T/L235Q/G236R, L234T/L235S/G236R, L234T/L235T/G236R, L234T/L235V/G236R, L235T/G236R.

In some aspects a protein is provided which comprises a variant Fc region comprising a set of amino acid substitutions selected from: L234A/L235A/G236R, L234A/L235S/G236R, L234D/L235K/G236R, L234D/L235S/G236R, L234D/L235T/G236R, L234G/L235S/G236R, L234H/L235S/G236R, L234K/L235Q/G236R, L234K/L235R/G236R, L234K/L235S/G236R, L234K/L235T/G236R, L234K/L235V/G236R, L234Q/L235A/G236R, L234Q/L235D/G236R, L234Q/L235R/G236R, L234Q/L235S/G236R, L234Q/L235T/G236R, L234Q/L235V/G236R, L234R/L235D/G236R, L234R/L235E/G236R, L234R/L235H/G236R, L234R/L235I/G236R, L234R/L235K/G236R, L234R/L235Q/G236R, L234R/L235R/G236R, L234S/L235G/G236R, L234S/L235H/G236R, L234S/L235I/G236R, L234S/L235R/G236R, L234S/L235T/G236R, L234S/L235V/G236R, L234T/L235K/G236R, L234T/L235Q/G236R, L234T/L235R/G236R, L234T/L235S/G236R, L234T/L235T/G236R, L234T/L235V/G236R.

In some aspects a protein is provided which comprises a variant Fc region comprising a set of amino acid substitutions selected from: L234A/L235A/G236R, L234A/L235S/G236R, L234D/L235K/G236R, L234D/L235S/G236R, L234D/L235T/G236R, L234G/L235S/G236R, L234H/L235S/G236R, L234K/L235Q/G236R, L234K/L235R/G236R, L234K/L235S/G236R, L234K/L235V/G236R, L234Q/L235A/G236R, L234Q/L235D/G236R, L234Q/L235R/G236R, L234Q/L235S/G236R, L234Q/L235T/G236R, L234Q/L235V/G236R, L234R/L235E/G236R, L234R/L235H/G236R, L234R/L235K/G236R, L234R/L235Q/G236R, L234R/L235R/G236R, L234S/L235G/G236R, L234S/L235H/G236R, L234S/L235I/G236R, L234S/L235R/G236R, L234S/L235T/G236R, L234S/L235V/G236R, L234T/L235Q/G236R, L234T/L235R/G236R, L234T/L235S/G236R, L234T/L235T/G236R, L234T/L235V/G236R.

In some aspects a protein is provided which comprises a variant Fc region comprising a set of amino acid substitutions selected from: L234A/L235S/G236R, L234G/L235S/G236R, L234Q/L235A/G236R, L234Q/L235S/G236R, L234Q/L235T/G236R, L234Q/L235V/G236R, L234S/L235G/G236R, L234S/L235I/G236R, L234S/L235T/G236R, L234S/L235V/G236R, L234T/L235Q/G236R, L234T/L235S/G236R, L234T/L235T/G236R, L234T/L235V/G236R.

In some aspects a protein is provided which comprises a variant Fc region comprising a set of amino acid substitutions selected from: L234G/L235S/G236R, L234S/L235T/G236R, L234S/L235V/G236R, L234T/L235Q/G236R, L234T/L235T/G236R IgG Sub-Classes In some embodiments, the Fc region which is altered to create a variant Fc region, may be selected from: IgG1, IgG2, IgG3 or IgG4. In some embodiments, the Fc region is IgG1. In humans, the wild-type residues corresponding to L234, L235 and G236 (EU numbering) in IgG1 are: V234, A235, A236 in IgG2; L234, L235 and G236 in IgG3 and F234, L235 and G236 in IgG4. IgG2 has a deletion at position 236 which is responsible for reduced binding to FcRn and reduced transplacental transport (Stapleton 2018). In some embodiments, an Arg residue inserted at 236 restores the binding of IgG2 to FcRn to be more similar to that of IgG1 and thus can increase the half-life of IgG2 in the circulation. In other embodiments, retention of the deletion at 236 preserves the reduced binding of IgG2 to FcRn.

In some embodiments a protein is provided which comprises a human IgG1 variant Fc region comprising a set of amino acid substitutions selected from: L234A/L235A/G236R, L234A/L235S/G236R, L234A/L235T/G236R, L234D/L235H/G236R, L234D/L235K/G236R, L234D/L235Q/G236R, L234D/L235S/G236R, L234D/L235T/G236R, L234E/L235D/G236R, L234E/L235H/G236R, L234E/L235I/G236R, L234E/L235V/G236R, L234G/L235H/G236R, L234G/L235Q/G236R, L234G/L235S/G236R, L234H/L235I/G236R, L234H/L235S/G236R, L234K/L235Q/G236R, L234K/L235R/G236R, L234K/L235S/G236R, L234K/L235T/G236R, L234K/L235V/G236R, L234Q/L235A/G236R, L234Q/L235D/G236R, L234Q/L235H/G236R, L234Q/L235Q/G236R, L234Q/L235R/G236R, L234Q/L235S/G236R, L234Q/L235T/G236R, L234Q/L235V/G236R, L234R/L235D/G236R, L234R/L235E/G236R, L234R/L235H/G236R, L234R/L235I/G236R, L234R/L235K/G236R, L234R/G236R, L234R/L235Q/G236R, L234R/L235R/G236R, L234R/L235T/G236R, L234S/L235D/G236R, L234S/L235E/G236R, L234S/L235G/G236R, L234S/L235H/G236R, L234S/L235I/G236R, L234S/G236R, L234S/L235R/G236R, L234S/L235T/G236R, L234S/L235V/G236R, L234T/L235A/G236R, L234T/L235I/G236R, L234T/L235K/G236R, L234T/L235Q/G236R, L234T/L235R/G236R, L234T/L235S/G236R, L234T/L235T/G236R, L234T/L235V/G236R.

In some embodiments a protein is provided which comprises a human IgG1 variant Fc region comprising a set of amino acid substitutions selected from: L234A/L235A/G236R, L234A/L235S/G236R, L234A/L235T/G236R, L234D/L235H/G236R, L234D/L235K/G236R, L234D/L235Q/G236R, L234D/L235S/G236R, L234D/L235T/G236R, L234E/L235D/G236R, L234E/L235H/G236R, L234E/L235I/G236R, L234E/L235V/G236R, L234G/L235H/G236R, L234G/L235Q/G236R, L234G/L235S/G236R, L234H/L235I/G236R, L234H/L235S/G236R, L234K/L235Q/G236R, L234K/L235R/G236R, L234K/L235S/G236R, L234K/L235T/G236R, L234K/L235V/G236R, L234Q/L235A/G236R, L234Q/L235D/G236R, L234Q/L235H/G236R, L234Q/L235Q/G236R, L234Q/L235R/G236R, L234Q/L235S/G236R, L234Q/L235T/G236R, L234Q/L235V/G236R, L234R/L235D/G236R, L234R/L235E/G236R, L234R/L235H/G236R, L234R/L235I/G236R, L234R/L235K/G236R, L234R/G236R, L234R/L235Q/G236R, L234R/L235R/G236R, L234R/L235T/G236R, L234S/L235D/G236R, L234S/L235E/G236R, L234S/L235G/G236R, L234S/L235H/G236R, L234S/L235I/G236R, L234S/G236R, L234S/L235R/G236R, L234S/L235T/G236R, L234S/L235V/G236R, L234T/L235A/G236R, L234T/L235I/G236R, L234T/L235K/G236R, L234T/L235Q/G236R, L234T/L235R/G236R, L234T/L235S/G236R, L234T/L235T/G236R, L234T/L235V/G236R, L235T/G236R.

In some embodiments a protein is provided which comprises a human IgG1 variant Fc region comprising a set of amino acid substitutions selected from: L234A/L235A/G236R, L234A/L235S/G236R, L234A/L235T/G236R, L234D/L235H/G236R, L234D/L235K/G236R, L234D/L235Q/G236R, L234D/L235S/G236R, L234D/L235T/G236R, L234E/L235D/G236R, L234E/L235H/G236R, L234E/L235I/G236R, L234E/L235V/G236R, L234G/L235Q/G236R, L234G/L235S/G236R, G236R, L234Q/L235D/G236R, L234Q/L235Q/G236R, L234Q/L235S/G236R, L234Q/L235T/G236R, L234Q/L235V/G236R, L234R/L235D/G236R, L234R/L235E/G236R, L234S/L235D/G236R, L234S/L235E/G236R, L234S/L235G/G236R, L234S/L235I/G236R, L234S/G236R, L234S/L235T/G236R, L234S/L235V/G236R, L234T/L235A/G236R, L234T/L235I/G236R, L234T/L235Q/G236R, L234T/L235S/G236R, L234T/L235T/G236R, L234T/L235V/G236R, L235T/G236R.

In some embodiments a protein is provided which comprises a human IgG1 variant Fc region comprising a set of amino acid substitutions selected from: L234A/L235A/G236R, L234A/L235S/G236R, L234D/L235K/G236R, L234D/L235S/G236R, L234D/L235T/G236R, L234G/L235S/G236R, L234H/L235S/G236R, L234K/L235Q/G236R, L234K/L235R/G236R, L234K/L235S/G236R, L234K/L235T/G236R, L234K/L235V/G236R, L234Q/L235A/G236R, L234Q/L235D/G236R, L234Q/L235R/G236R, L234Q/L235S/G236R, L234Q/L235T/G236R, L234Q/L235V/G236R, L234R/L235D/G236R, L234R/L235E/G236R, L234R/L235H/G236R, L234R/L235I/G236R, L234R/L235K/G236R, L234R/L235Q/G236R, L234R/L235R/G236R, L234S/L235G/G236R, L234S/L235H/G236R, L234S/L235I/G236R, L234S/L235R/G236R, L234S/L235T/G236R, L234S/L235V/G236R, L234T/L235K/G236R, L234T/L235Q/G236R, L234T/L235R/G236R, L234T/L235S/G236R, L234T/L235T/G236R, L234T/L235V/G236R.

In some embodiments a protein is provided which comprises a human IgG2 variant Fc region comprising a set of amino acid substitutions selected from: V234A/A236R, V234A/A235S/A236R, V234A/A235T/A236R, V234D/A235H/A236R, V234D/A235K/A236R, V234D/A235Q/A236R, V234D/A235S/A236R, V234D/A235T/A236R, V234E/A235D/A236R, V234E/A235H/A236R, V234E/A235I/A236R, V234E/A235V/A236R, V234G/A235H/A236R, V234G/A235Q/A236R, V234G/A235S/A236R, V234H/A235I/A236R, V234H/A235S/A236R, V234K/A235Q/A236R, V234K/A235R/A236R, V234K/A235S/A236R, V234K/A235T/A236R, V234K/A235V/A236R, V234Q/A235A/A236R, V234Q/A235D/A236R, V234Q/A235H/A236R, V234Q/A235Q/A236R, V234Q/A235R/A236R, V234Q/A235S/A236R, V234Q/A235T/A236R, V234Q/A235V/A236R, V234R/A235D/A236R, V234R/A235E/A236R, V234R/A235H/A236R, V234R/A235I/A236R, V234R/A235K/A236R, V234R/A235L/A236R, V234R/A235Q/A236R, V234R/A235R/A236R, V234R/A235T/A236R, V234S/A235D/A236R, V234S/A235E/A236R, V234S/A235G/A236R, V234S/A235H/A236R, V234S/A235I/A236R, V234S/A235L/A236R, V234S/A235R/A236R, V234S/A235T/A236R, V234S/A235V/A236R, V234T/A236R, V234T/A235I/A236R, V234T/A235K/A236R, V234T/A235Q/A236R, V234T/A235R/A236R, V234T/A235S/4236R, V234T/A235T/A236R, V234T/A235V/A236R.

In some embodiments a protein is provided which comprises a human IgG2 variant Fc region comprising a set of amino acid substitutions selected from: V234A/A236R, V234A/A235S/A236R, V234A/A235T/A236R, V234D/A235H/A236R, V234D/A235K/A236R, V234D/A235Q/A236R, V234D/A235S/A236R, V234D/A235T/Δ236R, V234E/A235D/A236R, V234E/A235H/Δ236R, V234E/A235I/A236R, V234E/A235V/A236R, V234G/A235H/A236R, V234G/A235Q/A236R, V234G/A235S/A236R, V234H/A235I/A236R, V234H/A235S/A236R, V234K/A235Q/A236R, V234K/A235R/A236R, V234K/A235S/A236R, V234K/A235T/A236R, V234K/A235V/A236R, V234Q/A235A/A236R, V234Q/A235D/A236R, V234Q/A235H/A236R, V234Q/A235Q/A236R, V234Q/A235R/A236R, V234Q/A235S/A236R, V234Q/A235T/A236R, V234Q/A235V/A236R, V234R/A235D/A236R, V234R/A235E/A236R, V234R/A235H/A236R, V234R/A235I/A236R, V234R/A235K/A236R, V234R/A235L/A236R, V234R/A235Q/A236R, V234R/A235R/A236R, V234R/A235T/A236R, V234S/A235D/A236R, V234S/A235E/A236R, V234S/A235G/A236R, V234S/A235H/A236R, V234S/A235I/A236R, V234S/A235L/A236R, V234S/A235R/A236R, V234S/A235T/A236R, V234S/A235V/A236R, V234T/A236R, V234T/A235I/A236R, V234T/A235Q/A236R, V234T/A235R/A236R, V234T/A235S/A236R, V234T/A235T/Δ236R, V234T/A235V/A236R, A235T/Δ236R.

In some embodiments a protein is provided which comprises a human IgG2 variant Fc region comprising a set of amino acid substitutions selected from: V234A/A236R, V234A/A235S/A236R, V234A/A235T/A236R, V234D/A235H/Δ236R, V234D/A235K/A236R, V234D/A235Q/A236R, V234D/A235S/A236R, V234D/A235T/A236R, V234E/A235D/A236R, V234E/A235H/A236R, V234E/A235I/A236R, V234E/A235V/A236R, V234G/A235Q/A236R, V234G/A235S/A236R, V234Q/A235A/A236R, V234Q/A235D/A236R, V234Q/A235Q/A236R, V234Q/A235S/A236R, V234Q/A235T/A236R, V234Q/A235V/A236R, V234R/A235D/A236R, V234R/A235E/A236R, V234S/A235D/A236R, V234S/A235E/A236R, V234S/A235G/A236R, V234S/A235I/A236R, V234S/A235L/A236R, V234S/A235T/A236R, V234S/A235V/A236R, V234T/A236R, V234T/A235I/A236R, V234T/A235Q/A236R, V234T/A235S/A236R, V234T/A235T/A236R, V234T/A235V/A236R, A235T/A236R.

In some embodiments a protein is provided which comprises a human IgG2 variant Fc region comprising a set of amino acid substitutions selected from: V234A/A235S, V234A/A235T, V234D/A235H, V234D/A235K, V234D/A235Q, V234D/A235S, V234D/A235T, V234E/A235D, V234E/A235H, V234E/A235I, V234E/A235V, V234G/A235H, V234G/A235Q, V234G/A235S, V234H/A235I, V234H/A235S, V234K/A235Q, V234K/A235R, V234K/A235S, V234K/A235T, V234K/A235V, V234Q/A235A, V234Q/A235D, V234Q/A235H, V234Q/A235Q, V234Q/A235R, V234Q/A235S, V234Q/A235T, V234Q/A235V, V234R/A235D, V234R/A235E, V234R/A235H, V234R/A235I, V234R/A235K, V234R/A235L, V234R/A235Q, V234R/A235R, V234R/A235T, V234S/A235D, V234S/A235E, V234S/A235G, V234S/A235H, V234S/A235I, V234S/A235L, V234S/A235R, V234S/A235T, V234S/A235V, V234T/A235I, V234T/A235K, V234T/A235Q, V234T/A235R, V234T/A235S, V234T/A235T, V234T/A235V.

In some embodiments a protein is provided which comprises a human IgG2 variant Fc region comprising a set of amino acid substitutions selected from: V234A/A235S, V234A/A235T, V234D/A235H, V234D/A235K, V234D/A235Q, V234D/A235S, V234D/A235T, V234E/A235H, V234E/A235I, V234E/A235V, V234G/A235H, V234G/A235Q, V234G/A235S, V234H/A235I, V234H/A235S, V234K/A235Q, V234K/A235S, V234K/A235T, V234K/A235V, V234Q/A235A, V234Q/A235D, V234Q/A235H, V234Q/A235Q, V234Q/A235R, V234Q/A235S, V234Q/A235T, V234Q/A235V, V234R/A235D, V234R/A235E, V234R/A235I, V234R/A235L, V234R/A235Q, V234R/A235T, V234S/A235D, V234S/A235E, V234S/A235G, V234S/A235H, V234S/A235I, V234S/A235L, V234S/A235R, V234S/A235T, V234S/A235V, V234T/A235I,

V234T/A235K, V234T/A235Q, V234T/A235R, V234T/A235S, V234T/A235T, V234T/A235V.

In some embodiments a protein is provided which comprises a human IgG2 variant Fc region comprising a set of amino acid substitutions selected from: V234A/A235S, V234A/A235T, V234D/A235H, V234D/A235K, V234D/A235Q, V234D/A235S, V234D/A235T, V234E/A235D, V234E/A235H, V234E/A235I, V234E/A235V, V234G/A235Q, V234G/A235S, V234H/A235I, V234H/A235S, V234K/A235Q, V234K/A235R, V234K/A235S, V234K/A235T, V234K/A235V, V234Q/A235Q, V234Q/A235R, V234Q/A235S, V234Q/A235T, V234R/A235D, V234R/A235E, V234R/A235H, V234R/A235I, V234R/A235K, V234R/A235L, V234R/A235Q, V234R/A235R, V234R/A235T, V234S/A235D, V234S/A235E, V234S/A235G, V234S/A235H, V234S/A235I, V234S/A235L, V234S/A235R, V234S/A235T, V234S/A235V, V234T/A235I, V234T/A235K, V234T/A235Q, V234T/A235R, V234T/A235S, V234T/A235T.

In some embodiments a protein is provided which comprises a human IgG2 variant Fc region comprising a set of amino acid substitutions selected from: V234D/A235K, V234D/A235Q, V234D/A235S, V234D/A235T, V234E/A235I, V234K/A235Q, V234K/A235R, V234K/A235S, V234K/A235T, V234R/A235D, V234R/A235E, V234R/A235I, V234R/A235K, V234R/A235L, V234R/A235Q, V234R/A235R, V234R/A235T, V234S/A235I, V234S/A235L, V234S/A235R, V234S/A235T,.

In some embodiments a protein is provided which comprises a human IgG4 variant Fc region comprising a set of amino acid substitutions selected from: F234A/L235A/G236R, F234A/L235S/G236R, F234A/L235T/G236R, F234D/L235H/G236R, F234D/L235K/G236R, F234D/L235Q/G236R, F234D/L235S/G236R, F234D/L235T/G236R, F234E/L235D/G236R, F234E/L235H/G236R, F234E/L235I/G236R, F234E/L235V/G236R, F234G/L235H/G236R, F234G/L235Q/G236R, F234G/L235S/G236R, F234H/L235I/G236R, F234H/L235S/G236R, F234K/L235Q/G236R, F234K/L235R/G236R, F234K/L235S/G236R, F234K/L235T/G236R, F234K/L235V/G236R, F234Q/L235A/G236R, F234Q/L235D/G236R, F234Q/L235H/G236R, F234Q/L235Q/G236R, F234Q/L235R/G236R, F234Q/L235S/G236R, F234Q/L235T/G236R, F234Q/L235V/G236R, F234R/L235D/G236R, F234R/L235E/G236R, F234R/L235H/G236R, F234R/L235I/G236R, F234R/L235K/G236R, F234R/G236R, F234R/L235Q/G236R, F234R/L235R/G236R, F234R/L235T/G236R, F234S/L235D/G236R, F234S/L235E/G236R, F234S/L235G/G236R, F234S/L235H/G236R, F234S/L235I/G236R, F234S/G236R, F234S/L235R/G236R, F234S/L235T/G236R, F234S/L235V/G236R, F234T/L235A/G236R, F234T/L235I/G236R, F234T/L235K/G236R, F234T/L235Q/G236R, F234T/L235R/G236R, F234T/L235S/G236R, F234T/L235T/G236R, F234T/L235V/G236R.

In some embodiments a protein is provided which comprises a human IgG4 variant Fc region comprising a set of amino acid substitutions selected from: F234A/L235A/G236R, F234A/L235S/G236R, F234A/L235T/G236R, F234D/L235H/G236R, F234D/L235K/G236R, F234D/L235Q/G236R, F234D/L235S/G236R, F234D/L235T/G236R, F234E/L235D/G236R, F234E/L235H/G236R, F234E/L235I/G236R, F234E/L235V/G236R, F234G/L235H/G236R, F234G/L235Q/G236R, F234G/L235S/G236R, F234H/L235I/G236R, F234H/L235S/G236R, F234K/L235Q/G236R, F234K/L235R/G236R, F234K/L235S/G236R, F234K/L235T/G236R, F234K/L235V/G236R, F234Q/L235A/G236R, F234Q/L235D/G236R, F234Q/L235H/G236R, F234Q/L235Q/G236R, F234Q/L235R/G236R, F234Q/L235S/G236R, F234Q/L235T/G236R, F234Q/L235V/G236R, F234R/L235D/G236R, F234R/L235E/G236R, F234R/L235H/G236R, F234R/L235I/G236R, F234R/L235K/G236R, F234R/G236R, F234R/L235Q/G236R, F234R/L235R/G236R, F234R/L235T/G236R, F234S/L235D/G236R, F234S/L235E/G236R, F234S/L235G/G236R, F234S/L235H/G236R, F234S/L235I/G236R, F234S/G236R, F234S/L235R/G236R, F234S/L235T/G236R, F234S/L235V/G236R, F234T/L235A/G236R, F234T/L235I/G236R, F234T/L235K/G236R, F234T/L235Q/G236R, F234T/L235R/G236R, F234T/L235S/G236R, F234T/L235T/G236R, F234T/L235V/G236R, L235T/G236R.

In some embodiments a protein is provided which comprises a human IgG4 variant Fc region comprising a set of amino acid substitutions selected from: F234A/L235A/G236R, F234A/L235S/G236R, F234A/L235T/G236R, F234D/L235H/G236R, F234D/L235K/G236R, F234D/L235Q/G236R, F234D/L235S/G236R, F234D/L235T/G236R, F234E/L235D/G236R, F234E/L235H/G236R, F234E/L235I/G236R, F234E/L235V/G236R, F234G/L235Q/G236R, F234G/L235S/G236R, F234Q/L235A/G236R, F234Q/L235D/G236R, F234Q/L235Q/G236R, F234Q/L235S/G236R, F234Q/L235T/G236R, F234Q/L235V/G236R, F234R/L235D/G236R, F234R/L235E/G236R, F234S/L235D/G236R, F234S/L235E/G236R, F234S/L235G/G236R, F234S/L235/G236R, F234S/G236R, F234S/L235T/G236R, F234S/L235V/G236R, F234T/L235A/G236R, F234T/L235I/G236R, F234T/L235Q/G236R, F234T/L235S/G236R, F234T/L235T/G236R, F234T/L235V/G236R, L235T/G236R.

Various Species

In some embodiments, the Fc region which is altered to create a variant Fc region, may be from any mammalian species. In some embodiments, the Fc region which is altered is selected from: mouse, rat rabbit, rhesus or cynomolgus monkey. In some embodiments, the Fc region which is altered is selected from any IgG subclass. In some embodiments, the Fc region which is altered is selected from mouse IgG1, mouse IgG2a, mouse IgG2b, mouse IgG3, rat IgG1, rat IgG2a, rat IgG2b or rat IgG2c.

Additional Amino Acid Alterations

In some embodiments, any of the proteins comprising a variant Fc region as described above, or resulting from the methods described above may also comprise additional amino acid alterations, which may be insertions, deletions or substitutions and may result in other desirable properties, for example including any one or more of: (a) altered binding activity to FcRn, which may be higher or lower (b) altered pharmacokinetic parameters which may include slower clearance or more rapid clearance, (c) altered immunogenicity, which may be higher or lower (d) altered glycosylation or elimination of glycosylation (e) improved homogeneity and/or stability during manufacture and/or storage, (f) ability to form heterodimeric structures (for example for the creation of bispecific antibodies), (g) ability to form only monomeric structures, (h) ability to form multimeric structures (for example hexamers), (i) ability to form site-specific conjugates, (j) ability to bind to an antigen, or any other desirable property known in the art. It is envisaged that, by a combination of appropriate amino acid alterations, one or more of these desirable properties may be combined within a protein comprising a variant Fc region.

Amino acid residues involved in binding to FcRn include: Thr250, Met252, Ile253, Ser254, Thr256, Lys288, Val 305, Thr307, Val308, Leu309, His310, Gln311, Asp312, Leu314, Lys317, Lys360, Gln362, Ala378, Glu380, Glu382, Ser415, Ser424, Met428, His433, Asn434, His435, Tyr436, Thr437 (Shields 2001; Kim 1999; Hinton 2004; Yeung 2009). Not all changes which increase the affinity of IgG for FcRn at pH 6.0 necessarily result in an increase in half-life. Examples of amino acid alterations which increase binding to FcRn at pH 6.0 and also are reported to increase elimination phase half-lives in monkeys or mice transgenic for human FcRn include: T250Q/M428L, V308P, M428L, M252Y/S254T/ T256E, M428L/N434S, N434A, N434H, T307A/E380A/ N434A, H433K/N434F, L309D/Q311H/N434S (Datta-Mannan 2011; Petkova 2006; Deng 2010; Vaccaro 2005; Lee 2019). In some embodiments, any of the variant Fc regions previously described which comprise amino acid alterations at one or more of residues 234, 235 and 236 may also comprise amino acid substitutions at one, two or three positions selected from: 250, 252, 253, 254, 256, 288, 305, 307, 308, 309, 310, 311, 312, 314, 317, 360, 362, 378, 380, 382, 415, 424, 428, 433, 434, 435, 436, 437. (EU numbering). In some embodiments, any of the variant Fc regions previously described which comprise amino acid alterations at one or more of residues 234, 235 and 236 may also comprise amino acid substitutions selected from: T250Q/ M428L, V308P, M428L, M252Y/S254T/T256E, M428L/ N434S, N434A, N434H, T307A/E380A/N434A, H433K/ N434F, L309D/Q311H/N434S.

Asn297 is normally glycosylated in Fc proteins. This glycosylation can be eliminated by substitution of any other amino acid residue. Elimination of glycosylation may reduce the heterogeneity of the resulting protein and may be particularly advantageous for manufacture in cells other than mammalian cells. In some embodiments, any of the variant Fc regions previously described which comprise amino acid alterations at one or more of residues 234, 235 and 236 may also comprise alteration of N297.

Human IgG4 has a heterogenous structure and a tendency to form heterodimers with serum IgG4. This can be abolished by the amino acid substitution S228P (Angal 1993). Aggregation of IgG4 under low pH conditions and Fab-arm exchange can be reduced by altering Arg409 (WO2006033386; WO2008145142) or Lys370 (WO2010063785; US2017029521). IgG4 can also be stabilised by substitution of Cys131 combined with substitution of any amino acid in the upper hinge region to Cys (WO2012022982). In some embodiments, any of the variant IgG4 Fc regions previously described which comprise amino acid alterations at one or more of residues 234, 235 and 236 may also comprise one or more substitutions selected from: S228P, S228P/R409K, R409K, K370X, C131X/S217C, C131X/K218C, C131X/Y222C, C131X/ G223C (where X is any amino acid residue except C).

The C-terminus of IgGs can be heterogenous due to the presence or absence of Lys447. This may be prevented by deletion of the last one or two amino acid residues. In some embodiments, any of the variant Fc regions previously described which comprise amino acid alterations at one or more of residues 234, 235 and 236 may also comprise a deletion of K447 or of G446 and K447.

The physicochemical properties of antibodies and other proteins containing Fc regions can be optimized by selection of suitable amino acid alterations (reviewed by Yang 2018). This can give important advantages for manufacturing and stability of the products. The introduction of additional intradomain or interdomain disulphide bonds in the CH2 and/or CH3 domains may stabilise the structure. For example: L242C/K334C, V240C/L334C, L242C/K334C, A287C/L306C, R292C/V302C, P343C/A431C, S375C/ P396C, S375C/P396C/P445G/G446E/K447C, P343C/ A431C/P445G/G446E/K447C. Other stabilising substitutions which do not introduce new disulphide bonds include: Q295F/Y296A and D239E/L241M. In some embodiments, any of the variant Fc regions previously described which comprise amino acid alterations at one or more of residues 234, 235 and 236 may also comprise one or more substitutions selected from: L242C/K334C, V240C/L334C, L242C/ K334C, A287C/L306C, R292C/V302C, P343C/A431C, S375C/P396C, S375C/P396C/P445G/G446E/K447C, P343C/A431C/P445G/G446E/K447C, Q295F/Y296A, D239E/L241M.

Bispecific or multi-specific antibodies are of increasing interest and a vast number of different ways of engineering them is known in the art (e.g. see Brinkmann 2017). Formats which contain a heterodimeric Fc region are particularly attractive as they allow for bispecificity and altered valency while retaining the developability and druggability of an antibody (e.g. see Moore 2019). A general approach is to make different and complementary mutations in two different heavy chains such that the assembly of homodimers is inhibited but heterodimers are promoted. For example, this might be done by substituting a bulky residue into one chain and a small residue into another chain ('knobs into holes') or by substituting residues of opposite charge (D or E into one chain and K or R into the other). Exemplary pairs of mutations include: T366Y with Y407T (Ridgway 1996); S354C/T366W with Y349C/T366S/L368A/Y407V (Merchant 1998); F405L with K409R (Labrijn 2013); D399K/ E356K with K409D/K392D (Gunasekaran 2010); E357Q/ S364K with L368D/K370S (Moore 2019); S364H/F405A with Y349T/T394F (Moore 2011); D221E/P228E/L368E with D221R/P228R/K409R (Strop 2012); T350V/T366L/ K392L/T394W with T350V/L351Y/F405A/Y407V (Von Kreudenstein 2013); K360E/K409W with Q347R/D399V/ F405T (Choi 2013); K360E/K409W/Y349C with Q347R/ D399V/F405T/S354C (Choi 2015a); K370E/K409W with E357N/D399V/F405T (Choi 2015b); K360D/D399M/ Y407A with E345R/Q347R/T366V/K409V (Leaver-Fay 2016); Y349S/K370Y/T366M/K409V with E356G/E357D/ S364Q/Y407A (Leaver-Fay 2016); L351D/L368E with L351K/T366K (Nardis 2017). Thus, in some embodiments, any of the variant Fc regions previously described which comprise amino acid alterations at one or more of residues 234, 235 and 236 may also comprise substitutions selected from: T366Y with Y407T; S354C/T366W with Y349C/ T366S/L368A/Y407V; F405L with K409R; D399K/E356K with K409D/K392D; E357Q/S364K with L368D/K370S; S364H/F405A with Y349T/T394F; D221E/P228E/L368E with D221R/P228R/K409R; T350V/T366L/K392L/T394W with T350V/L351Y/F405A/Y407V; K360E/K409W with Q347R/D399V/F405T; K360E/K409W/Y349C with Q347R/D399V/F405T/S354C; K370E/K409W with E357N/D399V/F405T; K360D/D399M/Y407A with E345R/Q347R/T366V/K409V; Y349S/K370Y/T366M/ K409V with E356G/E357D/S364Q/Y407A; L351D/L368E with L351K/T366K wherein the first of the pair of substitutions is applied to one protein chain and the second of the pair is applied to the other protein chain.

The bivalent nature of IgG antibodies is often advantageous, increasing the affinity of binding to targets and giving the potential to cause physiological effects, for example by receptor dimerization. However, these properties are not always desirable and sometimes it would be preferable to have a monomeric antibody. This can be achieved by making amino acid alterations in the Fc region which reduce the tendency of chains to associate. In some instances, such alterations may be the same as one half of the pairs of substitutions described above in the context of bispecific antibodies, since elimination of the tendency to form homodimers is a feature of such alterations. A number of other amino acid substitutions have been described which result in the formation of monomeric Fc regions, including for example: T394D, F408R (Wilkinson 2013); L351F/T366R/P395K/F405R/Y407E (Shan 2016); F405Q (Rose 2011); L351Y/T366Y/L368A/P395R/F405R/Y407M/K409A; L351S/T366R/L368H/P395K/F405E/Y407K/K409A; L351K/T366S/P395K/F405R/Y407A/K409Y (Ying 2012); L351S/T366R/L368H/P395K (Ying 2014); S364N/Y407N/K409T, F405N/Y407T (Ishino 2013). Thus, in some embodiments, any of the variant Fc regions previously described which comprise amino acid alterations at one or more of residues 234, 235 and 236 may also comprise substitutions selected from: T394D, F408R, L351F/T366R/P395K/F405R/Y407E; F405Q, L351Y/T366Y/L368A/P395R/F405R/Y407M/K409A; L351S/T366R/L368H/P395K/F405E/Y407K/K409A, L351K/T366S/P395K/F405R/Y407A/K409Y, L351S/T366R/L368H/P395K, S364N/Y407N/K409T, F405N/Y407T.

IgG antibodies can organize into ordered hexamers on cell surfaces after binding their antigen. These hexamers bind the first component of complement C1 to induce CDC. Mutations have been identified which enhance hexamer formation and complement activation (de Jong 2016). They include substitutions at E345, E430 and S440. Some substitutions, for example E345R and E430F promoted hexamer formation in solution, whereas others only promoted hexamer formation when the antibody was bound to its target. An alternative way to promote hexamer formation is to make the substitutions L309C/H310L and add part of the C-terminal sequence of IgM or IgA (Mekhaiel 2011). If controlled aggregation were required without complement activation, then it would be desirable to combine one of the aforesaid Fc variants with a hexamer-promoting mutation. Thus, in some embodiments, any of the variant Fc regions previously described which comprise amino acid alterations at one or more of residues 234, 235 and 236 may also comprise a substitution at E345, E430 or S440 or substitutions L309C/H310L together with the addition of an appropriate fragment of IgA or IgM.

Antibody-drug conjugates are promising anti-tumour agents. However, conventional methods for attaching drugs or other functional moieties to proteins result in heterogenous products as a result of variable attachment to a number of different sites on the protein. To overcome this problem, several methods have been developed for site-specific modification, by engineering specific sites to contain, for example, cysteine, glutamine, unnatural amino acids, short peptide tags or glycans (Zhou 2017). Cysteine may be inserted or substituted at various places in the Fc region, though a partially solvent accessible site may be preferred since conjugates to such a Cys residue showed greatest stability in plasma. Suitable sites include T289C, A339C and S442C. In a systematic screening of all possible conjugation sites more than 30 were identified which offer high stability for conjugation including the following residues in the heavy chain constant regions: 120, 166, 172, 178, 187, 199, 203, 209, 262, 336, 337, 344, 345, 382, 388, 411, 421, 424, 438, 443 (Ohri 2018). In some embodiments, any of the variant Fc regions previously described which comprise amino acid alterations at one or more of residues 234, 235 and 236 may also comprise one or more amino acid alterations designed to create a site suitable for site-specific conjugation of a drug or other functional moiety, including for example, one or more at sites selected from: 120, 166, 172, 178, 187, 199, 203, 209, 262, 289, 336, 337, 339, 344, 345, 382, 388, 411, 421, 424, 438, 442, 443.

Immunoglobulin constant domains within the Fc region are folded in a manner which is highly homologous to variable domains. Such constant domains, particularly the CH3 domain can provide a scaffold wherein amino acid alterations can create new antigen-binding sites (Wozniak-Knopp 2017). Such constructs may be especially useful in the construction of bispecific antibodies. For example, residues 358 to 362, 413 to 415 and 418 to 422 (which together form a contiguous solvent-exposed surface) are candidates for mutation to create new antigen-binding sites. Other residues may also be mutated to improve binding characteristics, including for example: 355 to 357, 383 to 389, up to 5 amino acid insertions between 389 and 390, 416, 417 and 440 to 447 (Wozniak-Knopp 2017). Thus, in some embodiments, any of the variant Fc regions previously described which comprise amino acid alterations at one or more of residues 234, 235 and 236 may also comprise one or more amino acid alterations designed to create an antigen-binding site. In some embodiments, any of the variant Fc regions previously described which comprise amino acid alterations at one or more of residues 234, 235 and 236 may also comprise one or more amino acid alterations at any number of residues selected from: 355 to 362, 383 to 389, 413 to 422, 440 to 447 In order to create an antigen-binding site.

Antibodies, Antibody Mimetics and Fragments Thereof

In some embodiments, any of the proteins comprising a variant Fc region as described above, or resulting from the methods described above also comprises an antigen-binding domain. The antigen-binding domain may be a full-length antibody, for example a chimeric antibody, a humanized antibody, a human antibody, a non-human antibody or a fragment thereof. The antigen-binding domain may comprise a combination of heavy and light chain variable regions or it may comprise a single-chain variable region (scFv) or it may comprise a single variable region. The antigen-binding domain may be a diabody, a Fab fragment or a F(ab')2 fragment. The protein comprising a variant Fc region may itself be a full-length antibody, for example a chimeric antibody, a humanized antibody or a human antibody. It may be a bispecific antibody, a multi-specific antibody, or any other kind of antibody known in the art provided that it comprises an Fc region. The antigen-binding domain may be derived from a non-immunoglobulin scaffold (e.g. adnectin, affibody®, affilin®, affimer®, alphabody®, anticalin®, avimer, darpin®, fynomer®, glubody, knottin, Kunitz domain, monobody®, nanoclamp, tetranectin (e.g. see Simeon 2018).

Virtually any molecule can be targeted by an antigen-binding domain and any antigen-binding domain known in the art or yet to be discovered may be incorporated into the protein of this invention.

Fusion Proteins

In some embodiments, any of the proteins comprising a variant Fc region as described above, or resulting from the methods described above is a fusion protein. Such a fusion protein may comprise one or more additional domains with any desirable properties. For example, an additional domain may be a binding protein, receptor, enzyme or cytokine. An additional domain may be derived from any source, including for example prokaryote, eukaryote, plant, animal, mammal, human or it may be synthetically derived. Numerous such fusion proteins are known in the art, including for example etanercept, alefacept, abatacept, rilonacept, romiplostim, belatacept, aflibercept (Beck 2011; Jafari 2017). In some embodiments, the variant Fc region is fused to a polypeptide for which it is desirable to increase the size, solubility, expression yield, and/or serum half-life. In some embodiments, the variant Fc region is fused to a polypeptide as a tag for purification and/or detection of the polypeptide.

Conjugates

In some embodiments, any of the proteins comprising a variant Fc region as described above, or resulting from the methods described above may be a conjugated protein. Such a conjugated protein may comprise one or more additional components with any desirable properties. For example, an additional component may be a binding protein, receptor, enzyme, cytokine, toxin, drug, hapten, label, chelating agent, radio-isotope, affinity tag, linker, peptide, nucleic acid or carbohydrate. Such additional component may be attached to the protein comprising a variant Fc region by any method known in the art.

Methods of Producing Proteins Comprising a Variant Fc Region

In some embodiments, any of the proteins comprising a variant Fc region as described above, or resulting from the methods described above may be produced by chemical synthesis, or preferably, by recombinant expression techniques.

Monoclonal antibodies can be produced using a wide variety of techniques which are routine and well known in the art, including for example: (a) immunization of animals (e.g. mice, rats, rabbits, sheep, camelids, sharks, including animals which may be transgenic for human immunoglobulin genes), followed by production and selection of hybridomas or isolation of antigen-specific B cells; (b) isolation of antigen-specific B cells from non-immunized animals, including for example, humans, (c) display technologies, including for example phage, yeast, ribosome or mammalian display. Newer technologies for production of monoclonal antibodies are also contemplated, including for example immunization of animals followed by sequencing of the resulting polyclonal antibodies and production of corresponding monoclonal antibodies by recombinant DNA technology. Antibody mimetics can be produced using a wide variety of display technologies making use of non-immunoglobulin scaffolds (e.g. see Simeon 2018).

Recombinant proteins can be produced using a wide variety of techniques which are routine and well known in the art. A typical process includes the following steps:

a) Design of the amino acid sequence of the recombinant protein. If it is to include an antigen-binding domain from an antibody, antibody fragment or antibody mimetic, the sequence of the antigen-binding domain is determined either by protein sequencing, or by sequencing of the DNA or RNA which encodes it. If the recombinant protein is to include one or more domains derived from a natural source, then the sequence of such domains may be obtained from an appropriate database. Protein domains may be connected by suitable peptide linkers, typically short flexible strings of amino acids. Desired amino acid alterations may be introduced into the designed sequence.

b) Design of DNA encoding the desired amino acid sequence. Because of the redundancy of the genetic code, many possible nucleic acid sequences can encode the same protein. It is desirable to optimise the properties of the nucleic acid sequence for convenience of subsequent manipulations and to ensure high expression levels of the protein. Such optimisation may include the removal or addition of restriction enzyme sites, codon optimisation to make best use of any codon bias in the translation machinery of the host cell, removal of unwanted RNA splice sites, removal of sequences which may create unwanted secondary structure to mRNA and any other optimisation techniques known in the art.

c) Synthesis of the DNA and insertion into an expression vector. A gene encoding the desired amino acid sequence may be synthesized de novo by any technique known in the art, or it may be created by site-directed mutagenesis from a similar pre-existing gene. Such a gene may be inserted into a bacterial plasmid for amplification to provide a stock of DNA from which the gene may be excised and inserted into an expression vector which may for example, be a plasmid or retrovirus.

d) Transfection and expression of protein. The expression vector is transfected or transduced into a suitable host cell, which may, for example, be a mammalian cell such as NS0, CHO, PER.C6 or HEK. Alternatively, the host cell may be a bacteria, yeast, plant or insect cell or any other cell type which is suited for the production of recombinant proteins. The cells are cultured under suitable conditions to enable the transduced gene(s) to be expressed and the protein to be synthesised and (preferably) secreted from the cell. Depending on the design of the expression vector, the method for transfection or transduction and the procedure for selection of the transfected or transduced cells, gene expression and protein synthesis may be transient or stable and it may be constitutive or induced e) Protein purification. The protein is purified from the cell lysate or (preferably) from the culture supernatant by any suitable technique(s) known in the art including for example, by chromatography (for example ion exchange, affinity, and size exclusion chromatography), centrifugation, differential solubility, or by any other standard technique for the purification of proteins. Affinity purification using Protein A is a preferred method for purification of proteins comprising Fc regions.

An alternative process for the production of recombinant protein may use a cell-free expression system (e.g. see Gregorio 2019). It is envisaged that proteins of this invention may be made by such a process.

Nucleic Acids

In some aspects, a nucleic acid is provided which encodes a protein comprising a variant Fc region comprising amino acid substitutions at residues 234 and/or 235 and an amino acid substitution or insertion of Arg at residue 236. The encoded protein may also have any of the functional properties and/or additional amino acid alterations described above or any combination thereof. The nucleic acid may be DNA or RNA. It may be obtained, and its nucleotide sequence determined by any suitable method known in the art.

Vectors

In some aspects, a vector is provided which comprises a nucleic acid that encodes a protein comprising a variant Fc region comprising amino acid substitutions at residues 234 and/or 235 and an amino acid substitution or insertion of Arg at residue 236. The encoded protein may also have any of the functional properties and/or additional amino acid alterations described above or any combination thereof. In some embodiments, the vector is able to cause the expression of the protein when introduced into a suitable host cell. In some embodiments the vector is a self-replicating extra-chromosomal vector. In some embodiments, the vector can integrate into a host cell genome. Expression vectors are constructed to be compatible with the host cell type. Thus, expression vectors, which find use in the present invention, include but are not limited to those which enable expression of a protein comprising a variant Fc region in bacteria, yeast, plant, insect or mammalian cells as well as in vivo systems, for example by the generation of transgenic animals or plants. As is known in the art, a variety of expression vectors are available, commercially or otherwise, that may find use for expressing proteins of the invention. In some embodiments, the vector is a virus. In some embodiments, the vector is a virus which is capable of infecting human cells in vivo and causing expression of the protein of the invention. In some embodiments, the vector is an oncolytic virus. As is well known in the art, any expression vector may be associated with any suitable promoter, enhancer or other expression-facilitating elements.

Cells

In some aspects, a cell is provided which can produce the protein comprising a variant Fc region comprising amino acid substitutions at residues 234 and/or 235 and an amino acid substitution or insertion of Arg at residue 236. Examples of suitable host cells include bacteria, yeast, plant or insect cells or mammalian cells such as NSO, CHO, PER.C6 or HEK. Alternatively, the host cell may be any other cell type which is suited for the production of recombinant proteins. In some embodiments the host cell comprises a nucleic acid stably incorporated into the cellular genome that encodes the protein comprising a variant Fc region. In other embodiments, the host cell comprises a non-integrated nucleic acid, such as a plasmid, cosmid, phagemid, or linear expression element that encodes the protein comprising a variant Fc region.

Pharmaceutical Compositions

In some aspects, the invention provides a pharmaceutical composition comprising a protein comprising a variant Fc region as defined in any of the aspects and embodiments herein. The pharmaceutical compositions may be formulated with pharmaceutically acceptable carriers, diluents, adjuvants and/or excipients in accordance with conventional techniques known in the art (e.g. see Remington 1995; Shire 2009). The pharmaceutically acceptable carriers, diluents, adjuvants and excipients should be suitable for the protein of the present invention and the chosen mode of administration. Suitability is determined based on the lack of significant negative impact on the desired biological properties (e.g. binding activity either to antigens or receptors, stability, pharmacokinetic parameters) and lack of toxicity to the subject to whom the composition is to be administered. The amount of active ingredients (including the protein of this invention) in the pharmaceutical composition may be varied so as to obtain an amount which is effective to achieve the desired therapeutic response. The selected amount may depend on the pharmacokinetic properties of the active ingredients, the route and timing of administration, the age, sex, weight and medical condition of the patient being treated, and similar factors well known in the art. The pharmaceutical composition may be administered by any parenteral route (e.g. by injection or infusion).

Therapeutic Applications

In some aspects, the invention provides a protein, e.g. antibody, or pharmaceutical composition as defined in any aspect or embodiment herein described, for use as a medicament. In another aspects, the invention provides a protein, e.g. antibody, or pharmaceutical composition as defined in any aspect or embodiment herein described, for use in the treatment of a disease. In another aspect, a method of treating a subject having a disease is provided, wherein the method comprises administering to the subject an effective amount of the protein, e.g. antibody, or pharmaceutical composition as defined in any aspect or embodiment herein described. Because the antibodies or proteins of this invention are not limited to any particular specificity or format, the range of diseases which may be treated is very wide. However, a common factor in the selection of a suitable disease indication is that it would be undesirable for the medicament to bind to Fcγ receptors and potentially cause inflammatory reactions or engage with other effector functions which could cause adverse effects. Such diseases may include, for example: angioedema, arthritis, asthma, atopic dermatitis, autoimmune disease, cancer, Castleman disease, coagulation disorders, Crohn's disease, cryopyrin associated periodic syndromes, diabetes, drug toxicity, eczema, graft-versus-host disease, hypercholesterolemia, hypophosphatemia, infectious disease, ischemic heart disease, macular degeneration, multiple sclerosis, muscle loss, osteoporosis, paroxysmal nocturnal haemoglobinuria, primary hemophagocytic lymphohistiocytosis, psoriasis, sepsis, sickle cell disease, stroke, systemic lupus erythematosus, thrombocytopenia purpura, transplantation, ulcerative colitis or other disease indications for which therapeutic monoclonal antibodies or Fc fusion proteins have been or are currently being used or tested in human subjects. In some circumstances, the reduction in undesirable or adverse reactions obtained by use of the protein of this invention (when compared with a similar protein not having the amino acid alterations of this invention) permits the use of higher doses, more frequent doses or more doses of the protein of the invention than would otherwise be considered safe or prudent for a similar protein not having the amino acid alterations of this invention. Thus the protein of this invention is expected to have a higher therapeutic index than a similar protein not having the amino acid alterations of this invention.

In some aspects, the invention provides a protein, e.g. antibody, or composition as defined in any aspect or embodiment herein described which has a reduced immunogenicity compared with a similar protein not having the amino acid alterations of this invention. Unwanted immunogenicity of biological drugs, particularly proteins, is a problem because it leads to the formation of anti-drug antibodies which can neutralise the therapeutic activity of the drug or cause adverse reactions or side-effects. Such anti-drug antibodies limit the duration of effective treatment. Binding to Fc receptors can enhance the immunogenicity of proteins which comprise an Fc region (Chen 2007, Loureiro 2011). A protein of this invention with reduced immunogenicity is particularly useful for therapeutic applications for a number of reasons, including for example: greater efficacy, lower toxicity, fewer side-effects, longer duration of effective therapy.

Research and Diagnostic Applications

In some aspects, the invention provides a protein, e.g. antibody, or composition as defined in any aspect or embodiment herein described, for use in a research or diagnostic test or a quality control test. Accordingly, the invention provides research and diagnostic methods and quality control methods and compositions using the proteins described herein. Such methods and compositions may be used for detecting or identifying a disease, for monitoring the progress of treatment, assessing status after treatment, monitoring for recurrence after treatment, evaluating risk of developing a disease, in vitro tests for activity of biological drugs and the like. In some aspects, the diagnostic method or composition is used ex vivo, for example to detect or measure the level of an antigen recognised by an antibody or protein of this invention. In other aspects, the diagnostic method or composition is used in vivo, for example to determine the localization within the body of an antigen recognised by an antibody or protein of this invention. Because the antibodies or proteins of this invention are not limited to any particular specificity or format, the range of research, quality control and diagnostic tests is very wide and may encompass almost any antigenic target, known or yet to be discovered, and may utilise any relevant technology known in the art, for example: enzyme-linked immunoassay, cell-based assays, radioimmunoassay, fluorescence assays, flow cytometry, surface plasmon resonance, chemiluminescence, electro-chemiluminescence, chromatographic assays, homogeneous immunoassays (e.g. AlphaLISA®, Lumit®, CEDIA®), immunohistology assays, Western blot, immunoprecipitation, lateral flow tests and the like. In some aspects, the antibody or protein of the invention is a conjugated protein comprising a component which is suitable for detection in the selected test system. In some aspects, the antibody or protein of the invention is radiolabelled for use in an in vivo diagnostic imaging test. However, a common factor in the selection and design of the test or composition is the desire to avoid unwanted binding of the antibody or protein of the invention to Fcγ receptors or to C1q or to engage in other effector functions which may otherwise cause assay interference or false positive or false negative responses. Research, quality control and diagnostic applications for proteins of this invention include, for example, any kind of test which measures binding to cells or protein arrays where Fcγ receptors may be present. Binding to such receptors may lead to 'false positive' responses. Such unwanted binding may be reduced or eliminated by the use of a protein of this invention. Other test applications for proteins of this invention include, for example, any kind of test where a protein of this invention is used as a control sample because of its lack of binding to Fcγ receptors or to C1q.

In some aspects of this invention a method is provided to reduce unwanted binding to Fcγ receptors of an antibody or Fc fusion protein or an antibody conjugate or a Fc fusion protein conjugate used in a test system for research or diagnosis comprising: (a) the manufacture of a variant form of the said antibody or Fc fusion protein or conjugate containing amino acid alterations according to this invention, (b) the substitution of said variant form in place of the original antibody or Fc fusion protein or conjugate. The test system may be for example: an enzyme-linked immunosorbent assay (ELISA), a fluorescence-based assay, an immunohistochemistry test, a chemiluminescence or electro-chemiluminescence test, a diagnostic imaging test or any other immunological test system.

EXAMPLES

The examples below are given so as to illustrate the practice of this invention. They are not intended to limit or define the entire scope of this invention. Due to differences in immunoglobulin alleles or due to different cloning strategies, there may be minor differences (i.e. amino acid alterations) between the amino acid sequences described herein and those reported elsewhere in the literature. Such differences do not limit the scope of this invention.

Example 1 Production of Antibodies Comprising Variant Fc Regions 1.1 Design, Expression and Purification Codon-optimised synthetic genes encoding the wild-type human IgG1 heavy chain constant region (SEQ ID NO:4) or variants thereof were provided by Genewiz® in pUC57-Kan vectors. The purified DNA was digested with NheI/NotI restriction enzymes and the gene extracted for ligation into a pUV mammalian expression vector. Similarly, a codon-optimised synthetic gene for human kappa light chain constant region (SEQ ID NO: 5) was ligated into a pUV vector. Synthetic genes encoding the VH and VL variable regions of anti-CD20 rituximab (SEQ ID NO: 6 and SEQ ID NO: 7), anti-CD3 muromonab (SEQ ID NO: 8 and SEQ ID NO: 9) or anti-CD52 alemtuzumab (SEQ ID NO: 10 and SEQ ID NO: 11) were provided by Genewiz® with NheI and AvaI restriction sites at the 5' and 3' ends for cloning. VH genes were digested, excised and ligated into the wild-type human IgG1 heavy chain pUV vector. VL genes were digested, excised and ligated into the human kappa light chain pUV vector. To create variants, synthetic genes containing variant Fc regions were synthesised with KasI and SacII restriction sites at the 5' and 3' ends and digested, excised and ligated into the existing vector encoding the immunoglobulin heavy chain of anti-CD20 (SEQ ID NO: 12). Variants of the anti-CD3 heavy chain (SEQ ID NO: 14) or anti-CD52 heavy chain (SEQ ID NO: 16) were generated by digesting the appropriate VH variable regions with NheI and AvaI followed by excision and ligation into anti-CD20 variant heavy chain vectors similarly digested with NheI and AvaI to remove the canti-CD20 VH sequence for replacement with anti-CD3 or anti-CD52. A similar process was used to create variants of wild-type human IgG2 (SEQ ID NO: 18), human IgG4 (SEQ ID NO: 19), mouse IgG2a (SEQ ID NO: 20), rat IgG2b (SEQ ID NO: 22) or rabbit IgG (SEQ ID NO: 24). In the case of human IgG4, in addition to the amino acid alterations made to modify binding to Fc receptors, an additional amino acid substitution S228P was introduced in order to stabilise the antibody structure (Angal 1993). For expression of mouse, rat or rabbit antibodies, the anti-CD20 VL gene was ligated with a gene encoding the relevant kappa light chain constant region (SEQ ID NO: 21, SEQ ID NO: 23 or SEQ ID NO: 25). Amino acid sequences of wild-type IgG Fc regions used herein and sites of amino acid alterations are illustrated in FIG. 1A, FIG. 1B and FIG. 1C. Sequences of the final inserts were confirmed by Sanger sequencing.

Intact antibodies were produced by transient transfection of HEK293 cells with a mixture of the appropriate heavy chain expression vector with the corresponding light chain expression vector encoding the immunoglobulin light chain of anti-CD20 (rituximab) (SEQ ID NO: 13), anti-CD3 (muromonab) (SEQ ID NO: 15) or anti-CD52 (alemtuzumab) (SEQ ID NO: 17). HEK293 cells were grown in suspension in serum-free culture medium (ThermoFisher Cat. No. 12338026) and transfected at a cell count of $2 \times 10^6$ viable cells/mL using linear polyethylenimine. The cells were cultured in Erlenmeyer flasks for 6 days at 37° C. with shaking at 140 rpm in 5% $CO_2$. Fc fusion proteins were produced in a similar way by transient transfection of HEK293 cells with an expression vector encoding the required fusion protein. Alternatively, antibodies were produced by transient transfection of CHO cells using similar mixtures of heavy and light chain expression vectors. Suspension-adapted CHO cells were cultured in serum-free medium, resuspended in MaxCyte buffer at $2 \times 10^8$ cells/mL and transfected by electroporation using a MaxCyte STC instrument (MaxCyte, Gaithersburg, USA) in accordance with the manufacturer's instructions. The cells were allowed to rest for 30 min then cultured at 37°C for 24 h and at 32°C for a further 10 days. The cells were harvested by centrifugation at 3000 g for 45 minutes and the supernatant was clarified using a 0.22 μm vacuum driven filter.

Culture supernatants were analysed by non-reducing SDS-polyacrylamide gel electrophoresis (SDS-PAGE) followed by staining with Coomassie Blue. This showed that all of the samples gave a single band corresponding to a molecular weight of approximately 150 kDa. Antibodies were purified using 1 mL MabSelect SuRe® Protein A chromatography columns (GE Life Sciences) and eluted with 0.1 M sodium citrate buffer pH 3.0 then neutralised with 10% (v/v) Tris base pH 9.0. Eluted antibodies were buffer exchanged into PBS pH 7.2 and concentrated as required using a centrifugal concentrator. The protein concentration was measured by absorbance at 280 nm using a Nanodrop® ND-1000 spectrophotometer (Thermo-Fisher) and adjusted to 1 mg/ml by dilution with PBS. Several separate transfection experiments were carried out. A list of samples prepared is shown in Table 5.

TABLE 5

Variant antibodies, showing amino acid alterations, species, subclass and target antigens. Samples 1-1 to 1-167 were prepared as culture supernatants. All other samples were purified by affinity chromatography on Protein A.

| Amino acid alterations and sample description | Species | Subclass | CD20 | CD20 | CD20 | CD3 | CD52 |
|---|---|---|---|---|---|---|---|
| | | | Sample number | | | | |
| wild-type reference | human | IgG1 | 1-1 | 10.0 | 2-1 | 3-1 | 4-1 |
| L234A/L235A/G236R | human | IgG1 | 1-2 | | 2-2 | | |
| L234A/L235D/G236R | human | IgG1 | 1-3 | | | | |
| L234A/L235E/G236R | human | IgG1 | 1-4 | | | | |
| L234A/L235G/G236R | human | IgG1 | 1-5 | | | | |
| L234A/L235H/G236R | human | IgG1 | 1-6 | | | | |
| L234A/L235I/G236R | human | IgG1 | 1-7 | | | | |
| L234A/L235K/G236R | human | IgG1 | 1-8 | | | | |
| L234A/G236R | human | IgG1 | 1-9 | | 2-3 | | |
| L234A/L235M/G236R | human | IgG1 | 1-10 | | | | |
| L234A/L235N/G236R | human | IgG1 | 1-11 | | | | |
| L234A/L235Q/G236R | human | IgG1 | 1-12 | | | | |
| L234A/L235R/G236R | human | IgG1 | 1-13 | | | | |
| L234A/L235S/G236R | human | IgG1 | 1-14 | | 2-4 | | |
| L234A/L235T/G236R | human | IgG1 | 1-15 | | 2-5 | | |
| L234A/L235V/G236R | human | IgG1 | 1-16 | | | | |
| L234D/L235A/G236R | human | IgG1 | 1-17 | | | | |
| L234D/L235D/G236R | human | IgG1 | 1-18 | | | | |
| L234D/L235E/G236R | human | IgG1 | 1-19 | | | | |
| L234D/L235G/G236R | human | IgG1 | 1-20 | | | | |
| L234D/L235H/G236R | human | IgG1 | 1-21 | | 2-6 | | |
| L234D/L235I/G236R | human | IgG1 | 1-22 | | | | |
| L234D/L235K/G236R | human | IgG1 | 1-23 | | 2-7 | | |
| L234D/G236R | human | IgG1 | 1-24 | | 2-8 | | |
| L234D/L235M/G236R | human | IgG1 | 1-25 | | | | |
| L234D/L235N/G236R | human | IgG1 | 1-26 | | | | |
| L234D/L235Q/G236R | human | IgG1 | 1-27 | | 2-9 | | |
| L234D/L235R/G236R | human | IgG1 | 1-28 | | | | |
| L234D/L235S/G236R | human | IgG1 | 1-29 | | 2-10 | | |
| L234D/L235T/G236R | human | IgG1 | 1-30 | | 2-11 | | |
| L234D/L235V/G236R | human | IgG1 | 1-31 | | | | |
| L234E/L235A/G236R | human | IgG1 | 1-32 | | | | |
| L234E/L235D/G236R | human | IgG1 | 1-33 | | 2-12 | | |
| L234E/L235E/G236R | human | IgG1 | 1-34 | | | | |
| L234E/L235G/G236R | human | IgG1 | 1-35 | | | | |
| L234E/L235H/G236R | human | IgG1 | 1-36 | | 2-13 | | |
| L234E/L235I/G236R | human | IgG1 | 1-37 | | 2-14 | | |
| L234E/L235K/G236R | human | IgG1 | 1-38 | | | | |
| L234E/G236R | human | IgG1 | 1-39 | | 2-15 | | |
| L234E/L235M/G236R | human | IgG1 | 1-40 | | | | |
| L234E/L235N/G236R | human | IgG1 | 1-41 | | | | |
| L234E/L235Q/G236R | human | IgG1 | 1-42 | | | | |
| L234E/L235R/G236R | human | IgG1 | 1-43 | | | | |
| L234E/L235S/G236R | human | IgG1 | 1-44 | | | | |
| L234E/L235T/G236R | human | IgG1 | 1-45 | | | | |
| L234E/L235V/G236R | human | IgG1 | 1-46 | | 2-16 | | |
| L234G/L235A/G236R | human | IgG1 | 1-47 | | | | |
| L234G/L235D/G236R | human | IgG1 | 1-48 | | | | |
| L234G/L235E/G236R | human | IgG1 | 1-49 | | | | |
| L234G/L235G/G236R | human | IgG1 | 1-50 | | | | |
| L234G/L235H/G236R | human | IgG1 | 1-51 | | 2-17 | | |
| L234G/L235I/G236R | human | IgG1 | 1-52 | | | | |
| L234G/L235K/G236R | human | IgG1 | 1-53 | | | | |
| L234G/G236R | human | IgG1 | 1-54 | | | | |
| L234G/L235M/G236R | human | IgG1 | 1-55 | | | | |
| L234G/L235N/G236R | human | IgG1 | 1-56 | | | | |
| L234G/L235Q/G236R | human | IgG1 | 1-57 | | 2-18 | | |
| L234G/L235R/G236R | human | IgG1 | 1-58 | | | | |

TABLE 5-continued

Variant antibodies, showing amino acid alterations, species, subclass and target antigens. Samples 1-1 to 1-167 were prepared as culture supernatants. All other samples were purified by affinity chromatography on Protein A.

| | | | Target Antigen | | | | |
|---|---|---|---|---|---|---|---|
| Amino acid alterations and sample description | Species | Subclass | CD20 | CD20 | CD20 | CD3 | CD52 |
| | | | | Sample number | | | |
| L234G/L235S/G236R | human | IgG1 | 1-59 | | 2-19 | 3-19 | 4-19 |
| L234G/L235T/G236R | human | IgG1 | 1-60 | | | | |
| L234G/L235V/G236R | human | IgG1 | 1-61 | | | | |
| L234H/L235A/G236R | human | IgG1 | 1-62 | | | | |
| L234H/L235D/G236R | human | IgG1 | 1-63 | | | | |
| L234H/L235E/G236R | human | IgG1 | 1-64 | | | | |
| L234H/L235G/G236R | human | IgG1 | 1-65 | | | | |
| L234H/L235H/G236R | human | IgG1 | 1-66 | | | | |
| L234H/L235I/G236R | human | IgG1 | 1-67 | | 2-20 | | |
| L234H/L235K/G236R | human | IgG1 | 1-68 | | | | |
| L234H/G236R | human | IgG1 | 1-69 | | | | |
| L234H/L235M/G236R | human | IgG1 | 1-70 | | | | |
| L234H/L235N/G236R | human | IgG1 | 1-71 | | | | |
| L234H/L235Q/G236R | human | IgG1 | 1-72 | | | | |
| L234H/L235R/G236R | human | IgG1 | 1-73 | | | | |
| L234H/L235S/G236R | human | IgG1 | 1-74 | | 2-21 | | |
| L234H/L235T/G236R | human | IgG1 | 1-75 | | | | |
| L234H/L235V/G236R | human | IgG1 | 1-76 | | | | |
| L234K/L235A/G236R | human | IgG1 | 1-77 | | | | |
| L234K/L235D/G236R | human | IgG1 | 1-78 | | | | |
| L234K/L235E/G236R | human | IgG1 | 1-79 | | | | |
| L234K/L235G/G236R | human | IgG1 | 1-80 | | | | |
| L234K/L235H/G236R | human | IgG1 | 1-81 | | | | |
| L234K/L235I/G236R | human | IgG1 | 1-82 | | | | |
| L234K/L235K/G236R | human | IgG1 | 1-83 | | | | |
| L234K/G236R | human | IgG1 | 1-84 | | | | |
| L234K/L235M/G236R | human | IgG1 | 1-85 | | | | |
| L234K/L235N/G236R | human | IgG1 | 1-86 | | | | |
| L234K/L235Q/G236R | human | IgG1 | 1-87 | | 2-22 | | |
| L234K/L235R/G236R | human | IgG1 | 1-88 | | 2-23 | | |
| L234K/L235S/G236R | human | IgG1 | 1-89 | | 2-24 | | |
| L234K/L235T/G236R | human | IgG1 | 1-90 | | 2-25 | | |
| L234K/L235V/G236R | human | IgG1 | 1-91 | | 2-26 | | |
| L234N/L235A/G236R | human | IgG1 | 1-92 | | | | |
| L234N/L235D/G236R | human | IgG1 | 1-93 | | | | |
| L234N/L235E/G236R | human | IgG1 | 1-94 | | | | |
| L234N/L235G/G236R | human | IgG1 | 1-95 | | | | |
| L234N/L235H/G236R | human | IgG1 | 1-96 | | | | |
| L234N/L235I/G236R | human | IgG1 | 1-97 | | | | |
| L234N/L235K/G236R | human | IgG1 | 1-98 | | | | |
| L234N/G236R | human | IgG1 | 1-99 | | | | |
| L234N/L235M/G236R | human | IgG1 | 1-100 | | | | |
| L234N/L235N/G236R | human | IgG1 | 1-101 | | | | |
| L234N/L235Q/G236R | human | IgG1 | 1-102 | | | | |
| L234N/L235R/G236R | human | IgG1 | 1-103 | | | | |
| L234N/L235S/G236R | human | IgG1 | 1-104 | | | | |
| L234N/L235T/G236R | human | IgG1 | 1-105 | | | | |
| L234N/L235V/G236R | human | IgG1 | 1-106 | | | | |
| L234Q/L235A/G236R | human | IgG1 | 1-107 | | 2-27 | | |
| L234Q/L235D/G236R | human | IgG1 | 1-108 | | 2-28 | | |
| L234Q/L235E/G236R | human | IgG1 | 1-109 | | | | |
| L234Q/L235G/G236R | human | IgG1 | 1-110 | | | | |
| L234Q/L235H/G236R | human | IgG1 | 1-111 | | 2-29 | | |
| L234Q/L235I/G236R | human | IgG1 | 1-112 | | | | |
| L234Q/L235K/G236R | human | IgG1 | 1-113 | | | | |
| L234Q/G236R | human | IgG1 | 1-114 | | 2-30 | | |
| L234Q/L235M/G236R | human | IgG1 | 1-115 | | | | |
| L234Q/L235N/G236R | human | IgG1 | 1-116 | | | | |
| L234Q/L235Q/G236R | human | IgG1 | 1-117 | | 2-31 | | |
| L234Q/L235R/G236R | human | IgG1 | 1-118 | | 2-32 | | |
| L234Q/L235S/G236R | human | IgG1 | 1-119 | 10.77 | 2-33 | | |
| L234Q/L235T/G236R | human | IgG1 | 1-120 | | 2-34 | | |
| L234Q/L235V/G236R | human | IgG1 | 1-121 | | 2-35 | | |
| L234R/L235A/G236R | human | IgG1 | 1-122 | | | | |
| L234R/L235D/G236R | human | IgG1 | 1-123 | | 2-36 | | |
| L234R/L235E/G236R | human | IgG1 | 1-124 | | 2-37 | | |
| L234R/L235G/G236R | human | IgG1 | 1-125 | | | | |
| L234R/L235H/G236R | human | IgG1 | 1-126 | | 2-38 | | |
| L234R/L235I/G236R | human | IgG1 | 1-127 | | 2-39 | | |
| L234R/L235K/G236R | human | IgG1 | 1-128 | | 2-40 | | |
| L234R/G236R | human | IgG1 | 1-129 | | 2-41 | | |

TABLE 5-continued

Variant antibodies, showing amino acid alterations, species, subclass and target antigens. Samples 1-1 to 1-167 were prepared as culture supernatants. All other samples were purified by affinity chromatography on Protein A.

| Amino acid alterations and sample description | Species | Subclass | CD20 | CD20 | CD20 | CD3 | CD52 |
|---|---|---|---|---|---|---|---|
| | | | | Sample number | | | |
| L234R/L235M/G236R | human | IgG1 | 1-130 | | | | |
| L234R/L235N/G236R | human | IgG1 | 1-131 | | | | |
| L234R/L235Q/G236R | human | IgG1 | 1-132 | | 2-42 | | |
| L234R/L235R/G236R | human | IgG1 | 1-133 | | 2-43 | | |
| L234R/L235S/G236R | human | IgG1 | 1-134 | | | | |
| L234R/L235T/G236R | human | IgG1 | 1-135 | | 2-44 | | |
| L234R/L235V/G236R | human | IgG1 | 1-136 | | | | |
| L234S/L235A/G236R | human | IgG1 | 1-137 | | | | |
| L234S/L235D/G236R | human | IgG1 | 1-138 | | 2-45 | | |
| L234S/L235E/G236R | human | IgG1 | 1-139 | | 2-46 | | |
| L234S/L235G/G236R | human | IgG1 | 1-140 | | 2-47 | | |
| L234S/L235H/G236R | human | IgG1 | 1-141 | | 2-48 | | |
| L234S/L235I/G236R | human | IgG1 | 1-142 | | 2-49 | | |
| L234S/L235K/G236R | human | IgG1 | 1-143 | | | | |
| L234S/G236R | human | IgG1 | 1-144 | | 2-50 | | |
| L234S/L235M/G236R | human | IgG1 | 1-145 | | | | |
| L234S/L235N/G236R | human | IgG1 | 1-146 | | | | |
| L234S/L235Q/G236R | human | IgG1 | 1-147 | | | | |
| L234S/L235R/G236R | human | IgG1 | 1-148 | | 2-51 | | |
| L234S/L235S/G236R | human | IgG1 | 1-149 | | | | |
| L234S/L235T/G236R | human | IgG1 | 1-150 | | 2-52 | 3-52 | 4-52 |
| L234S/L235V/G236R | human | IgG1 | 1-151 | | 2-53 | 3-53 | 4-53 |
| L234T/L235A/G236R | human | IgG1 | 1-152 | | 2-54 | | |
| L234T/L235D/G236R | human | IgG1 | 1-153 | | 2-55 | | |
| L234T/L235E/G236R | human | IgG1 | 1-154 | | | | |
| L234T/L235G/G236R | human | IgG1 | 1-155 | | | | |
| L234T/L235H/G236R | human | IgG1 | 1-156 | | 2-56 | | |
| L234T/L235I/G236R | human | IgG1 | 1-157 | | 2-57 | | |
| L234T/L235K/G236R | human | IgG1 | 1-158 | | 2-58 | | |
| L234T/G236R | human | IgG1 | 1-159 | | 2-59 | | |
| L234T/L235M/G236R | human | IgG1 | 1-160 | | | | |
| L234T/L235N/G236R | human | IgG1 | 1-161 | | | | |
| L234T/L235Q/G236R | human | IgG1 | 1-162 | | 2-60 | 3-60 | 4-60 |
| L234T/L235R/G236R | human | IgG1 | 1-163 | | 2-61 | | |
| L234T/L235S/G236R | human | IgG1 | 1-164 | | 2-62 | | |
| L234T/L235T/G236R | human | IgG1 | 1-165 | | 2-63 | 3-63 | 4-63 |
| L234T/L235V/G236R | human | IgG1 | 1-166 | | 2-64 | | |
| L234A/L235A | human | IgG1 | 1-167 | 10.16 | 2-65 | 3-65 | 4-65 |
| L234A/L235A/P329G (LALAPG reference) | human | IgG1 | | 10.75 | 2-66 | 3-66 | 4-66 |
| N297Q (aglycosyl) | human | IgG1 | | 10.2 | 2-67 | 3-67 | 4-67 |
| G236R/L328R | human | IgG1 | | | 2-68 | | |
| L234A/G237A | human | IgG1 | | | 2-69 | | |
| L234A/L235A/G237A | human | IgG1 | | | 2-70 | | |
| L234A/L235E | human | IgG1 | | | 2-71 | | |
| L235V/F243L/R292P/Y300L/P396L | human | IgG1 | | | 2-72 | | |
| D265A/P329A | human | IgG1 | | | 2-73 | | |
| L234A/L235A/K322A | human | IgG1 | | | 2-74 | | |
| L234F/L235E/P331S | human | IgG1 | | | 2-75 | | |
| L234F/L235Q/K322Q | human | IgG1 | | | 2-76 | | |
| L234A/L235A/G237A/P238S/H268A/A330S/P331S | human | IgG1 | | | 2-77 | | |
| E233P/L234V/L235A/G236A/A327G/A330S/P331S | human | IgG1 | | | 2-78 | | |
| L235A/G236R | human | IgG1 | | | 2-79 | | |
| L235S/G236R | human | IgG1 | | | 2-80 | | |
| G236R | human | IgG1 | | | 2-81 | | |
| L234Q/L235S | human | IgG1 | | 10.3 | 2-81 | | |
| L235G/G236R | human | IgG1 | | | 2-83 | | |
| L234G/G236R | human | IgG1 | | | 2-85 | | |
| L235T/G236R | human | IgG1 | | | 2-86 | | |
| L234S/G235T | human | IgG1 | | | 2-87 | | |
| L234Q/L235S/A236R | human | IgG2 | | 11.77 | | | |
| L234Q/L235S | human | IgG2 | | 11.144 | | | |
| L234Q/L235S/G236R | human | IgG4 | | 13.77 | | | |
| L234Q/L235S/G236R | mouse | IgG2a | | 2.77 | | | |
| L234Q/L235S/G236R | rat | IgG2b | | 8.77 | | | |
| L234Q/L235S/G236R | rabbit | IgG | | 23.77 | | | |

TABLE 5-continued

Variant antibodies, showing amino acid alterations, species, subclass and target antigens. Samples 1-1 to 1-167 were prepared as culture supernatants. All other samples were purified by affinity chromatography on Protein A.

| | | | | Target Antigen | | | |
|---|---|---|---|---|---|---|---|
| Amino acid alterations and sample description | Species | Subclass | CD20 | CD20 CD20 CD3 CD52 Sample number | | | |
| L234Q/L235S/G236R/ M252Y/S254T/T256E | human | IgG1 | | 10.145 | | | |
| L234Q/L235S/G236R T250Q/M428L | human | IgG1 | | 10.146 | | | |

Table 5 Variant antibodies, showing amino acid alterations, species, subclass and target antigens. Samples 1-1 to 1-167 were prepared as culture supernatants. All other samples were purified by affinity chromatography on Protein A.

1.2 Antigen Binding

The antigen binding properties of representative CD3 and CD52 antibodies were tested by enzyme-linked immunosorbent assay (ELISA). All steps were carried out at room temperature (18 to 22° C.). To a 96-well microplate (Sigma Cat. No. M9410-ICS) 50 μL was added of either: (a) CD3D/CD3E heterodimer (Sino Biologicals Cat. No. CT038-H2508H) 1 μg/mL in PBS or (b) Sheep Fc-CD52 fusion protein (Absolute Antibody Cat. No. PR00205) 5 μg/mL in PBS and incubated with shaking for approximately 2 h. The coating antigen was removed and 200 μL PBS containing 1% (w/v) casein and 0.05% (v/v) Proclin (block buffer) was added and incubated for approximately 3 h. The plates were rinsed with PBS containing 0.05% (v/v) Tween 20 (wash buffer) and test samples, diluted with block buffer to give a final concentration of 5 μg/mL, were added. The plates were incubated with shaking for approximately 1 h then rinsed with wash buffer. HRP-labelled rabbit anti-human IgG (Sigma Cat. No. A8972) was diluted 1:10,000 in block buffer and 100 μL was added to each well. The plates were incubated with shaking for approximately 2.5 h then washed four times with wash buffer and twice with water. 100 μL of 3,3',5,5'-tetramethylbenzidine liquid substrate, supersensitive (TMB) (Abcam Cat. No. ab171523) was added and the plates were incubated for approximately 10 min. 50 μL of 1M sulphuric acid was added to stop the reaction and the absorbance was read at 450 nm with 620 nm subtraction using a microplate spectrophotometer (Anthos Labtec HT). Each sample was tested in quadruplicate. The mean was calculated and the mean response of a negative control (buffer alone) was subtracted. The results are shown in Table 6. All of the CD3 variant antibodies gave positive binding to CD3 antigen and all of the CD52 variant antibodies gave positive binding to CD52 antigen. As specificity controls, there was no significant binding of a wild-type CD3 antibody to CD52 or of a wild-type CD52 antibody to CD3.

TABLE 6

Mean binding response of samples of purified antibodies containing variant antibodies binding to human CD3 or human CD52.

| | | | Mean Absorbance (number of replicates) | |
|---|---|---|---|---|
| Sample | Amino acid alterations and Sample Description | Target | CD3 (4) | CD52 (4) |
| Buffer | PBS | | | |
| 3-1 | wild type reference | CD3 | 1.009 | 0.006 |
| 3-19 | L234G/L235S/G236R | CD3 | 1.243 | nd |
| 3-52 | L234S/L235T/G236R | CD3 | 1.377 | nd |
| 3-53 | L234S/L235V/G236R | CD3 | 1.247 | nd |
| 3-60 | L234T/L235Q/G236R | CD3 | 1.332 | nd |
| 3-63 | L234T/L235T/G236R | CD3 | 1.044 | nd |
| 3-65 | L234A/L235A (LALA) | CD3 | 1.072 | nd |
| 3-66 | L234A/L235A/P329G (LALAPG reference) | CD3 | 1.127 | nd |
| 3-67 | N297Q (aglycosyl) | CD3 | 0.749 | nd |
| 4-1 | wild type reference | CD52 | 0.009 | 1.528 |
| 4-19 | L234G/L235S/G236R | CD52 | nd | 1.132 |
| 4-52 | L234S/L235T/G236R | CD52 | nd | 1.435 |
| 4-53 | L234S/L235V/G236R | CD52 | nd | 1.233 |
| 4-60 | L234T/L235Q/G236R | CD52 | nd | 1.353 |
| 4-63 | L234T/L235T/G236R | CD52 | nd | 1.481 |
| 4-65 | L234A/L235A (LALA) | CD52 | nd | 1.241 |
| 4-66 | L234A/L235A/P329G (LALAPG reference) | CD52 | nd | 1.349 |
| 4-67 | N297Q (aglycosyl) | CD52 | nd | 1.365 | nd = not done.

Example 2 Binding to Fcγ Receptors 2.1 Screening a Panel of Variants for Binding to Human FcγRI Binding analysis was carried out by surface plasmon resonance at 25° C. using a Biacore® T200 instrument with Biacore® T200 control software. The running buffer (HBS-EP+) consisted of 0.01 M HEPES pH 7.4, containing 0.15 M NaCl, 3 mM EDTA, and 0.05% v/v Surfactant P20. The sample compartment was held at 4° C. during analysis. Methods were run using the manufacturer's standard method wizards as described in the Biacore® T200 Instrument Handbook.

Polyclonal anti-histidine antibody (GE Healthcare Cat. No. 28-9950-56) was immobilised to a CM5 chip by EDC/NHS chemistry. The cell was activated by treatment with EDC/NHS for 7 min. The antibody was diluted to 5 μg/mL in 10 mM sodium acetate pH 4.5 and injected for 7 min at μL/min. The flow cell was deactivated by injection of 1M ethanolamine for 7 min. This process was repeated in the absence of anti-his antibody on a separate flow cell to generate a reference surface. Histidine-tagged recombinant human FcγRI (CD64) (Sino Biologicals Cat. No. 12056-

H08H) was diluted to 10 μg/mL in HBS-EP and injected for 2 min at a flow rate of 30 μL/min. Samples of undiluted culture supernatants from HEK293 cells expressing human IgG1 antibodies comprising variant Fc regions were injected for 1 min at 30 μL/min and allowed to disassociate for 2 min. All of the test samples showed substantially reduced binding to FcγRI compared with a control wild-type IgG antibody, and completely dissociated within 2 min. Therefore, regeneration between cycles was not necessary. Responses on the test flow cell (coupled with anti-His antibody) were analysed after subtraction of responses on the control flow cell (sham-coupled). The relative binding response was measured 55 sec after the beginning of sample injection. To account for any possible drift in response due to slow dissociation of the His-tagged FcγRI, the binding response was measured relative to a baseline interpolated between report points located before sample injection and at the end of dissociation.

The whole experiment was repeated three times. Due to the relatively crude nature of the samples (variable refractive index, presence of culture media and other cellular products), some sensorgrams were unsatisfactory and were eliminated from analysis. The mean and standard deviation of binding response was then calculated for each sample. The mean of all standard deviations was 6.7 RU. The highest mean response of 65.0 RU was given by Sample 1-167 (L234A/L235A). All variants containing the mutation G236R gave lower mean responses. Sample 1-119 (L234Q/L235S/G236R) was taken as a representative variant which was effectively silenced according to earlier experiments. It gave a mean response of 11.9 RU. A cut-off of 21.9 RU was calculated as equal to the mean response of this representative variant plus 1.645 times the mean standard deviation of the samples. Samples giving a response above this cut-off were deemed to give significantly greater binding to FcγRI compared with the representative sample 1-119.

TABLE 7

Mean binding response of samples of culture supernatant containing variant antibodies binding to human FcγRI.

| Sample | Amino acid alterations | Mean binding response (RU) | Exceed cut-off of 21.9 RU |
|---|---|---|---|
| 1-2 | L234A/L235A/G236R | 30.7 | Yes |
| 1-3 | L234A/L235D/G236R | 28.0 | Yes |
| 1-4 | L234A/L235E/G236R | 31.7 | Yes |
| 1-5 | L234A/L235G/G236R | 27.6 | Yes |
| 1-6 | L234A/L235H/G236R | 23.0 | Yes |
| 1-7 | L234A/L235I/G236R | 28.4 | Yes |
| 1-8 | L234A/L235K/G236R | 34.2 | Yes |
| 1-9 | L234A/G236R | 8.0 | |
| 1-10 | L234A/L235M/G236R | 27.4 | Yes |
| 1-11 | L234A/L235N/G236R | 19.5 | |
| 1-12 | L234A/L235Q/G236R | 34.3 | Yes |
| 1-13 | L234A/L235R/G236R | 26.9 | Yes |
| 1-14 | L234A/L235S/G236R | 32.1 | Yes |
| 1-15 | L234A/L235T/G236R | 8.0 | |
| 1-16 | L234A/L235V/G236R | 25.8 | Yes |
| 1-17 | L234D/L235A/G236R | 29.6 | Yes |
| 1-18 | L234D/L235D/G236R | 22.0 | Yes |
| 1-19 | L234D/L235E/G236R | 22.1 | Yes |
| 1-20 | L234D/L235G/G236R | 27.3 | Yes |
| 1-22 | L234D/L235I/G236R | 25.3 | Yes |
| 1-23 | L234D/L235K/G236R | 20.9 | |
| 1-24 | L234D/G236R | 11.9 | |
| 1-25 | L234D/L235M/G236R | 28.4 | Yes |
| 1-26 | L234D/L235N/G236R | 26.5 | Yes |
| 1-27 | L234D/L235Q/G236R | 8.3 | |
| 1-28 | L234D/L235R/G236R | 47.0 | Yes |
| 1-29 | L234D/L235S/G236R | 26.3 | Yes |
| 1-30 | L234D/L235T/G236R | 4.3 | |
| 1-31 | L234D/L235V/G236R | 27.2 | Yes |
| 1-32 | L234E/L235A/G236R | 44.1 | Yes |
| 1-34 | L234E/L235E/G236R | 30.9 | Yes |
| 1-35 | L234E/L235G/G236R | 71.2 | Yes |
| 1-36 | L234E/L235H/G236R | 21.4 | |
| 1-38 | L234E/L235K/G236R | 34.1 | Yes |
| 1-39 | L234E/G236R | 17.6 | |
| 1-40 | L234E/L235M/G236R | 19.9 | |
| 1-41 | L234E/L235N/G236R | 19.2 | |
| 1-42 | L234E/L235Q/G236R | 33.7 | Yes |
| 1-43 | L234E/L235R/G236R | 26.7 | Yes |
| 1-44 | L234E/L235S/G236R | 39.2 | Yes |
| 1-45 | L234E/L235T/G236R | 29.6 | Yes |
| 1-46 | L234E/L235V/G236R | 18.4 | |
| 1-47 | L234G/L235A/G236R | 23.0 | Yes |
| 1-48 | L234G/L235D/G236R | 23.6 | Yes |
| 1-49 | L234G/L235E/G236R | 31.8 | Yes |
| 1-50 | L234G/L235G/G236R | 29.5 | Yes |
| 1-51 | L234G/L235H/G236R | 19.0 | |
| 1-52 | L234G/L235I/G236R | 29.2 | Yes |
| 1-53 | L234G/L235K/G236R | 27.4 | Yes |
| 1-54 | L234G/G236R | 28.5 | Yes |
| 1-55 | L234G/L235M/G236R | 23.2 | Yes |
| 1-56 | L234G/L235N/G236R | 26.8 | Yes |
| 1-57 | L234G/L235Q/G236R | 13.6 | |
| 1-58 | L234G/L235R/G236R | 29.3 | Yes |
| 1-59 | L234G/L235S/G236R | 21.8 | |
| 1-60 | L234G/L235T/G236R | 26.5 | Yes |
| 1-61 | L234G/L235V/G236R | 32.9 | Yes |
| 1-62 | L234H/L235A/G236R | 29.4 | Yes |
| 1-63 | L234H/L235D/G236R | 38.5 | Yes |
| 1-64 | L234H/L235E/G236R | 22.8 | Yes |
| 1-65 | L234H/L235G/G236R | 31.6 | Yes |
| 1-66 | L234H/L235H/G236R | 36.3 | Yes |
| 1-67 | L234H/L235I/G236R | 2.8 | |
| 1-68 | L234H/L235K/G236R | 29.2 | Yes |
| 1-69 | L234H/G236R | 22.9 | Yes |
| 1-70 | L234H/L235M/G236R | 31.3 | Yes |
| 1-71 | L234H/L235N/G236R | 24.6 | Yes |
| 1-72 | L234H/L235Q/G236R | 33.3 | Yes |
| 1-73 | L234H/L235R/G236R | 35.3 | Yes |
| 1-74 | L234H/L235S/G236R | 10.9 | |
| 1-75 | L234H/L235T/G236R | 44.9 | Yes |
| 1-76 | L234H/L235V/G236R | 25.6 | Yes |
| 1-77 | L234K/L235A/G236R | 23.0 | Yes |
| 1-78 | L234K/L235D/G236R | 26.6 | Yes |
| 1-79 | L234K/L235E/G236R | 29.9 | Yes |
| 1-80 | L234K/L235G/G236R | 27.4 | Yes |
| 1-81 | L234K/L235H/G236R | 25.3 | Yes |
| 1-82 | L234K/L235I/G236R | 30.9 | Yes |
| 1-83 | L234K/L235K/G236R | 37.6 | Yes |
| 1-84 | L234K/G236R | 31.2 | Yes |
| 1-85 | L234K/L235M/G236R | 23.9 | Yes |
| 1-86 | L234K/L235N/G236R | 24.8 | Yes |
| 1-87 | L234K/L235Q/G236R | 8.4 | |
| 1-88 | L234K/L235R/G236R | 13.9 | |
| 1-89 | L234K/L235S/G236R | 16.1 | |
| 1-90 | L234K/L235T/G236R | 15.8 | |
| 1-91 | L234K/L235V/G236R | 12.8 | |
| 1-92 | L234N/L235A/G236R | 22.3 | Yes |
| 1-93 | L234N/L235D/G236R | 13.4 | |
| 1-94 | L234N/L235E/G236R | 16.4 | |
| 1-95 | L234N/L235G/G236R | 22.1 | Yes |
| 1-96 | L234N/L235H/G236R | 17.7 | |
| 1-97 | L234N/L235I/G236R | 14.1 | |
| 1-98 | L234N/L235K/G236R | 25.0 | Yes |
| 1-99 | L234N/G236R | 22.3 | Yes |
| 1-100 | L234N/L235M/G236R | 19.9 | |
| 1-101 | L234N/L235N/G236R | 16.9 | |
| 1-102 | L234N/L235Q/G236R | 4.5 | |
| 1-103 | L234N/L235R/G236R | 30.4 | Yes |
| 1-104 | L234N/L235S/G236R | 18.4 | |
| 1-105 | L234N/L235T/G236R | 8.6 | |
| 1-106 | L234N/L235V/G236R | 18.9 | |

TABLE 7-continued

Mean binding response of samples of culture supernatant containing variant antibodies binding to human FcγRI.

| Sample | Amino acid alterations | Mean binding response (RU) | Exceed cut-off of 21.9 RU |
|---|---|---|---|
| 1-107 | L234Q/L235A/G236R | 13.4 | |
| 1-108 | L234Q/L235D/G236R | 18.9 | |
| 1-109 | L234Q/L235E/G236R | 28.8 | Yes |
| 1-110 | L234Q/L235G/G236R | 28.1 | Yes |
| 1-111 | L234Q/L235H/G236R | 10.0 | |
| 1-112 | L234Q/L235I/G236R | 34.7 | Yes |
| 1-113 | L234Q/L235K/G236R | 26.9 | Yes |
| 1-115 | L234Q/L235M/G236R | 38.4 | Yes |
| 1-116 | L234Q/L235N/G236R | 26.8 | Yes |
| 1-117 | L234Q/L235Q/G236R | 16.8 | |
| 1-118 | L234Q/L235R/G236R | 20.1 | |
| 1-119 | L234Q/L235S/G236R | 11.9 | |
| 1-120 | L234Q/L235T/G236R | 20.0 | |
| 1-121 | L234Q/L235V/G236R | 20.9 | |
| 1-122 | L234R/L235A/G236R | 28.1 | Yes |
| 1-123 | L234R/L235D/G236R | 11.1 | |
| 1-124 | L234R/L235E/G236R | 16.7 | |
| 1-125 | L234R/L235G/G236R | 31.9 | Yes |
| 1-126 | L234R/L235H/G236R | 14.3 | |
| 1-127 | L234R/L235I/G236R | 10.7 | |
| 1-128 | L234R/L235K/G236R | 19.2 | |
| 1-129 | L234R/G236R | 21.1 | |
| 1-131 | L234R/L235N/G236R | 10.8 | |
| 1-132 | L234R/L235Q/G236R | 10.1 | |
| 1-133 | L234R/L235R/G236R | 17.2 | |
| 1-134 | L234R/L235S/G236R | 34.0 | Yes |
| 1-136 | L234R/L235V/G236R | 32.5 | Yes |
| 1-137 | L234S/L235A/G236R | 29.6 | Yes |
| 1-139 | L234S/L235E/G236R | 11.6 | |
| 1-140 | L234S/L235G/G236R | 11.2 | |
| 1-142 | L234S/L235I/G236R | 12.0 | |
| 1-143 | L234S/L235K/G236R | 23.8 | Yes |
| 1-145 | L234S/L235M/G236R | 32.0 | Yes |
| 1-146 | L234S/L235N/G236R | 22.7 | Yes |
| 1-147 | L234S/L235Q/G236R | 29.6 | Yes |
| 1-148 | L234S/L235R/G236R | 11.1 | |
| 1-149 | L234S/L235S/G236R | 25.6 | Yes |
| 1-150 | L234S/L235T/G236R | 16.2 | |
| 1-152 | L234T/L235A/G236R | 11.8 | |
| 1-153 | L234T/L235D/G236R | 12.2 | |
| 1-154 | L234T/L235E/G236R | 24.0 | Yes |
| 1-155 | L234T/L235G/G236R | 26.9 | Yes |
| 1-156 | L234T/L235H/G236R | 18.9 | |
| 1-157 | L234T/L235I/G236R | 14.0 | |
| 1-158 | L234T/L235K/G236R | 6.7 | |
| 1-160 | L234T/L235M/G236R | 31.6 | Yes |
| 1-161 | L234T/L235N/G236R | 22.4 | Yes |
| 1-162 | L234T/L235Q/G236R | 17.0 | |
| 1-163 | L234T/L235R/G236R | 13.6 | |
| 1-164 | L234T/L235S/G236R | 25.4 | Yes |
| 1-167 | L234A/L235A | 65.0 | Yes |

From this experiment, a large number of variants was identified which gave low levels of binding to human FcγRI, whilst many other gave binding greater than a cut-off equal to the mean plus 1.645 times the standard deviation of the response of a representative low-binding sample (1-119). These variants which gave higher levels of binding were excluded from subsequent analysis.

2.2 Screening a Panel of Purified Variants for Binding to Human FcγRI

Based on the results of the screening of culture supernatants, variants giving low levels of binding to FcγRI were selected for further analysis as purified antibodies. Binding analysis was carried out by surface plasmon resonance at 25° C. using a Biacore® T200 instrument with Biacore® T200 control software. The sample compartment was held at 5° C. The running buffer (HBS-EP+) consisted of 0.01 M HEPES pH 7.4, containing 0.15 M NaCl, 3 mM EDTA, and 0.05% v/v Surfactant P20. Methods were run using the manufacturer's standard method wizards as described in the Biacore® T200 Instrument Handbook.

Mouse monoclonal anti-histidine antibody (Qiagen Cat. No. 34670) was immobilised to a CM5 chip by EDC/NHS chemistry. The cell was activated by treatment with EDC/NHS for 7 min. The antibody was diluted to 10 μg/mL in 10 mM sodium acetate pH 5.0 and injected for 7 min at 5 μL/min. The flow cell was deactivated by injection of 1M ethanolamine for 7 min. This process was repeated in the absence of anti-his antibody on a separate flow cell to generate a reference surface. Histidine-tagged recombinant human FcγRI (CD64) (Sino Biological Cat. No. 12056-H08H) was diluted to 5 μg/mL in HBS-EP and injected for 2 min at a flow rate of 10 μL/min. Samples of purified antibodies comprising variant Fc regions (1 mg/mL in PBS) were diluted with running buffer to 100 μg/mL and were injected for 1 min at 30 μL/min and allowed to disassociate for 2 min. Between each cycle, the chip was regenerated by injection of 10 mM glycine pH 3.0 for 0.5 min at a flow rate of 30 μL/min and recharged with a fresh injection of FcγRI. At the beginning of each experiment, three blank cycles were run, with buffer alone being injected instead of test sample. The average SPR signal (relative to the reference cell) was measured in a window approximately 8 to 13 seconds before the injection of test sample (baseline) and approximately 3 to 8 seconds before the end of injection (response). The response of the third of the blank (buffer) samples was subtracted from the response of each test sample in order to allow for any dissociation of the bound FcγRI giving a corrected response for each test sample. The whole experiment was repeated three times with the test samples being analysed in different orders each time. Two independent lots of the LALAPG reference antibody were included in each experiment. One lot (Sample 2-66) was prepared alongside all of the other variants and was used for the statistical comparison, while the other lot (Sample 10.75) was prepared on a separate occasion. This lot was run at the beginning and end of each experiment as a consistency check.

The mean of the corrected response for each sample across the three experiments was compared with the mean of the corrected response for the LALAPG reference antibody (Sample 66) using a two-tailed t-test, assuming unequal variances. Calculations were carried out using the T.TEST function in Microsoft Excel® 2016. Results were flagged as being (a) significantly lower ($p \leq 0.05$), (b) equivalent ($p > 0.05$) or (c) significantly higher ($p \leq 0.05$) than the mean corrected response of the LALAPG reference antibody (Sample 2-66). Results are shown in Table 8. A large proportion of the new variants (Samples 2-2 to 2-64 inclusive) gave significantly lower binding to FcγRI compared with the LALAPG reference antibody and many of them were indistinguishable from the buffer control. In contrast, all of the previously published variants (Samples 2-65, 2-67 to 2-78) and controls (Samples 2-79 to 2-83) gave higher or indistinguishable binding compared with the LALAPG reference antibody. The previously published variant, sample 2-72, which contains mutations designed to enhance binding to FcγRIII, gave binding to FcγRI which was comparable to the wild-type reference.

TABLE 8

Corrected binding responses of samples of purified antibodies binding to human FcγRI

| Sample | Amino acid alterations and Sample description | Expt 1 | Expt 2 | Expt 3 | Mean | P value | Compare with LALAPG |
|---|---|---|---|---|---|---|---|
| Buffer | Running buffer (Blank subtraction cycle) | 0.0 | 0.0 | 0.0 | 0.0 | 0.017 | Lower |
| 10.75 | L234A/L235A/P329G (LALAPG reference) | 80.8 | 43.3 | nd | 62.1 | 0.791 | Equivalent |
| 2-1 | wild type reference | nd | 2573.5 | 2600.3 | 2586.9 | 0.000 | Higher |
| 2-2 | L234A/L235A/G236R | 6.3 | 1.9 | 5.2 | 4.4 | 0.018 | Lower |
| 2-3 | L234A/G236R | 87.1 | 49.3 | 74.7 | 70.4 | 0.910 | Equivalent |
| 2-4 | L234A/L235S/G236R | 0.0 | −1.2 | 2.4 | 0.4 | 0.016 | Lower |
| 2-5 | L234A/L235T/G236R | 14.6 | 11.2 | 17.3 | 14.3 | 0.023 | Lower |
| 2-6 | L234D/L235H/G236R | 4.3 | 3.8 | 7.7 | 5.2 | 0.018 | Lower |
| 2-7 | L234D/L235K/G236R | −1.4 | 0.1 | 1.8 | 0.2 | 0.016 | Lower |
| 2-8 | L234D/G236R | 134.7 | 77.7 | 99.9 | 104.1 | 0.154 | Equivalent |
| 2-9 | L234D/L235Q/G236R | 5.7 | 5.9 | 7.1 | 6.2 | 0.020 | Lower |
| 2-10 | L234D/L235S/G236R | 4.0 | 2.7 | 3.6 | 3.4 | 0.019 | Lower |
| 2-11 | L234D/L235T/G236R | 3.0 | 4.3 | 5.5 | 4.3 | 0.019 | Lower |
| 2-12 | L234E/L235D/G236R | 15.1 | 9.4 | 12.3 | 12.3 | 0.022 | Lower |
| 2-13 | L234E/L235H/G236R | 4.6 | 4.5 | 6.2 | 5.1 | 0.019 | Lower |
| 2-14 | L234E/L235I/G236R | 11.6 | 8.1 | 11.7 | 10.4 | 0.022 | Lower |
| 2-15 | L234E/G236R | 232.6 | 143.2 | 179.3 | 185.0 | 0.035 | Higher |
| 2-16 | L234E/L235V/G236R | 4.8 | 5.5 | 7.4 | 5.9 | 0.020 | Lower |
| 2-17 | L234G/L235H/G236R | 1.8 | 4.2 | 24.4 | 10.1 | 0.008 | Lower |
| 2-18 | L234G/L235Q/G236R | 4.4 | 5.2 | 6.1 | 5.3 | 0.020 | Lower |
| 2-19 | L234G/L235S/G236R | −0.1 | 2.7 | 3.1 | 1.9 | 0.017 | Lower |
| 2-20 | L234H/L235I/G236R | 13.1 | 10.9 | 22.8 | 15.6 | 0.017 | Lower |
| 2-21 | L234H/L235S/G236R | 0.7 | 3.4 | 5.9 | 3.3 | 0.017 | Lower |
| 2-22 | L234K/L235Q/G236R | 2.9 | 6.1 | 5.8 | 4.9 | 0.019 | Lower |
| 2-23 | L234K/L235R/G236R | 0.6 | 2.8 | 3.2 | 2.2 | 0.017 | Lower |
| 2-24 | L234K/L235S/G236R | −1.7 | 1.1 | 4.1 | 1.2 | 0.015 | Lower |
| 2-25 | L234K/L235T/G236R | −1.8 | −1.0 | 1.1 | −0.6 | 0.016 | Lower |
| 2-26 | L234K/L235V/G236R | −1.7 | 0.4 | 3.1 | 0.6 | 0.016 | Lower |
| 2-27 | L234Q/L235A/G236R | 1.0 | 1.9 | 3.6 | 2.2 | 0.017 | Lower |
| 2-28 | L234Q/L235D/G236R | 4.3 | 2.7 | 4.4 | 3.8 | 0.019 | Lower |
| 2-29 | L234Q/L235H/G236R | 2.2 | 6.7 | 8.1 | 5.7 | 0.017 | Lower |
| 2-30 | L234Q/G236R | 41.9 | 27.0 | 49.0 | 39.3 | 0.064 | Equivalent |
| 2-31 | L234Q/L235Q/G236R | 0.3 | 3.0 | 34.9 | 12.7 | 0.019 | Lower |
| 2-32 | L234Q/L235R/G236R | −0.2 | 2.6 | 9.4 | 3.9 | 0.013 | Lower |
| 2-33 | L234Q/L235S/G236R | −1.8 | 1.6 | 3.8 | 1.2 | 0.015 | Lower |
| 2-34 | L234Q/L235T/G236R | 2.1 | 1.9 | 1.4 | 1.8 | 0.018 | Lower |
| 2-35 | L234Q/L235V/G236R | 0.5 | 2.5 | 4.5 | 2.5 | 0.017 | Lower |
| 2-36 | L234R/L235D/G236R | 0.4 | 0.9 | 4.2 | 1.8 | 0.017 | Lower |
| 2-37 | L234R/L235E/G236R | 0.9 | 1.8 | 4.6 | 2.4 | 0.017 | Lower |
| 2-38 | L234R/L235H/G236R | −1.2 | 0.7 | 2.3 | 0.6 | 0.016 | Lower |
| 2-39 | L234R/L235I/G236R | −0.8 | −0.2 | 1.2 | 0.1 | 0.017 | Lower |
| 2-40 | L234R/L235K/G236R | 0.0 | 2.4 | 3.9 | 2.1 | 0.017 | Lower |
| 2-41 | L234R/G236R | 1.2 | 3.9 | 10.7 | 5.2 | 0.014 | Lower |
| 2-42 | L234R/L235Q/G236R | −1.0 | 3.4 | 7.3 | 3.3 | 0.014 | Lower |
| 2-43 | L234R/L235R/G236R | −0.4 | 1.8 | pd | 0.7 | 0.016 | Lower |
| 2-44 | L234R/L235T/G236R | −0.8 | 3.9 | 25.1 | 9.4 | 0.008 | Lower |
| 2-45 | L234S/L235D/G236R | 4.3 | 7.2 | 20.5 | 10.6 | 0.010 | Lower |
| 2-46 | L234S/L235E/G236R | 3.7 | 5.3 | 6.9 | 5.3 | 0.019 | Lower |
| 2-47 | L234S/L235G/G236R | 2.6 | 1.5 | 3.7 | 2.6 | 0.018 | Lower |
| 2-48 | L234S/L235H/G236R | 0.4 | 1.1 | 3.9 | 1.8 | 0.017 | Lower |
| 2-49 | L234S/L235I/G236R | 3.9 | 4.2 | 6.4 | 4.8 | 0.019 | Lower |
| 2-50 | L234S/G236R | 33.7 | 21.6 | 30.9 | 28.7 | 0.034 | Lower |
| 2-51 | L234S/L235R/G236R | −1.1 | 1.9 | 1.6 | 0.8 | 0.017 | Lower |
| 2-52 | L234S/L235T/G236R | −0.5 | 0.3 | 1.9 | 0.6 | 0.017 | Lower |
| 2-53 | L234S/L235V/G236R | 0.7 | 2.1 | 4.3 | 2.4 | 0.017 | Lower |
| 2-54 | L234T/L235A/G236R | 4.3 | 4.8 | 7.2 | 5.4 | 0.019 | Lower |
| 2-55 | L234T/L235D/G236R | 6.0 | 28.9 | 62.3 | 32.4 | 0.145 | Equivalent |
| 2-56 | L234T/L235H/G236R | 1.4 | 7.4 | 60.9 | 23.2 | 0.123 | Equivalent |
| 2-57 | L234T/L235I/G236R | 7.2 | 17.3 | 24.2 | 16.2 | 0.014 | Lower |
| 2-58 | L234T/L235K/G236R | 1.1 | 2.4 | 4.5 | 2.7 | 0.017 | Lower |
| 2-59 | L234T/G236R | 156.0 | 105.3 | 139.7 | 133.6 | 0.029 | Higher |
| 2-60 | L234T/L235Q/G236R | 2.2 | 2.3 | 4.5 | 3.0 | 0.018 | Lower |
| 2-61 | L234T/L235R/G236R | 0.2 | 1.6 | 3.5 | 1.8 | 0.017 | Lower |
| 2-62 | L234T/L235S/G236R | 0.8 | 0.9 | 2.5 | 1.4 | 0.017 | Lower |
| 2-63 | L234T/L235T/G236R | 1.3 | 1.5 | Pd | 1.4 | 0.018 | Lower |
| 2-64 | L234T/L235V/G236R | 2.8 | 3.6 | 5.4 | 3.9 | 0.018 | Lower |
| 2-65 | L234A/L235A (LALA) | 781.7 | 581.7 | 675.1 | 679.5 | 0.008 | Higher |
| 2-66 | L234A/L235A/P329G (LALAPG reference) | 81.8 | 51.3 | 72.8 | 68.6 | 1.000 | Equivalent |
| 2-67 | N297Q (aglycosyl) | 744.6 | 491.6 | 578.1 | 604.8 | 0.017 | Higher |
| 2-68 | G236R/L328R | 8.8 | 24.9 | 65.0 | 32.9 | 0.154 | Equivalent |
| 2-69 | L234A/G237A | 255.2 | 175.7 | 222.2 | 217.7 | 0.014 | Higher |

TABLE 8-continued

Corrected binding responses of samples of purified antibodies binding to human FcγRI

| Sample | Amino acid alterations and Sample description | Corrected response (RU) | | | | P value | Compare with LALAPG |
|---|---|---|---|---|---|---|---|
| | | Expt 1 | Expt 2 | Expt 3 | Mean | | |
| 2-71 | L234A/L235E | 239.4 | 164.0 | 217.8 | 207.1 | 0.015 | Higher |
| 2-72 | L235V/F243L/R292P/Y300L/P396L | 2874.8 | 2370.4 | 2507.9 | 2584.4 | 0.003 | Higher |
| 2-73 | D265A/P329A | 1018.1 | 782.4 | 889.5 | 896.7 | 0.006 | Higher |
| 2-74 | L234A/L235A/K322A | 772.0 | 581.6 | 674.9 | 676.2 | 0.007 | Higher |
| 2-75 | L234F/L235E/P331S | 595.7 | 453.7 | 547.8 | 532.4 | 0.006 | Higher |
| 2-76 | L234F/L235Q/K322Q | 951.8 | 730.2 | 823.2 | 835.1 | 0.006 | Higher |
| 2-77 | L234A/L235A/G237A/P238S/H268A/A330S/P331S | 98.9 | 67.8 | 94.5 | 87.1 | 0.238 | Equivalent |
| 2-78 | E233P/L234V/L235A/G236Δ/A327G/A330S/P331S | 43.7 | 28.2 | 40.2 | 37.4 | 0.055 | Equivalent |
| 2-79 | L235A/G236R | 41.7 | 29.8 | 49.6 | 40.3 | 0.069 | Equivalent |
| 2-80 | L235S/G236R | 27.1 | 34.6 | 69.6 | 43.8 | 0.202 | Equivalent |
| 2-81 | G236R | 494.2 | 351.4 | 418.5 | 421.4 | 0.011 | Higher |
| 2-83 | L235G/G236R | 173.5 | 125.3 | 166.3 | 155.0 | 0.013 | Higher |
| 10.75 | L234A/L235A/P329G (LALAPG reference) | 67.8 | 45.7 | 65.9 | 59.8 | 0.488 | Equivalent |
| Buffer | Running buffer | −0.9 | −0.9 | −0.6 | −0.8 | 0.017 | Lower | nd = sample not done, pd = point dropped due to abnormal sensorgram.

This experiment shows that the binding to human FcγRI of many variants comprising amino acid substitutions at positions 234 and/or 235 together with the substitution G236R is significantly lower than the LALAPG reference antibody (p≤0.05). This result is particularly remarkable considering that the LALAPG reference antibody was previously described as having 'completely abolished FcγR interactions' (Schlothauer 2016). In stark contrast, none of the previously published variants (samples 2-65 and 2-67 to 2-83) give lower binding than the LALAPG reference antibody and many of them were significantly higher (p≤0.05).

Additional variants, including three produced from CHO cells, were tested in the same way. Results are shown in Table 9.

2.3 Binding to Mouse, Rat and Rabbit FcγRI Compared with Human FcγRI

A variant antibody with the amino acid alterations L234Q/L235S/G236R, representative of the new variants which gave very low binding to human FcγRI was compared with a set of controls for binding to mouse, rat and rabbit FcγRI. Binding analysis was carried out as described in Example 2.2 except that the chip was charged with either human FcγRI, mouse FcγRI (Sino Biological Cat. No. 50086-M08H), rat FcγRI (Sino Biological Cat. No. 80016-R08H) or rabbit FcγRI (Sino Biological Cat. No. 65010-T08H) each at 5 µg/mL. As before the binding responses were corrected by subtraction of the response given by a blank sample consisting of running buffer alone. The results are showing in Table 10. As before, the L234Q/L235S/G236R variant gave a substantially lower response than the LALAPG reference for binding to human FcγRI (2.0 RU compared with 72.9 RU). It also gave substantially lower binding to rabbit FcγRI (0.9 RU compared with 5.6 RU). Neither sample showed measurable binding to mouse or rat FcγRI.

TABLE 9

Corrected binding responses of samples of purified antibodies binding to human FcγRI.

| Sample | Amino acid alterations and Sample description | Corrected response (RU) | | | | Compare with LALAPG |
|---|---|---|---|---|---|---|
| | | Expt 1 | | Expt 2 | | |
| | | Rep 1 | Rep 2 | Rep 1 | Rep 2 | |
| Buffer | Running buffer (Blank subtraction cycle) | 0.0 | 0.0 | 0.0 | 0.0 | Lower |
| 2-66 | L234A/L235A/P329G (LALAPG reference) | 53.4 | 40.7 | 62.4 | 49.5 | Equivalent |
| 2-1 | wild type reference | 2371.3 | 2382.7 | 1462.9 | pd | Higher |
| 2-52 | L234S/L235T/G236R | −23.8 | −12.1 | −1.0 | pd | Lower |
| 2-65 | L234A/L235A | 752.3 | 654.0 | 524.0 | 477.7 | Higher |
| 2-85 | L234G/G236R | 8.7 | −5.9 | 18.7 | 11.9 | Lower |
| 2-86 | L235T/G236R | −9.4 | −10.6 | 2.0 | 0.0 | Lower |
| 2-87 | L234S/L235T | 62.9 | 54.1 | 72.8 | 62.4 | Higher |
| 2-1 (CHO) | wild type reference | 2121.3 | 2178.3 | 1353.1 | 1385.5 | Higher |
| 2-52(CHO) | L234S/L235T/G236R | −23.4 | −20.7 | −9.2 | −8.9 | Lower |
| 2-65(CHO) | L234A/L235A | 597.2 | 577.3 | 451.7 | 439.6 | Higher |

TABLE 10

Corrected binding responses of samples of purified antibodies binding to mouse, rat and rabbit FcγRI compared with binding to human FcγRI.

| Sample | Amino acid alterations and Sample description | Binding to FcγRI Corrected response (RU) | | | |
|---|---|---|---|---|---|
| | | human | mouse | rat | rabbit |
| Buffer | Running buffer (Blank subtraction cycle) | 0.0 | 0.0 | 0.0 | 0.0 |
| 10.0 | wild type reference | 3023.3 | 1789.7 | 2219.6 | 2770.4 |
| 10.16 | L234A/L235A (LALA) | 831.5 | 6.3 | 2.3 | 140.7 |
| 10.2 | N297Q (aglycosyl) | 578.3 | 49.3 | 1474.8 | 410.2 |
| 10.75 | L234A/L235A/P329G (LALAPG reference) | 72.9 | −0.2 | 0.5 | 5.6 |
| 10.77 | L234Q/L235S/G236R | 2.0 | 0.5 | 0.6 | 0.9 |
| Buffer | Running buffer | 2.1 | −1.5 | 0.1 | −4.1 |

2.4 Binding to Human FcγRII and Human FcγRIII

A variant antibody with the amino acid alterations L234Q/L235S/G236R, representative of the new variants which gave very low binding to human FcγRI was compared with a set of controls for binding to various forms of human FcγRII and human FcγRIII. Binding analysis was carried out as described in Example 2.2 except that the chip was charged with either human FcγRIIA (R131, Sino Biological Cat. No. 10374-H08H), human FcγRIIB (Sino Biological Cat. No. 10259-H08H), human FcγRIIIA (F158, Sino Biological Cat. No. 10389-H08H) or human FcγRIIIB (NA2 allotype, Sino Biological Cat. No. 11046-H08H). As before the binding responses were corrected by subtraction of the response given by a blank sample consisting of running buffer alone. The results are showing in Table 11. Neither the L234Q/L235S/G236R variant nor the LALAPG reference antibody showed measurable binding to any of the human FcγR in this experiment.

TABLE 11

Corrected binding responses of samples of purified antibodies binding to human FcγRIIA, FcγRIIB, FcγRIIIA and FcγRIIIB.

| Sample | Amino acid alterations and Sample description | Binding to human FcγR Corrected response (RU) | | | |
|---|---|---|---|---|---|
| | | FcγRIIA | FcγRIIB | FcγRIIIA | FcγRIIIB |
| Buffer | Running buffer (Blank subtraction cycle) | 0.0 | 0.0 | 0.0 | 0.0 |
| 10.0 | wild type reference | 345.2 | 175.3 | 888.6 | 500.8 |
| 10.16 | L234A/L235A (LALA) | 21.8 | 13.2 | 57.4 | 16.0 |
| 10.2 | N297Q (aglycosyl) | 9.4 | 2.9 | −1.4 | 1.0 |
| 10.75 | L234A/L235A/P329G (LALAPG reference) | 0.9 | −0.6 | −0.4 | −1.6 |
| 10.77 | L234Q/L235S/G236R | 1.8 | 1.0 | 1.0 | 2.3 |
| Buffer | Running buffer | 0.5 | −0.4 | −0.8 | 1.4 |

Further experiments were carried out in a similar way to measure the binding of a selection of variants to human FcγRIIIA. The results are shown in Table 12. Similar to the LALAPG reference antibody, the majority of the new variants showed very low binding to FcγRIIIA.

TABLE 12

Corrected binding responses of samples of purified antibodies binding to human FcγRIIIA.

| Sample | Amino acid alterations and Sample description | Binding to FcγRIIIA Corrected Response (RU) |
|---|---|---|
| Buffer | Running buffer (blank subtraction cycle) | 0.0 |
| 10.75 | L234A/L235A/P329G (LALAPG reference) | 7.6 |
| 2-1 | wild type reference | 588.0 |
| 2-4 | L234A/L235S/G236R | 6.0 |
| 2-7 | L234D/L235K/G236R | 3.7 |
| 2-19 | L234G/L235S/G236R | 5.8 |
| 2-23 | L234K/L235R/G236R | 7.1 |
| 2-24 | L234K/L235S/G236R | 7.3 |
| 2-25 | L234K/L235T/G236R | 4.0 |
| 2-26 | L234K/L235V/G236R | 5.5 |
| 2-27 | L234Q/L235A/G236R | 4.4 |
| 2-33 | L234Q/L235S/G236R | 2.7 |
| 2-34 | L234Q/L235T/G236R | 3.3 |
| 2-35 | L234Q/L235V/G236R | 4.7 |
| 2-36 | L234R/L235D/G236R | 4.9 |
| 2-37 | L234R/L235E/G236R | 4.6 |
| 2-38 | L234R/L235H/G236R | 3.9 |
| 2-39 | L234R/L235I/G236R | 2.7 |
| 2-40 | L234R/L235K/G236R | 4.4 |
| 2-43 | L234R/L235R/G236R | 10.2 |
| 2-47 | L234S/L235G/G236R | 3.8 |
| 2-48 | L234S/L235H/G236R | 3.7 |
| 2-51 | L234S/L235R/G236R | 2.4 |
| 2-52 | L234S/L235T/G236R | 2.8 |
| 2-53 | L234S/L235V/G236R | 2.9 |
| 2-58 | L234T/L235K/G236R | 3.5 |
| 2-60 | L234T/L235Q/G236R | 3.0 |
| 2-61 | L234T/L235R/G236R | 3.8 |
| 2-62 | L234T/L235S/G236R | 2.5 |
| 2-63 | L234T/L235T/G236R | 17.1 |
| 10.75 | L234A/L235A/P329G (LALAPG reference) | 2.7 |
| Buffer | Running buffer | 0.0 |

2.4 Further Binding to Fcγ Receptors

Additional studies were carried out to measure the binding of CD20, CD3 and CD52 IgG1 antibodies with the following mutations: L234G/L235S/G236R, L234S/L235T/G236R, L234S/L235T/G236R, L234S/L235V/G236R, L234T/L235Q/G236R, L234T/L235T/G236R, L234A/L235A (LALA), L234A/L235A/P329G (LALAPG reference) and N297Q (aglycosyl). Binding was measured by Biacore® analysis as described in Section 2.2 using the following receptors: human FcγRI, human FcγRIIa R131 allele, human FcγRIIb, human FcγRIIIa F158 allele, human FcγRIIIa V158 allele, human FcγRIIIb NA2 allele, mouse FcγRI, rat FcγRI. As before, the previously published variants LALA, LALAPG and aglycosyl all gave binding to FcγRI significantly above the negative control. The LALA variants also gave binding to FcγRII allele R131 and both alleles of FcγRIIIa significantly above the negative control. The aglycosyl variants gave substantial binding to both mouse and rat FcγRI which was significantly above the negative control. In contrast, the binding of all of the new variants to all of the FcγR was not significantly above the binding of the negative control.

Further experiments were carried out to measure the binding of CD20 antibodies with Fc regions from human IgG1, IgG2 and IgG4, mouse IgG2a, rat IgG2b and rabbit IgG. A representative variant L234Q/L235S/L236R was used for these studies. Wild-type human IgG2 has a deletion at residue 236. Two variants were made; in one the deletion was retained (L234Q/L235S) and in the other an Arg residue was inserted (L234Q/L235S/A236R). The variant IgG4 antibody included the stabilising mutation S228P. Two IgG1 variants also included mutations designed to increase binding to FcRn (L234Q/L235S/L236R/M252Y/S254T/T256E and L234Q/L235S/L236R/T250Q/M428L). Binding was measured by Biacore® analysis as described in Section 2.2 using the following receptors: human FcγRI, human FcγRIIa R131 allele, human FcγRIIb, human FcγRIIIa F158 allele, human FcγRIIIa V158 allele, human FcγRIIIb NA2 allele, mouse FcγRI, rat FcγRI. The IgG2 variant L234Q/L235S/A236R gave a weak positive binding response to human and mouse FcγRI. The IgG2 variant L234Q/L235S gave a stronger response to human FcγRI but was negative on mouse FcγRI. The IgG2 variants gave negative binding responses with all other Fcγ receptors tested. The rat IgG2b variant gave positive responses with human FcγRI, FcγRIIa R131, FcγRIIb, FcγRIIIa F158, and rat FcγRI but was negative with human FcγRIIIa V158 and mouse FcγRI. Variants based on human IgG4, mouse IgG2a, rabbit IgG and human IgG1 with half-life extending mutations gave negative binding responses with all of the Fcγ receptors tested.

Example 3 Binding to FcRn 3.1 Binding to FcRn by Surface Plasmon Resonance

A variant antibody with the amino acid alterations L234Q/L235S/G236R, representative of the new variants which gave very low binding to human FcγRI was compared with a set of controls for binding to human and monkey FcRn. Binding analysis was carried out as described in Example 2.2 except that the chip was charged with either human FcRn (R&D Systems Cat. No. 8639-Fc) at 5 μg/mL or cynomolgus monkey FcRn (Sino Biological Cat. No. CT031-C08H) at 2 μg/mL and the running buffer (HBS-EP+), which was also used for all sample dilutions, was adjusted with acetic acid to pH 6.0. Binding to human FcRn was measured twice. As before the binding responses were corrected by subtraction of the response given by a blank sample consisting of running buffer alone. The results are showing in Table 13. All of the samples gave substantial and broadly similar binding to both human and cynomolgus monkey FcRn.

TABLE 13

Corrected binding responses of samples of purified antibodies binding to human and cynomolgus FcRn.

| | | Binding to FcRn Corrected response (RU) | | |
|---|---|---|---|---|
| Sample | Amino acid alterations and Sample description | human Expt 1 | human Expt 2 | cynomolgus |
| Buffer | Running buffer (Blank subtraction cycle) | 0.0 | 0.0 | 0.0 |
| 10.0 | wild type reference | 647.4 | 649.6 | 1443.5 |
| 10.16 | L234A/L235A (LALA) | 612.2 | 614.2 | 1387.9 |
| 10.2 | N297Q (aglycosyl) | 426.3 | 429.6 | 1040.5 |
| 10.75 | L234A/L235A/P329G (LALAPG reference) | 542.6 | 556.6 | 1274.3 |
| 10.77 | L234Q/L235S/G236R | 488.2 | 495.9 | 1173.1 |
| Buffer | Running buffer | 3.3 | 2.9 | 2.6 |

Further experiments were carried out in a similar way to measure the binding of a selection of variants to human FcRn, cynomolgus FcRn and mouse FcRn (Sino Biological Cat. No. CT029-MOSH). The results are shown in Table 14. All variants gave generally similar responses compared with the wild-type reference antibody.

TABLE 14

Corrected binding responses of samples of purified antibodies binding to human, cynomolgus and mouse FcRn.

| | | Binding to FcRn Corrected response (RU) | | |
|---|---|---|---|---|
| Sample | Amino acid alterations and Sample description | human | cynomolgus | mouse |
| Buffer | Running buffer (Blank subtraction cycle) | 0.0 | 0.0 | 0.0 |
| 10.75 | L234A/L235A/P329G (LALAPG reference) | 488.0 | 1141.2 | 138.9 |
| 2-1 | wild type reference | 581.8 | 1319.2 | 177.6 |
| 2-4 | L234A/L235S/G236R | 538.9 | 1263.8 | 146.4 |
| 2-10 | L234D/L235S/G236R | 507.3 | 1202.7 | 144.6 |
| 2-27 | L234Q/L235A/G236R | 512.8 | 1216.7 | 153.9 |
| 2-28 | L234Q/L235D/G236R | 489.5 | 1162.1 | 170.2 |
| 2-32 | L234Q/L235R/G236R | 533.2 | 1238.3 | 179.6 |
| 2-33 | L234Q/L235S/G236R | 534.8 | 1233.0 | 165.8 |
| 2-43 | L234R/L235R/G236R | 570.2 | 1296.9 | 180.6 |
| 2-65 | L234A/L235A | 504.8 | 1179.6 | 189.7 |
| 2-66 | L234A/L235A/P329G (LALAPG reference) | 509.4 | 1181.7 | 175.5 |
| 2-67 | N297Q (aglycosyl) | 420.6 | 1013.1 | 163.1 |
| 2-68 | G236R/L328R | 567.2 | 1288.6 | 205.7 |
| 2-79 | L235A/G236R | 540.1 | 1236.2 | 168.0 |
| 2-80 | L235S/G236R | 530.0 | 1219.9 | 188.8 |
| 2-81 | G236R | 569.8 | 1290.5 | 172.7 |
| 2-82 | L234Q/L235S/L236G | 508.6 | 1173.0 | 141.5 |
| 2-83 | L235G/G236R | 546.6 | 1248.5 | 145.9 |
| 10.75 | L234A/L235A/P329G (LALAPG reference) | 461.1 | 1053.0 | 115.7 |
| Buffer | Running buffer | 2.7 | 3.9 | −18.2 |

Further experiments were carried out to test a larger panel of variants for binding to human FcRn. Because of the comparatively large number of samples, it was necessary to correct for the effects of baseline drift and loss of binding capacity during the runs which required repeated regeneration of the Biacore® chip. A baseline correction was calculated by interpolating the response of two blank samples, one at the beginning and one at the end of the run, to determine an individual baseline correction for each cycle which was subtracted from the response of the sample run in that cycle. To correct for loss of binding capacity, a normalization factor was calculated by interpolating the response of reference samples 10.75 (LALAPG reference) at the beginning and end of the run to determine an individual normalisation factor for each cycle. The baseline-corrected responses were then divided by the normalisation factor to give corrected and normalised responses which were expressed as a percentage of the interpolated response of the wild-type reference. The whole experiment was carried out three times and the results are shown in Table 15. With the exception of sample 2-67 (N297Q, aglycosyl), all of the variants gave normalised responses within 93% to 108% of the response of the wild-type reference (sample 2-1).

TABLE 15

Corrected and normalised binding responses of samples of purified antibodies binding to human FcRn.

| Sample | Amino Acid Alterations and sample description | Binding to human FcRn Corrected and normalised response (% of wild-type reference) | | | |
|---|---|---|---|---|---|
| | | Expt 1 | Expt 2 | Expt 3 | Mean |
| 2-1 | wild type reference | 100.0 | 100.0 | 100.0 | 100.0 |
| 2-4 | L234A/L235S/G236R | 96.5 | 95.7 | 95.8 | 96.0 |
| 2-7 | L234D/L235K/G236R | 94.9 | 93.7 | 94.1 | 94.3 |
| 2-19 | L234G/L235S/G236R | 97.1 | 96.0 | 95.7 | 96.3 |
| 2-23 | L234K/L235R/G236R | 100.9 | 99.6 | 99.5 | 100.0 |
| 2-24 | L234K/L235S/G236R | 100.5 | 99.7 | 100.1 | 100.1 |
| 2-25 | L234K/L235T/G236R | 102.6 | 102.6 | 102.3 | 102.5 |
| 2-26 | L234K/L235V/G236R | 101.0 | 100.4 | 100.4 | 100.6 |
| 2-27 | L234Q/L235A/G236R | 94.5 | 93.4 | 92.8 | 93.5 |
| 2-30 | L234Q/G236R | 100.0 | 99.0 | 99.0 | 99.3 |
| 2-33 | L234Q/L235S/G236R | 98.4 | 97.8 | 98.2 | 98.1 |
| 2-34 | L234Q/L235T/G236R | 95.6 | 95.1 | 95.2 | 95.3 |
| 2-35 | L234Q/L235V/G236R | 97.3 | 96.6 | 97.4 | 97.1 |
| 2-36 | L234R/L235D/G236R | 95.5 | 95.4 | 96.0 | 95.6 |
| 2-37 | L234R/L235E/G236R | 99.0 | 98.6 | 97.8 | 98.4 |
| 2-38 | L234R/L235H/G236R | 102.2 | 102.2 | 101.7 | 102.0 |
| 2-39 | L234R/L235I/G236R | 103.5 | 103.6 | 103.4 | 103.5 |
| 2-40 | L234R/L235K/G236R | 105.0 | 106.0 | 105.5 | 105.5 |
| 2-43 | L234R/L235R/G236R | 106.4 | 108.3 | 107.8 | 107.5 |
| 2-47 | L234S/L235G/G236R | 100.0 | 101.1 | 100.5 | 100.5 |
| 2-48 | L234S/L235H/G236R | 100.4 | 102.0 | 100.8 | 101.1 |
| 2-51 | L234S/L235R/G236R | 99.8 | 101.9 | 100.9 | 100.9 |
| 2-52 | L234S/L235T/G236R | 98.3 | 97.9 | 93.7 | 96.6 |
| 2-53 | L234S/L235V/G236R | 96.5 | 97.8 | 96.8 | 97.0 |
| 2-58 | L234T/L235K/G236R | 99.2 | 100.5 | 100.2 | 100.0 |
| 2-60 | L234T/L235Q/G236R | 94.6 | 96.1 | 94.3 | 95.0 |
| 2-61 | L234T/L235R/G236R | 101.1 | 103.5 | 103.0 | 102.5 |
| 2-62 | L234T/L235S/G236R | 96.8 | 98.3 | 97.0 | 97.4 |
| 2-63 | L234T/L235T/G236R | 96.0 | 95.1 | 88.1 | 93.0 |
| 2-65 | L234A/L235A (LALA) | 92.8 | 94.2 | 92.9 | 93.3 |
| 2-66 | L234A/L235A/P329G (LALAPG reference) | 95.1 | 96.4 | 93.6 | 95.1 |
| 2-67 | N297Q (aglycosyl) | 78.4 | 78.7 | 76.6 | 77.9 |
| 2-74 | L234A/L235A/K322A | 94.0 | 94.7 | 93.3 | 94.0 |

TABLE 15-continued

Corrected and normalised binding responses of samples of purified antibodies binding to human FcRn.

| Sample | Amino Acid Alterations and sample description | Binding to human FcRn Corrected and normalised response (% of wild-type reference) | | | |
|---|---|---|---|---|---|
| | | Expt 1 | Expt 2 | Expt 3 | Mean |
| 2-75 | L234F/L235E/P331S | 96.1 | 97.1 | 96.3 | 96.5 |
| 2-76 | L234F/L235Q/K322Q | 95.8 | 97.0 | 96.1 | 96.3 |

3.2 Binding to FcRn by NanoBiT® Immunoassay

An alternative way to measure binding to FcRn in solution uses a luminescence assay. NanoBiT® FcRn Immunoassay (Promega) is a homogeneous (no-wash) competition assay to measure the interaction between human FcRn and Fc proteins including antibodies. Human IgG labelled with LgBiT (Tracer-LgBiT) is used as the tracer. A C-terminus biotinylated FcRn attached to Streptavidin-SmBIT (FcRn-SAv-SmBIT) is used as the target. In the presence of sample containing no IgG, Tracer-LgBiT binds to the FcRn-SAv-SmBIT target resulting in maximum luminescence signal. For samples containing IgG, unlabelled IgG will compete with Tracer-LgBiT for binding to the target, resulting in concentration dependent decrease in luminescent signal. The experiment was carried out using a NanoBiT® FcRn Immunoassay kit (Promega Cat. No. CS53019A) according to the manufacturer's instruction. Samples were diluted in an offline plate; 25 µL of each test sample (1 mg/mL in PBS) was mixed with 2.5 L of pH adjustment buffer and 72.5 µL FcRn assay buffer to give a concentration of 250 µg/mL at pH 6.0. Four-fold dilutions of the positive control antibody (human IgG) were prepared, starting at 4 mg/mL. 25 µL of Tracer-LgBiT was added to each well of a white microplate (Sigma Cat. No. CLS3912), followed by 25 µL of samples (in duplicate). The plate was briefly mixed on a plate shaker and 50 µL of streptavidin-SmBiT plus hFcRn-AviTag was added to each well. The plate was incubated on the shaker at room temperature for 2.5 h. 25 µL of FcRn NanoGlo® substrate was added and after 5 min, the luminescence was measured in a Veritas Microplate Luminometer (Turner BioSystems). The calibration curve is shown in FIG. 2. The raw data were fitted to a 5-parameter logistic equation and nominal concentrations of the test samples were calculated by interpolation on the standard curve. The nominal concentrations indicate the concentration of positive control antibody which would give the same inhibition. The mean results were expressed as a percentage of the nominal concentration of the wild-type reference and are shown in Table 16.

TABLE 16

Binding activity samples of purified antibodies in an FcRn inhibition assay.

| Sample | Amino acid alterations and Sample Description | Target | Species | Isotype | Mean binding activity (% of wild-type reference) |
|---|---|---|---|---|---|
| 10.0 | wild type reference | CD20 | human | IgG1 | (100) |
| 2-19 | L234G/L235S/G236R | CD20 | human | IgG1 | 77.8 |
| 2-52 | L234S/L235T/G236R | CD20 | human | IgG1 | 98.6 |
| 2-53 | L234S/L235V/G236R | CD20 | human | IgG1 | 94.1 |
| 2-60 | L234T/L235Q/G236R | CD20 | human | IgG1 | 84.7 |
| 2-63 | L234T/L235T/G236R | CD20 | human | IgG1 | 149.7 |
| 2-65 | L234A/L235A (LALA) | CD20 | human | IgG1 | 70.1 |
| 2-66 | L234A/L235A/P329G (LALAPG reference) | CD20 | human | IgG1 | 96.7 |
| 2-67 | N297Q (aglycosyl) | CD20 | human | IgG1 | 34.1 |
| 11.77 | L234Q/L235S/A236R | CD20 | human | IgG2 | 189.2 |
| 11.144 | L234Q/L235S | CD20 | human | IgG2 | 143.1 |

TABLE 16-continued

Binding activity samples of purified antibodies in an FcRn inhibition assay.

| Sample | Amino acid alterations and Sample Description | Target | Species | Isotype | Mean binding activity (% of wild-type reference) |
|---|---|---|---|---|---|
| 13.77 | L234Q/L235S/G236R | CD20 | human | IgG4 | 114.5 |
| 2.77 | L234Q/L235S/G236R | CD20 | mouse | IgG2a | <1.0 |
| 8.77 | L234Q/L235S/G236R | CD20 | rat | IgG2b | <1.0 |
| 23.77 | L234Q/L235S/G236R | CD20 | rabbit | IgG | 146.6 |
| 10.145 | L234Q/L235S/G236R/ M252Y/S254T/T256E | CD20 | human | IgG1 | 3944.9 |
| 10.146 | L234Q/L235S/G236R T250Q/M428L | CD20 | human | IgG1 | 650.5 |

Consistent with earlier results (Example 3.1), the aglycosyl antibody (2-67) showed reduced binding activity. There was no detectable binding activity for 2.77 (mouse IgG2a) and 8.77 (rat IgG2b). Variants 2-63 (L234T/L235T/G236R), 11.77 (IgG2 L234Q/L235S/A236R), 11.144 (IgG2 L234Q/L235S) and 23.77 (rabbit IgG) showed increased binding activity. The two variants which included additional mutations designed to enhance binding to FcRn (10.145 and 10.146) did indeed show substantially higher binding activity. The binding activity of other variants was within +30% of the wild-type reference.

Overall, these experiments demonstrate that the new variants have minimal, if any effect on binding to FcRn.

Example 4 Binding to C1q

Human C1q (Sigma Cat. No. 20476) was coupled to horse-radish peroxidase (HRP) using Lightning-Link® HRP Conjugation Kit (Innova Biosciences Cat No 701-0003) as follows: 2 µL of Lightning-Link® modifier was gently mixed with 20 µL of C1q at 1.15 mg/mL. The mixture was added to lyophilised Lightning-Link® HRP (sufficient for up to 40 µg protein) and gently mixed. The mixture was incubated for 3 hours at 4° C. 2 µL of Lightning-Link® quencher was added and incubated for 30 min at 4° C. The resulting HRP-labelled C1q was diluted to 20 µg/mL with phosphate-buffered saline (PBS) containing 1% casein (block buffer) and stored at 4° C.

Binding analysis was carried out by ELISA. All steps were carried out at room temperature (18 to 22° C.). Samples of purified antibodies comprising variant Fc regions were diluted to 10 µg/mL in PBS. Negative controls consisted of PBS alone. Replicates of 100 µL each were added to two 96-well clear Maxisorp microplates (Sigma Cat. No. M9410-ICS) and incubated with shaking for approximately 60 min. The plates were rinsed with PBS containing 0.05% (v/v) Tween 20 (wash buffer) and 200 µL block buffer was added. The plates were incubated with shaking for approximately 60 min and optionally stored overnight at 4° C., then rinsed with wash buffer. HRP-labelled C1q was diluted to 100 ng/mL in block buffer and 100 µL was added to each well. The plates were incubated with shaking for approximately 90 min then washed four times with wash buffer and twice with water. 100 UL of 3,3',5,5'-tetramethylbenzidine liquid substrate, supersensitive (TMB) (Sigma Cat. No. T4444) was added and the plates were incubated with shaking for approximately 10 min. 50 µL of 1M sulphuric acid was added to stop the reaction and the absorbance was read at 450 nm with 620 nm subtraction using a microplate spectrophotometer (Anthos Labtec HT). The whole experiment was repeated three times using different selections of variant antibodies. In experiments 1 and 2, six replicates of each sample were tested (three on each plate) and in experiment 3, twelve replicates (six on each plate). The mean absorbance of each sample was calculated and is shown in Table 17. Within each experiment, the mean absorbance for each sample was compared with the mean absorbance obtained with buffer alone using a one-tailed t-test, assuming unequal variances. The mean of the resulting probability (P) values was calculated. Results were flagged if they were significantly higher (p≤0.05) than the response for buffer alone. Results are shown in Table 17. All of the new variants (Samples 2-2 to 2-63) and controls (2-65, 2-66 and 2-67) with the exception of 2-25 (L234K/L235T/G236R) and 2-39 (L234R/L235I/G236R), could not be distinguished from buffer alone with respect to binding to C1q.

TABLE 17

Mean binding responses of samples of purified antibodies binding to human C1q.

| | | Mean Absorbance (number of replicates) | | | |
|---|---|---|---|---|---|
| Sample | Amino acid alterations and Sample Description | Expt 1 (6) | Expt 2 (6) | Expt 3 (12) | Mean P value |
| Buffer | PBS | 0.061 | 0.091 | 0.102 | n/a |
| 2-1 | wild type reference | 2.629 | 2.212 | 1.881 | 0.000 |
| 2-4 | L234A/L235S/G236R | 0.041 | 0.100 | 0.095 | ns |
| 2-7 | L234D/L235K/G236R | 0.049 | nd | nd | ns |
| 2-19 | L234G/L235S/G236R | 0.052 | 0.091 | 0.064 | ns |
| 2-23 | L234K/L235S/G236R | 0.059 | nd | nd | ns |
| 2-24 | L234K/L235S/G236R | 0.096 | nd | nd | ns |
| 2-25 | L234K/L235T/G236R | 0.096 | nd | nd | 0.036 |
| 2-26 | L234K/L235V/G236R | 0.073 | nd | nd | ns |
| 2-27 | L234Q/L235A/G236R | 0.048 | nd | nd | ns |
| 2-30 | L234Q/G236R | nd | 0.089 | nd | ns |
| 2-33 | L234Q/L235S/G236R | 0.026 | 0.084 | 0.083 | ns |
| 2-34 | L234Q/L235T/G236R | 0.034 | nd | nd | ns |
| 2-35 | L234Q/L235V/G236R | 0.032 | nd | nd | ns |
| 2-36 | L234R/L235D/G236R | 0.038 | nd | nd | ns |
| 2-37 | L234R/L235E/G236R | 0.048 | nd | nd | ns |
| 2-38 | L234R/L235H/G236R | 0.062 | nd | nd | ns |
| 2-39 | L234R/L235I/G236R | 0.169 | nd | nd | 0.020 |
| 2-40 | L234R/L235K/G236R | 0.055 | nd | nd | ns |
| 2-43 | L234R/L235R/G236R | 0.029 | nd | nd | ns |
| 2-47 | L234S/L235G/G236R | 0.034 | 0.074 | 0.087 | ns |
| 2-48 | L234S/L235H/G236R | 0.040 | nd | nd | ns |
| 2-51 | L234S/L235R/G236R | 0.037 | nd | nd | ns |
| 2-52 | L234S/L235T/G236R | 0.047 | 0.079 | 0.083 | ns |
| 2-53 | L234S/L235V/G236R | 0.072 | 0.090 | 0.097 | ns |
| 2-58 | L234T/L235K/G236R | 0.126 | nd | nd | ns |
| 2-60 | L234T/L235Q/G236R | 0.049 | 0.077 | 0.134 | ns |
| 2-61 | L234T/L235R/G236R | 0.047 | nd | nd | ns |
| 2-62 | L234T/L235S/G236R | 0.037 | 0.067 | 0.119 | ns |
| 2-63 | L234T/L235T/G236R | 0.068 | 0.077 | 0.095 | ns |
| 2-65 | L234A/L235A (LALA) | nd | 0.078 | 0.080 | ns |
| 2-66 | L234A/L235A/P329G (LALAPG reference) | nd | 0.080 | 0.103 | ns |
| 2-67 | N297Q (aglycosyl) | nd | 0.076 | 0.083 | ns | nd = not done.
ns = not significant (p > 0.05)

The above experiments were carried out using variants with variable regions derived from the anti-CD20 antibody rituximab. Additional experiments were carried out using variants with variable regions derived from the anti-CD3 antibody muromonab (OKT3) or the anti-CD52 antibody alemtuzumab as well as other variants based on different immunoglobulin species and isotypes in order to demonstrate the generality of the above results.

Binding analysis was carried out by ELISA following essentially the same method as previously described. Variations such as an alternative source of microplates (Sigma Cat. No. CLS 9018) and TMB substrate (Abcam Cat. No. ab171523) and an extended incubation (overnight) with HRP-labelled C1q did not make a material difference to the results. Samples were tested in triplicate on two microplates (6 replicates in total). The mean absorbance for each sample was compared with the mean absorbance obtained with buffer alone using a one-tailed t-test, assuming unequal variances and the resulting probability (P) values were calculated. Results were flagged if they were significantly higher ($p \leq 0.05$) than the response for buffer alone. The experiment was carried out twice and the results are presented in Table 18 with the mean P values. Results for the variant anti-CD3 and anti-CD52 antibodies were consistent with the previous results for variant anti-CD20 antibodies. Their binding to C1q was not significantly greater than buffer alone (p>0.05), except for variants 4-63 (anti-CD52 L234T/L235T/G236R), 4-65 (anti-CD52 L234A/L235A) and 4-66 (anti-CD52 L234A/L235A/P329G) which gave responses very slightly above the response of buffer alone. Furthermore, there was no significant difference between the binding to C1q of the new variants and the binding of the corresponding LALAPG reference. The binding to C1q was not significantly greater than buffer alone for human IgG2 having the alterations L234Q/L235S/A236R and for human IgG4 and rabbit IgG having the alterations L234Q/L235S/G236R. Human IgG2 with only two alterations L234Q/L235S showed a slightly increased binding (p=0.017), as did rat IgG2b with three alterations L234Q/L235S/G236R (p=0.008). In contrast, mouse IgG2a with the same three alterations L234Q/L235S/G236R, gave a level of C1q binding which was comparable with wild-type human IgG1. This is consistent with previous observations indicating that the binding site for C1q on mouse IgG is different from that on human IgG (Idusogie 2000). Finally, the combination of the alterations L234Q/L235S/G236R with two different sets of alterations that result in increased binding to FcRn, namely M252Y/S254T/T256E or T250Q/M428L, still resulted in binding to C1q which was not significantly greater than buffer alone.

TABLE 18

Mean binding responses of samples of purified antibodies binding to human C1q.

| Sample | Amino acid alterations and Sample Description | Target | Species | Isotype | Mean Absorbance (number of replicates) Expt 1 (6) | Mean Absorbance (number of replicates) Expt 2 (6) | Mean P value |
|---|---|---|---|---|---|---|---|
| Buffer | PBS | | | | 0.053 | 0.051 | n/a |
| 3-1 | wild type reference | CD3 | human | IgG1 | 0.769 | 0.432 | 0.000 |
| 3-19 | L234G/L235S/G236R | CD3 | human | IgG1 | 0.052 | 0.049 | ns |
| 3-52 | L234S/L235T/G236R | CD3 | human | IgG1 | 0.048 | 0.046 | ns |
| 3-53 | L234S/L235V/G236R | CD3 | human | IgG1 | 0.047 | 0.042 | ns |
| 3-60 | L234T/L235Q/G236R | CD3 | human | IgG1 | 0.047 | 0.045 | ns |
| 3-63 | L234T/L235T/G236R | CD3 | human | IgG1 | 0.047 | 0.048 | ns |
| 3-65 | L234A/L235A (LALA) | CD3 | human | IgG1 | 0.053 | 0.051 | ns |
| 3-66 | L234A/L235A/P329G (LALAPG reference) | CD3 | human | IgG1 | 0.052 | 0.044 | ns |
| 3-67 | N297Q (aglycosyl) | CD3 | human | IgG1 | 0.052 | 0.051 | ns |
| 4-1 | wild type reference | CD52 | human | IgG1 | 1.423 | 0.649 | 0.000 |
| 4-19 | L234G/L235S/G236R | CD52 | human | IgG1 | 0.053 | 0.056 | ns |
| 4-52 | L234S/L235T/G236R | CD52 | human | IgG1 | 0.052 | 0.053 | ns |
| 4-53 | L234S/L235V/G236R | CD52 | human | IgG1 | 0.057 | 0.059 | ns |
| 4-60 | L234T/L235Q/G236R | CD52 | human | IgG1 | 0.056 | 0.052 | ns |
| 4-63 | L234T/L235T/G236R | CD52 | human | IgG1 | 0.058 | 0.058 | 0.011 |
| 4-65 | L234A/L235A (LALA) | CD52 | human | IgG1 | 0.062 | 0.058 | 0.006 |
| 4-66 | L234A/L235A/P329G (LALAPG reference) | CD52 | human | IgG1 | 0.059 | 0.057 | 0.026 |
| 4-67 | N297Q (aglycosyl) | CD52 | human | IgG1 | 0.051 | 0.044 | ns |
| 10.0 | wild type reference | CD20 | human | IgG1 | 1.829 | 1.335 | 0.000 |
| 11.77 | L234Q/L235S/D236R | CD20 | human | IgG2 | 0.052 | 0.049 | ns |
| 11.144 | L234Q/L235S | CD20 | human | IgG2 | 0.063 | 0.057 | 0.017 |
| 13.77 | L234Q/L235S/G236R | CD20 | human | IgG4 | 0.051 | 0.052 | ns |
| 2.77 | L234Q/L235S/G236R | CD20 | mouse | IgG2a | 1.453 | 0.953 | 0.002 |
| 8.77 | L234Q/L235S/G236R | CD20 | rat | IgG2b | 0.065 | 0.056 | 0.008 |
| 23.77 | L234Q/L235S/G236R | CD20 | rabbit | IgG | 0.051 | 0.048 | ns |
| 10.145 | L234Q/L235S/G236R/ M252Y/S254T/T256E | CD20 | human | IgG1 | 0.052 | 0.056 | ns |
| 10.146 | L234Q/L235S/G236R T250Q/M428L | CD20 | human | IgG1 | 0.051 | 0.062 | ns | ns = not significant (p > 0.05).

The results from this set of experiments demonstrate the generality of the amino acid alterations we have discovered, since they reduce the binding of C1q to an undetectable level in a wide variety of different settings, including in the context of different variable regions, different IgG subclasses, different species and in combinations with other amino acid alterations that are commonly introduced into IgG.

Example 5 in Silico Assessment of Potential
Binding to MHC Class II

The potential for variant Fc regions to give rise to peptides with the theoretical capacity to bind to human major histocompatibility complex class 2 (MHC Class II) was assessed using the MHC-II Binding Predictions tool provided by the Immune Epitope Database (IEDB) (Fleri 2017), available at the website of the Immune Epitope Database (accessed 17 Oct. 2019). The prediction method was IEDB recommended version 2.22. This used a Consensus method, version 2.22 combining NN-align (Jensen 2018), SMM-align (Nielson 2007), CombLib (Sidney 2008) and Sturniolo (Sturniolo 1999) if any corresponding predictor was available for the molecule, otherwise NetMHCIIpan (Jensen 2018) was used.

The input consisted of a list of 361 peptides in FASTA format, corresponding to amino acid residues C220 to T250 (inclusive) of human IgG1 with any residue at positions 234 and 235 other than C, and position 236 substituted by R. A "7-allele" reference set of MHC Class II alleles was selected (Paul 2015). This consists of the following alleles: DRB1*03:01, DRB1*07:01, DRB1*15:01, DRB3*01:01, DRB3*02:02, DRB4*01:01, DRB5*01:01. The default peptide epitope length of 15 amino acid residues was selected. The output was sorted by the rank score and presented as an XHTML table. The data were exported to a Microsoft Excel® file for further processing. An Fc variant was considered "at risk" of producing new peptides which might bind to MHC Class II if any one of the possible 15-mer peptides which might be derived from the 31-residue input peptides gave a rank score of 10% or less for binding to any of the selected alleles. The whole process was repeated with the full reference set of 27 MHC Class II alleles (Greenbaum 2011). The results are shown in Table 19. The presence of hydrophobic amino acid residues F, I, L, M, V, W, or Y at position 234 and/or F, W, Y at position 235 were associated with an increased risk of creating new peptides which might bind to MHC Class II and therefore a potentially increased risk of unwanted immunogenicity.

reference set and "A" indicates that at least one peptide gave a rank score≤10% with one or more alleles from the 27-allele reference set. A blank indicates that no peptide gave a rank score≤ 10% with any allele.

Example 6 Activity in ADCC and ADCP 6.1 ADCC Using FcγRIIIA

Antibodies were assessed for their ability to engage in ADCC using an ADCC Reporter Bioassay (Promega Cat. No. G7015). The kit contains Raji target cells which express CD20 antigen and engineered Jurkat effector cells which stably express the FcγRIIIA receptor, V158 (high affinity) variant and a nuclear factor of activated T-cells (NFAT) response element which can drive expression of firefly luciferase. This allows the sensitive measurement of an early response in the ADCC pathway, namely the activation of gene transcription through NFAT. Experiments were carried out in accordance with the manufacturer's instructions. Target cells (Promega Cat. No. G960A) and effector cells (Promega Cat. No. G701A) and sample dilutions were all prepared in RPMI1640 culture medium (Promega Cat. No. G708A) containing 4% low IgG serum (Promega Cat. No. G711A) (assay buffer). 75 µL of assay buffer was added to the edge wells of a white, flat-bottomed microplate (Costar Cat. No. 3912) and 25 µL of target cell suspension was added to the central wells. Sample dilutions were prepared as required in an off-line plate; 25 µL was transferred to the central wells of the assay plate and mixed on a plate shaker. 25 µL of effector cell suspension was added and mixed and the plate was incubated at 37° C. in 5% $CO_2$ for approximately 6 hours, then equilibrated at room temperature for approximately 15 min. Luciferase assay substrate (Promega Cat. No. G720A) was reconstituted by addition of luciferase assay buffer (Promega Cat. No. G719A), equilibrated to room temperature and 75 µL was added to the central wells of the microplate. Luminescence was measured within 10 min using a microplate luminometer (Promega Glomax® 96).

TABLE 19

Indication of the potential of amino acid substitutions at positions 234 and 235 to create peptides which are more likely to bind to MHC Class II.

| | | Residue at position 235 | | | | | | | | | | | | | | | | | |
|---|---|---|---|---|---|---|---|---|---|---|---|---|---|---|---|---|---|---|---|
| | | A | D | E | F | G | H | I | K | L | M | N | P | Q | R | S | T | V | W | Y |
| Residue at position 234 | A | | | | 7 | | | | | | | | | | | | | | 7 | 7 |
| | D | | | | 7 | | | | | | | | | | | | | | | 7 |
| | E | | | | 7 | | | | | | | | | | | | | | 7 | 7 |
| | F | 7 | 7 | 7 | 7 | 7 | 7 | 7 | 7 | 7 | 7 | 7 | | 7 | 7 | 7 | 7 | 7 | 7 | 7 |
| | G | | | | 7 | | | | | | | | | | | | | | | 7 |
| | H | | | | 7 | | | | | | | | | | | | | | 7 | 7 |
| | I | A | | | 7 | | A | 7 | 7 | 7 | 7 | 7 | | 7 | 7 | 7 | 7 | 7 | 7 | 7 |
| | K | | | | 7 | | | | | | | | | | | | | | 7 | 7 |
| | L | | | | 7 | | 7 | 7 | 7 | 7 | 7 | 7 | | 7 | 7 | 7 | 7 | 7 | 7 | 7 |
| | M | | | | 7 | | A | | A | A | | A | | | 7 | | | 7 | 7 | 7 |
| | N | | | | 7 | | | | | | | | | | | | | | | 7 |
| | P | | | | 7 | | | | | | | | | | | | | | | 7 |
| | Q | | | | 7 | | | | | | | | | | | | | | 7 | 7 |
| | R | | | | 7 | | | | | | | | | | | | | | 7 | 7 |
| | S | | | | 7 | | | | | | | | | | | | | | | 7 |
| | T | | | | 7 | | | | | | | | | | | | | | 7 | 7 |
| | V | | | | 7 | | A | A | A | | A | | | | 7 | | | 7 | 7 | 7 |
| | W | A | | A | 7 | A | A | 7 | 7 | A | 7 | 7 | | 7 | 7 | 7 | 7 | 7 | 7 | 7 |
| | Y | 7 | 7 | | 7 | | | 7 | 7 | 7 | 7 | 7 | | 7 | 7 | 7 | 7 | 7 | 7 | 7 |

In this table, "7" indicates that at least one peptide gave a rank score≤10% with one or more alleles from the 7-allele The whole experiment was carried out twice using two microplates per experiment. On each plate the wild-type reference anti-CD20 antibody (Sample 2-1) was titrated from a starting concentration of 3 µg/mL (1 µg/mL final in the assay), followed by 2.5-fold dilutions to determine the dose response. The dose-response curves are shown in FIG. 3. They indicate that the assay performance was satisfactory. Test samples were diluted to 30 µg/mL (10 µg/mL final in the assay). All controls and test samples were tested in duplicate. Normalised responses were expressed as a percentage of the response of the wild-type reference antibody at 1 µg/mL final in the same microplate. The mean of the normalised response for each sample across the four repeats was compared with the mean of the normalised response for Assay buffer using a one-tailed t-test, assuming unequal variances. Results were flagged if they were significantly higher ($p \leq 0.05$) than the normalised response for Assay buffer. Results are shown in Table 20. All of the new variants (Samples 2-2 to 2-64 inclusive) with the exception of 2-25 (L234K/L235T/G236R) and 2-36 (L234R/L235D/G236R) gave responses indistinguishable from the Assay buffer. In contrast, previously published variants 2-65 (L234A/L235A), 2-75 (L234F/L235E/P331S) and 2-76 (L234F/L235Q/K322Q) gave significantly higher responses compared with Assay buffer.

6.2 ADCP Using FcγRIIA

Antibodies were assessed for their ability to engage in ADCP using an ADCP Reporter Bioassay (Promega Cat. No. G9901). The kit contains Raji target cells which express CD20 antigen and engineered Jurkat effector cells which stably express the FcγRIIA receptor, H131 variant and a nuclear factor of activated T-cells (NFAT) response element which can drive expression of firefly luciferase. The assay was carried out according to the manufacturer's instructions as described in Example 6.1, using FcγRIIA-H effector cells (Promega Cat. No. G988A). The experiment was carried out once, with each sample being tested in duplicate. Normalised responses were calculated as described in Example 6.1. The dose response curve for titration of wild-type reference antibody (Sample 2-1) is shown in FIG. 4. The results are shown in Table 21. All of the new variants (Samples 2-2 to 2-64 inclusive) with the exception of 2-25 (L234K/L235T/G236R), 2-30 (L234Q/G236R), 2-36 (L234R/L235D/G236R) and 2-58 (L234T/L235K/G236R) gave responses which were not significantly different from the Assay buffer. In contrast, previously published variants 2-65 (L234A/L235A), 2-75 (L234F/L235E/P331S) and 2-76 (L234F/L235Q/K322Q) gave significantly higher responses compared with Assay buffer.

TABLE 20

Normalised responses of samples of purified antibodies in an ADCC assay.

| Sample | Amino acid alterations and Sample Description | Normalised luminescence (%) | | | | | P value |
|---|---|---|---|---|---|---|---|
| | | Expt 1 Rep 1 | Expt 1 Rep 2 | Expt 2 Rep 1 | Expt 2 Rep 2 | Mean | |
| Buffer | Assay buffer | 3.15 | 2.62 | 2.59 | 2.66 | 2.77 | n/a |
| Buffer | Assay buffer | 2.68 | 2.46 | 2.95 | 3.00 | | |
| 2-1 | wild type reference | 123.42 | pd | 103.07 | 107.12 | 111.20 | 0.002 |
| 2-4 | L234A/L235S/G236R | 2.49 | 2.55 | 2.51 | 2.67 | 2.56 | ns |
| 2-7 | L234D/L235K/G236R | 2.49 | 2.21 | 2.60 | 2.63 | 2.48 | ns |
| 2-19 | L234G/L235S/G236R | 2.44 | pd | 2.56 | 2.77 | 2.59 | ns |
| 2-23 | L234K/L235R/G236R | 2.63 | 2.43 | 2.38 | 2.61 | 2.52 | ns |
| 2-24 | L234K/L235S/G236R | 2.61 | 2.23 | 2.28 | 3.37 | 2.62 | ns |
| 2-25 | L234K/L235T/G236R | 5.16 | 4.94 | 8.19 | 2.98 | 5.32 | 0.049 |
| 2-26 | L234K/L235V/G236R | 2.31 | 2.21 | 2.38 | 3.10 | 2.50 | ns |
| 2-27 | L234Q/L235A/G236R | 2.52 | 2.31 | 2.83 | 3.08 | 2.69 | ns |
| 2-30 | L234Q/G236R | 4.17 | 3.83 | 9.74 | 3.27 | 5.25 | ns |
| 2-33 | L234Q/L235S/G236R | 2.77 | 2.59 | 2.88 | 2.89 | 2.78 | ns |
| 2-34 | L234Q/L235T/G236R | 2.39 | 2.39 | 2.46 | 2.51 | 2.44 | ns |
| 2-35 | L234Q/L235V/G236R | 2.40 | 2.24 | 2.42 | 2.53 | 2.40 | ns |
| 2-36 | L234R/L235D/G236R | 40.33 | 37.38 | 40.43 | 40.04 | 39.54 | 0.000 |
| 2-37 | L234R/L235E/G236R | 2.47 | 2.15 | 2.50 | 2.33 | 2.36 | ns |
| 2-38 | L234R/L235H/G236R | 2.52 | 2.20 | 2.29 | 2.23 | 2.31 | ns |
| 2-39 | L234R/L235I/G236R | 2.36 | 2.07 | 2.05 | 2.27 | 2.19 | ns |
| 2-40 | L234R/L235K/G236R | 2.35 | 2.13 | 2.13 | 2.35 | 2.24 | ns |
| 2-43 | L234R/L235R/G236R | 2.15 | 1.96 | 2.11 | 2.27 | 2.12 | ns |
| 2-47 | L234S/L235G/G236R | 2.20 | 2.36 | 2.00 | 2.21 | 2.19 | ns |
| 2-48 | L234S/L235H/G236R | 2.68 | 2.70 | 2.20 | 2.29 | 2.47 | ns |
| 2-51 | L234S/L235R/G236R | 2.55 | 2.48 | 2.24 | 2.27 | 2.39 | ns |
| 2-52 | L234S/L235T/G236R | 2.75 | 2.72 | 2.31 | 2.22 | 2.50 | ns |
| 2-53 | L234S/L235V/G236R | 2.77 | 2.55 | 2.20 | 2.17 | 2.42 | ns |
| 2-58 | L234T/L235K/G236R | 2.75 | 2.52 | 2.12 | 2.07 | 2.36 | ns |
| 2-60 | L234T/L235Q/G236R | 2.69 | 2.29 | 2.26 | 2.14 | 2.34 | ns |
| 2-61 | L234T/L235R/G236R | 2.97 | 2.65 | 2.28 | 2.03 | 2.48 | ns |
| 2-63 | L234T/L235T/G236R | 2.63 | 1.91 | 2.34 | 2.20 | 2.27 | ns |
| 2-65 | L234A/L235A (LALA) | 11.11 | 7.24 | 8.43 | 8.04 | 8.70 | 0.003 |
| 2-66 | L234A/L235A/P329G (LALAPG reference) | 2.21 | 2.36 | 2.13 | 2.21 | 2.23 | ns |
| 2-67 | N297Q (aglycosyl) | 2.33 | 2.81 | 2.26 | 2.30 | 2.43 | ns |
| 2-75 | L234F/L235E/P331S | 3.91 | 4.65 | 4.00 | 4.30 | 4.22 | 0.000 |
| 2-76 | L234F/L235Q/K322Q | 4.80 | 6.18 | 4.66 | 5.12 | 5.19 | 0.002 | ns = not significant (p > 0.05).

TABLE 21

Normalised responses of samples of purified antibodies in an ADCP assay.

| Sample | Amino acid alterations and Sample Description | Expt 1 Rep 1 | Expt 1 Rep 2 | Mean | P value |
|---|---|---|---|---|---|
| Buffer | Assay buffer | 2.89 | 2.72 | 2.70 | n/a |
| Buffer | Assay buffer | 2.61 | 2.59 | | |
| 2-1 | wild type reference | 129.10 | 110.80 | 119.95 | 0.025 |
| 2-4 | L234A/L235S/G236R | 2.55 | 2.61 | 2.58 | ns |
| 2-7 | L234D/L235K/G236R | 2.59 | 2.57 | 2.58 | ns |
| 2-19 | L234G/L235S/G236R | 2.35 | 2.49 | 2.42 | ns |
| 2-23 | L234K/L235R/G236R | 2.40 | 2.49 | 2.45 | ns |
| 2-24 | L234K/L235S/G236R | 2.46 | 2.55 | 2.51 | ns |
| 2-25 | L234K/L235T/G236R | 5.05 | 5.21 | 5.13 | 0.000 |
| 2-26 | L234K/L235V/G236R | 2.20 | 2.47 | 2.34 | ns |
| 2-27 | L234Q/L235A/G236R | 2.76 | 2.64 | 2.70 | ns |
| 2-30 | L234Q/G236R | 4.99 | 4.36 | 4.67 | 0.044 |
| 2-33 | L234Q/L235S/G236R | 2.46 | 1.88 | 2.17 | ns |
| 2-34 | L234Q/L235T/G236R | 2.40 | 2.37 | 2.39 | ns |
| 2-35 | L234Q/L235V/G236R | 2.43 | 2.44 | 2.43 | ns |
| 2-36 | L234R/L235D/G236R | 42.50 | 43.75 | 43.12 | 0.004 |
| 2-37 | L234R/L235E/G236R | 2.11 | 2.50 | 2.30 | ns |
| 2-38 | L234R/L235H/G236R | 2.31 | 2.27 | 2.29 | ns |
| 2-39 | L234R/L235I/G236R | 1.99 | 2.62 | 2.31 | ns |
| 2-40 | L234R/L235K/G236R | 2.58 | 2.72 | 2.65 | ns |
| 2-43 | L234R/L235R/G236R | 2.43 | 2.92 | 2.68 | ns |
| 2-47 | L234S/L235G/G236R | 2.35 | 2.29 | 2.32 | ns |
| 2-48 | L234S/L235H/G236R | 2.75 | 2.91 | 2.83 | ns |
| 2-51 | L234S/L235R/G236R | 2.63 | 2.77 | 2.70 | ns |
| 2-52 | L234S/L235T/G236R | 2.76 | 2.41 | 2.59 | ns |
| 2-53 | L234S/L235V/G236R | 3.07 | 3.71 | 3.39 | ns |
| 2-58 | L234T/L235K/G236R | 3.11 | 2.93 | 3.02 | 0.049 |
| 2-60 | L234T/L235Q/G236R | 2.80 | 2.89 | 2.84 | ns |
| 2-61 | L234T/L235R/G236R | 2.92 | 3.00 | 2.96 | 0.017 |
| 2-63 | L234T/L235T/G236R | 2.50 | 2.78 | 2.64 | ns |
| 2-65 | L234A/L235A (LALA) | 32.42 | 31.02 | 31.72 | 0.007 |
| 2-66 | L234A/L235A/P329G (LALAPG reference) | 2.86 | 2.60 | 2.73 | ns |
| 2-67 | N297Q (aglycosyl) | 2.75 | 2.52 | 2.63 | ns |
| 2-75 | L234F/L235E/P331S | 46.34 | 48.97 | 47.66 | 0.009 |
| 2-76 | L234F/L235Q/K322Q | 52.55 | 50.17 | 51.36 | 0.008 | ns = not significant (p > 0.05).

Example 7 Size Exclusion Chromatography

Purified antibodies were analysed by size-exclusion chromatography (SEC). SEC was performed on an Aglient 1100 series HPLC using a Superdex 200 Increase 5/150 GL column equilibrated in PBS, PH 7.2 at a flow rate of 0.2 mL/min. Absorbance was measured at 280 nm and the area of the peak corresponding to IgG monomer was measured as a percentage of the total eluted protein. Samples were analysed shortly after preparation and again 7 days and 14 days after incubation at 40° C. The results are shown in Table 22. On average, there was a decrease of about 1.7% in the fraction of monomer after 7 days at 40° ° C. and a decrease of about 4.4% after 14 days and this was closely mirrored by the wild-type reference sample.

TABLE 22

Size exclusion chromatography of purified antibodies before and after incubation at 40° C.

| | | Fraction of IgG monomer (%) | | |
|---|---|---|---|---|
| Sample | Amino acid alterations and Sample Description | Original | 7 days at 40° C. | 14 days at 40° C. |
| 2-1 | wild-type reference | 97.7 | 96.5 | 93.9 |
| 2-2 | L234A/L235A/G236R | 97.6 | 95.5 | 91.6 |
| 2-3 | L234A/G236R | 97.7 | 94.7 | 91.7 |
| 2-4 | L234A/L235S/G236R | 98.0 | 93.9 | 91.8 |
| 2-5 | L234A/L235T/G236R | 97.7 | 95.4 | 92.7 |
| 2-6 | L234D/L235H/G236R | 97.6 | 95.8 | 92.5 |
| 2-7 | L234D/L235K/G236R | 97.4 | 94.8 | 92.7 |
| 2-8 | L234D/G236R | 97.8 | 96.6 | 93.4 |
| 2-9 | L234D/L235Q/G236R | 97.8 | 95.4 | 91.3 |
| 2-10 | L234D/L235S/G236R | 97.1 | 94.6 | 91.4 |
| 2-11 | L234D/L235T/G236R | 97.6 | 96.9 | 93.1 |
| 2-12 | L234E/L235D/G236R | 97.8 | 96.1 | 92.5 |
| 2-13 | L234E/L235H/G236R | 97.7 | 97.0 | 92.2 |
| 2-14 | L234E/L235I/G236R | 97.8 | 97.4 | 93.1 |
| 2-15 | L234E/G236R | 97.9 | 96.6 | 94.3 |
| 2-16 | L234E/L235V/G236R | 97.9 | 96.7 | 94.1 |
| 2-17 | L234G/L235H/G236R | 98.1 | 96.8 | 93.6 |
| 2-18 | L234G/L235Q/G236R | 97.8 | 96.7 | 93.5 |
| 2-19 | L234G/L235S/G236R | 98.1 | 97.5 | 93.9 |
| 2-20 | L234H/L235I/G236R | 97.5 | 96.8 | 92.2 |
| 2-21 | L234H/L235S/G236R | 98.2 | 73.5 (pd) | 93.3 |
| 2-22 | L234K/L235Q/G236R | 98.1 | 96.6 | 93.3 |
| 2-23 | L234K/L235R/G236R | 98.2 | 96.7 | 92.8 |
| 2-24 | L234K/L235S/G236R | 98.4 | 96.6 | 93.6 |
| 2-25 | L234K/L235T/G236R | 97.6 | 96.0 | 93.8 |
| 2-26 | L234K/L235V/G236R | 98.1 | 97.6 | 91.7 |
| 2-27 | L234Q/L235A/G236R | 98.1 | 97.7 | 91.5 |
| 2-28 | L234Q/L235D/G236R | 95.7 | 96.5 | 93.1 |
| 2-29 | L234Q/L235H/G236R | 98.0 | 97.3 | 91.1 |
| 2-30 | L234Q/G236R | 98.0 | 97.7 | 93.1 |

TABLE 22-continued

Size exclusion chromatography of purified antibodies
before and after incubation at 40° C.

| | | Fraction of IgG monomer (%) | | |
|---|---|---|---|---|
| Sample | Amino acid alterations and Sample Description | Original | 7 days at 40° C. | 14 days at 40° C. |
| 2-31 | L234Q/L235Q/G236R | 95.8 | 96.9 | 92.4 |
| 2-32 | L234Q/L235R/G236R | 98.3 | 96.9 | 94.2 |
| 2-33 | L234Q/L235S/G236R | 97.8 | 95.7 | 91.2 |
| 2-34 | L234Q/L235T/G236R | 97.9 | 97.1 | 93.4 |
| 2-35 | L234Q/L235V/G236R | 97.3 | 96.1 | 94.6 |
| 2-36 | L234R/L235D/G236R | 97.4 | 97.2 | 92.1 |
| 2-37 | L234R/L235E/G236R | 98.2 | 96.1 | 91.8 |
| 2-38 | L234R/L235H/G236R | 98.1 | 94.8 | 93.1 |
| 2-39 | L234R/L235I/G236R | 98.4 | 96.7 | 90.4 |
| 2-40 | L234R/L235K/G236R | 98.6 | 95.9 | not done |
| 2-41 | L234R/G236R | 98.2 | 96.1 | 93.7 |
| 2-42 | L234R/L235Q/G236R | 98.4 | 96.1 | 94.3 |
| 2-43 | L234R/L235R/G236R | 98.4 | 96.6 | 94.1 |
| 2-44 | L234R/L235T/G236R | 98.4 | 95.6 | 93.0 |
| 2-45 | L234S/L235D/G236R | 98.0 | 96.7 | 95.1 |
| 2-46 | L234S/L235E/G236R | 98.0 | 95.9 | 93.1 |
| 2-47 | L234S/L235G/G236R | 97.7 | 95.9 | 93.1 |
| 2-48 | L234S/L235H/G236R | 98.2 | 96.7 | 93.4 |
| 2-49 | L234S/L235I/G236R | 98.0 | 96.9 | 92.1 |
| 2-50 | L234S/G236R | 98.0 | 96.4 | 94.4 |
| 2-51 | L234S/L235R/G236R | 97.8 | 96.8 | 94.3 |
| 2-52 | L234S/L235T/G236R | 97.8 | 96.5 | 95.1 |
| 2-53 | L234S/L235V/G236R | 98.1 | 96.3 | 94.2 |
| 2-54 | L234T/L235A/G236R | 98.1 | 97.1 | 94.3 |
| 2-55 | L234T/L235D/G236R | 97.7 | 97.4 | 95.0 |
| 2-56 | L234T/L235H/G236R | 98.2 | 94.7 | 94.2 |
| 2-57 | L234T/L235I/G236R | 97.9 | 96.3 | 92.6 |
| 2-58 | L234T/L235K/G236R | 98.1 | 96.8 | 93.0 |
| 2-59 | L234T/G236R | 97.6 | 94.3 | 92.4 |
| 2-60 | L234T/L235Q/G236R | 98.2 | 94.6 | 94.1 |
| 2-61 | L234T/L235R/G236R | 97.9 | 95.4 | 94.7 |
| 2-62 | L234T/L235S/G236R | 97.8 | 95.7 | 93.2 |
| 2-63 | L234T/L235T/G236R | 97.7 | 95.1 | 95.1 |
| 2-64 | L234T/L235V/G236R | 97.7 | 94.9 | 94.6 |
| 2-65 | L234A/L235A (LALA) | 97.8 | 96.5 | 95.1 |
| 2-66 | L234A/L235A/P329G (LALAPG reference) | 97.7 | 96.2 | 94.2 |
| 2-67 | N297Q (aglycosyl) | 97.9 | 95.2 | 94.0 |
| 2-68 | G236R/L328R | 98.1 | 95.8 | 95.4 |
| 2-69 | L234A/G237A | 97.5 | 96.9 | 94.4 |
| 2-70 | L234A/L235A/G237A | 97.9 | 97.7 | 95.9 |
| 2-71 | L234A/L235E | 98.0 | 95.8 | 94.4 |
| 2-72 | L235V/F243L/R292P/Y300L/P396L | 97.5 | 96.1 | 93.5 |
| 2-73 | D265A/P329A | 97.3 | 95.4 | 94.8 |
| 2-74 | L234A/L235A/K322A | 97.2 | 95.8 | 93.9 |
| 2-75 | L234F/L235E/P331S | 98.0 | 95.9 | 94.9 |
| 2-76 | L234F/L235Q/K322Q | 97.7 | 96.5 | 94.1 |
| 2-77 | L234A/L235A/G237A/P238S/H268A/A330S/P331S | 97.2 | 94.4 | 94.3 |
| 2-78 | E233P/L234V/L235A/G236Δ/A327G/A330S/P331S | 97.1 | 93.7 | 94.3 |
| 2-79 | L235A/G236R | 97.5 | 93.8 | 94.2 |
| 2-80 | L235S/G236R | 97.9 | 94.2 | 98.8 |
| 2-81 | G236R | 97.5 | 95.5 | 89.2 |
| 2-82 | L234Q/L235S | 97.3 | 95.4 | 93.5 |
| 2-83 | L235G/G236R | 97.6 | 95.2 | 93.2 |
| | Mean of all samples | 97.8 | 96.1 | 93.4 |
| | Standard deviation of all samples | 0.5 | 1.0 | 1.4 | pd = anomalous result, point dropped from calculation of mean and standard deviation.

Example 8 Differential Scanning Fluorimetry

Antibodies were assessed using differential scanning fluorimetry (DSF) to provide an indication of their relative thermal stability using the Protein Thermal Shift Dye Kit (ThermoFisher Cat. No. 4461146) in accordance with the manufacturer's instructions. 5 μL of Protein Thermal Shift Dye Buffer was added to a polypropylene microplate (ThermoFisher Cat. No. N8010560). 10 μL of test sample (1 mg/mL in PBS) was added and mixed. Protein Thermal Shift Dye (1000×) was diluted with water to give an 8× intermediate stock and 2.5 μL was added to each sample and mixed. Melt curves were measured using a real-time PCR system (ThemoFisher QuantStudio 3) using the Orange filter set with excitation at 580±10 nm and emission at 623±14 nm. The temperature was continuously ramped from 25° C. to 90° C. at a rate of 0.05° C. per sec. Measurements were made at approximately 0.1° ° C. intervals. As expected, the fluorescence responses did not show a single clearly defined melting temperature (Tm), because the IgG molecule contains several different domains which are expected to melt at different temperatures. To obtain a measure of comparative temperature stability of different variants, the temperature was determined at which the fluorescence was consistently (for three consecutive measurements) 2000 units above the mean baseline fluorescence measured between 25° C. and 35° C. This temperature was taken to be the start of the melting (denaturation) process. Each sample was measured in duplicate and the mean results are shown in Table 23. With the exception of sample 2-67 (aglycosyl), all of the variants started to melt at a temperature within the range 61.2° ° C. to 67.6° C., which is no more than 2.6° C. lower to 3.8° C. higher than the wild type reference sample 2-1.

TABLE 23

Initial melt temperatures of purified antibodies measured by differential scanning fluorimetry.

| Sample | Amino acid alterations and Sample Description | Mean Temperature at start of melt (° C.) |
|---|---|---|
| 2-1 | wild type reference | 63.8 |
| 2-4 | L234A/L235S/G236R | 61.2 |
| 2-7 | L234D/L235K/G236R | 66.0 |
| 2-19 | L234G/L235S/G236R | 67.6 |
| 2-23 | L234K/L235R/G236R | 63.4 |
| 2-24 | L234K/L235S/G236R | 61.5 |
| 2-25 | L234K/L235T/G236R | 64.8 |
| 2-26 | L234K/L235V/G236R | 63.7 |
| 2-27 | L234Q/L235A/G236R | 63.7 |
| 2-30 | L234Q/G236R | 62.5 |
| 2-33 | L234Q/L235S/G236R | 62.5 |
| 2-34 | L234Q/L235T/G236R | 61.9 |
| 2-35 | L234Q/L235V/G236R | 62.3 |
| 2-36 | L234R/L235D/G236R | 62.9 |
| 2-37 | L234R/L235E/G236R | 63.1 |
| 2-38 | L234R/L235H/G236R | 63.8 |
| 2-39 | L234R/L235I/G236R | 63.0 |
| 2-40 | L234R/L235K/G236R | 63.3 |
| 2-43 | L234R/L235R/G236R | 64.2 |
| 2-47 | L234S/L235G/G236R | 61.8 |
| 2-48 | L234S/L235H/G236R | 62.9 |
| 2-51 | L234S/L235R/G236R | 63.0 |
| 2-52 | L234S/L235T/G236R | 62.9 |
| 2-53 | L234S/L235V/G236R | 65.1 |
| 2-58 | L234T/L235K/G236R | 64.0 |
| 2-60 | L234T/L235Q/G236R | 63.3 |
| 2-61 | L234T/L235R/G236R | 64.1 |
| 2-62 | L234T/L235S/G236R | 63.3 |
| 2-63 | L234T/L235T/G236R | 63.0 |
| 2-65 | L234A/L235A (LALA) | 62.7 |
| 2-66 | L234A/L235A/P329G (LALAPG reference) | 62.4 |
| 2-67 | N297Q (aglycosyl) | 51.8 |
| 2-75 | L234F/L235E/P331S | 65.4 |
| 2-76 | L234F/L235Q/K322Q | 65.2 |

Example 9 Cytokine Release

Antibodies were assessed for their ability to cause release of cytokines from human peripheral blood mononuclear cells (PBMC). PBMC were isolated from five healthy donors by centrifugation over Ficoll-Paque PLUS (GE Healthcare Cat. No. 11778538) and washed with RPMI medium (Sigma Cat. No. 8758) containing 1% heat-inactivated foetal bovine serum (FBS) (Fisher Scientific Cat. No. 11550526) and 1% Penicillin/Streptomycin (PS) (Sigma Cat. No. 4333). The PBMC were resuspended at $2 \times 10^6$ per mL in RPMI containing 10% FBS and 1% PS (cRPMI). Anti-CD3 antibodies at 1 mg/mL in PBS were diluted with cRPMI to give concentrations of 200, 20, 2, 0.2 or 0.02 μg/mL. A negative control consisted of PBS diluted five-fold with cRPMI. Each sample was tested in triplicate. 100 μL of test sample was mixed with 100 μL of cell suspension in a 96-well round-bottom microplate and cultured at 37° C. and 5% $CO_2$ for 24 h. The plate was centrifuged at 400×g for 5 min and the culture supernatants were collected. Cytokines (GM-CSF, IFNγ, IL-2, IL-4, IL-6, IL-8, IL-10 and TNFα) were quantified in the cell culture supernatant by Luminex assay (Bio-Rad Cat. No. M50000007A) on a Bio-Plex® 200 system with Bio-Plex Manager software according to manufacturer's instructions. For each cytokine, the mean concentration obtained from all five donors was compared with the mean concentration obtained with the negative control using a one-tailed t-test, assuming unequal variances. Results were flagged if they were significantly higher (p≤0.05) than the response for the negative control. Positive responses were obtained for the wild-type reference antibody at final concentrations of 10, 1,0.1 and 0.01 μg/mL.

The results of cytokine release from five donors stimulated at a final concentration of 10 μg/mL are shown in FIGS. 5A to 5D. Variants L234S/L235T/G236R, L234S/L235V/G236R and L234A/L235A/P329G (LALAPG) gave no significant increase above the negative control for any of the cytokines. Similar results were obtained from five independent donors stimulated at 0.1 μg/mL.

Example 10 Pharmacokinetics

Tg276 transgenic mice express the human FCGRT gene under the control of a strong CAG promoter (Proetzel 2014). Mice were back-crossed onto a congenic FcRn-null strain so that the strain expresses high levels of human FcRn and no mouse FcRn. These mice are suitable for detecting subtle differences in antibody persistence in vivo.

A pharmacokinetic (PK) study was carried out by The Jackson Laboratory (Bar Harbor, ME, USA) in accordance with their standard procedures. Twenty-four 10 week old male B6.Cg-Fcgrttm1Dcr Tg(CAG-FCGRT)276Dcr/DcrJ (Tg276, JAX stock #004919) homozygous mice were distributed into 4 groups with 6 mice per group. On Day 0, test articles at 5 mg/kg were IV administered to all mice. Blood samples were collected into EDTA at 15 min, 3 h, 1 day, 3 days, 5 days, 7 days, 10 days, and 14 days, processed to plasma and stored frozen until analysis. Plasma samples were diluted 1/500 and assessed by a human IgG Fc specific ELISA using each test article as a standard. The dose-response curve was fitted by a five-parameter logistic equation and the concentration of test samples was determined by interpolation. Each test sample was measured in triplicate and the mean concentrations were used for calculation of kinetic parameters. The data were fitted to a biphasic model by noncompartmental analysis and an elimination phase half-life was calculated from between 24 h and 15 days. The results are shown in Table 24. Difference in half-life between the samples were analysed by Tukey's multiple comparisons test. There was a statistically significant difference between each of the variants and the wild-type, but no statistically significant differences between the variants. All of the pharmacokinetic parameters (half-life, clearance, Cmax, area under the curve, volume of distribution) for each of the variants was within ±50% of the corresponding parameter for the wild-type antibody.

TABLE 24

Calculated pharmacokinetic parameters.

| ID | Amino acid alterations and Sample Description | Half-Life days | Clearance mL/h/kg | Cmax µg/mL | Area under Curve µg · h/mL | Volume of Distribution mL/kg |
|---|---|---|---|---|---|---|
| 2-01 | wild-type reference | 3.51 ± 0.15 | 0.96 ± 0.05 | 130 ± 6 | 4959 ± 226 | 116 ± 6 |
| 2-52 | L234S/L235T/G236R | 2.07 ± 0.12 | 1.36 ± 0.04 | 120 ± 4 | 3596 ± 113 | 97 ± 6 |
| 2-65 | L234A/L235A (LALA) | 1.76 ± 0.11 | 1.54 ± 0.06 | 117 ± 5 | 3249 ± 124 | 93 ± 4 |
| 2-67 | N297Q (aglycosyl) | 2.28 ± 0.14 | 1.56 ± 0.02 | 119 ± 9 | 3161 ± 29 | 117 ± 6 |

Example 11 Glycosylation

N-linked carbohydrates were analysed following separation by hydrophilic interaction liquid chromatography (HILIC). N-glycans were released with rapid PNGase F (NEB Cat. No. P07010) essentially according to the manufacturer's instructions. The released glycans were fluorescently labelled by reductive amination with 2-aminobenzoic acid and sodium cyanoborohydride. The labelled oligosaccharides were purified by HILIC using DPA-6S solid phase extraction cartridges (Sigma Cat. No. 52624-U) as described (Neville 2004). The purified labelled oligosaccharides were diluted with acetonitrile (66% acetonitrile final concentration), and analysed using an Agilent 1260 Quaternary HPLC system with fluorescence detection (excitation at 240 nm, emission at 430 nm) using a BEH Amide Column, 3.5 µm, 2.1 mm×150 mm (Waters Cat. No. 186004861) at 30° C. The column was eluted with a gradient of 85:10:5 to 50:15:35 acetonitrile:0.525M ammonium acetate pH 3.75: water at 0.15 mL/min. Representative chromatograms for each sample are shown in FIG. 6A. The same spectrum of glycoforms was seen for each of the samples. The experiment was repeated using a selection of CD20 antibodies prepared from both HEK and CHO cells. Representative chromatograms are shown in FIG. 6B. The spectrum of glycoforms was slightly different between antibody prepared in the different cell types, but within each cell type, the spectrum was the same.

Example 12 Thermal Stability

Antibodies were assessed using the Uncle® Biostability Platform (Unchained Labs, Pleasanton CA, USA) in accordance with the manufacturer's instructions. Samples were subjected to a thermal ramping experiment starting at 25° C. and increasing to 95° C. at a rate of 0.3°C per minute. Intrinsic protein fluorescence and static light scattering (266 nm) were measured throughout the experiment as indicators of protein unfolding and aggregation respectively. Each sample was tested at a concentration of 1 mg/mL in phosphate buffered saline (PBS) and a sample volume of 9 µL. 48 individual samples were tested simultaneously and the whole experiment was carried out three times to obtain triplicate independent temperature profiles for each test sample. The 'melting temperature' Tm was defined as the major inflection point on the fluorescence versus temperature plot, i.e. the temperature as which the rate of change of fluorescence reached a maximum. The 'aggregation temperature' Tagg was defined as the temperature at which the light scattering started to increase. Variants were compared with the wild-type reference by a two-tailed t-test. The results are shown in Table 25.

The aglycosyl variants of CD20 and CD3 antibodies had significantly lower Tm, all other variants had a Tm higher than or not significantly different from the wild type. The aglycosyl variants of CD20 and CD3 antibodies and the L234Q/L235S/G236R CD20 variant had significantly lower Tagg, all other variants had a Tagg higher than or not significantly different from the wild type.

TABLE 25

Melt temperatures (Tm) and onset of aggregation (Tagg) of purified antibodies measured by intrinsic differential scanning fluorescence and static light scattering.

| Amino acid alterations and Sample Description | Target Antigen | | | Target Antigen | | |
|---|---|---|---|---|---|---|
| | CD20 | CD3 | CD52 | CD20 | CD3 | CD52 |
| | Mean Tm (° C.) | | | Mean Tagg (° C.) | | |
| wild type reference | 68.05 | 69.14 | 71.80 | 70.19 | 64.73 | 70.96 |
| L234G/L235S/G236R | 68.24 | 70.53 | 73.50 | 69.93 | 64.67 | 70.56 |
| L234Q/L235S/G236R | 69.39 | not done | not done | 58.48 | not done | not done |
| L234S/L235T/G236R | 68.23 | 72.07 | 73.53 | 69.79 | 72.31 | 70.18 |
| L234S/L235V/G236R | 68.01 | 69.86 | 73.88 | 68.41 | 64.20 | 69.96 |
| L234T/L235Q/G236R | 67.85 | 70.40 | 73.25 | 69.03 | 66.11 | 69.91 |
| L234T/L235T/G236R | 68.28 | not done | not done | 70.07 | not done | not done |
| L234A/L235A (LALA) | 68.85 | 69.45 | 73.31 | 69.84 | 67.45 | 71.75 |
| L234A/L235A/P329G (LALAPG) | 67.27 | not done | not done | 69.60 | not done | not done |
| N297Q (aglycosyl) | 59.14 | 60.00 | 73.23 | 68.25 | 62.42 | 70.87 |

Example 13 In Vitro Assessment of Unwanted Immunogenicity

The ProMap® Immunogenicity System is based on the flow cytometric method of analysing cell proliferation by tracking cells that have been labelled with carboxyfluorescein succinimidyl ester (CFSE). Protein or peptide antigens presented by antigen-presenting cells to CD4+ T cells result in cell proliferation which can be measured by a decrease in fluorescence intensity of CFSE-labelled cells. A study was carried out by Proimmune (Oxford, UK) according to their standard Promap® T-cell Proliferation Assay procedure. Test samples consisted of purified 20-mer peptides (Kendall Scientific Inc, Lincolnshire, IL, USA). The sequences of the peptides are shown in Table 26.

TABLE 26

Listing of 20-mer peptides used in immunogenicity study

| ID | Amino acid alterations and Sample Description | Sequence |
| --- | --- | --- |
| 01 | L234A/L235A/G237A | PAPEAAGAPSVFLFPPKPKD |
| 02 | L234A/L235A (LALA) | PAPEAAGGPSVFLFPPKPKD |
| 03 | L234A/L235E | PAPEAEGGPSVFLFPPKPKD |
| 04 | L234A/G237A | PAPEALGAPSVFLFPPKPKD |
| 05 | L234F/L235E | PAPEFEGGPSVFLFPPKPKD |
| 06 | L234F/L235Q | PAPEFQGGPSVFLFPPKPKD |
| 07 | L234G/L235S/G236R | PAPEGSRGPSVFLFPPKPKD |
| 08 | wild-type reference | PAPELLGGPSVFLFPPKPKD |
| 09 | G236R | PAPELLRGPSVFLFPPKPKD |
| 10 | L234S/L235T/G236R | PAPESTRGPSVFLFPPKPKD |
| 11 | L234S/L235V/G236R | PAPESVRGPSVFLFPPKPKD |
| 12 | L234T/L235Q/G236R | PAPETQRGPSVFLFPPKPKD |
| 13 | wild-type reference | PAPELLGGPSVFLFPPKPKD |
| 14 | L234S/L235T/G236R | PAPESTRGPSVFLFPPKPKD |

Positive control samples performed as expected. Surprisingly, peptide 09 (G236R) gave positive responses with 4/20 donors. Peptide 11 (L234S/L235V/G236R) gave positive responses with 2/20 donors and other peptides gave positive responses with no donors or only one donor. At least two donors should give a positive response for a peptide to be considered a potential T cell epitope.

REFERENCES

| | |
| --- | --- |
| Angal 1993 | Mol. Immunol. 30: 105-108. |
| Armour 1999 | Eur. J. Immunol. 29: 2613-2624. |
| Bajaj 2012 | J. Appl. Pharm. Sci. 2: 129-138 |
| Beck 2011 | mAbs 3: 415-416. |
| Boesch 2014 | mAbs 6: 915-927. |
| Bolt 1993 | Eur. J. Immunol. 23: 403-411. |
| Borrok 2017 | J. Pharm. Sci. 106: 1008-1017. |
| Brinkmann 2017 | MAbs 9: 182-212. |
| Brinks 2013 | Pharm. Res. 30: 1719-1728. |
| Bruhns 2009 | Blood 113: 3716-3725. |
| Bryson 2010 | Biodrugs 24: 1-8. |
| Chen 2007 | Retrovirology 4: 33. |
| Choi 2013 | Mol. Cancer Ther. 12: 2748-2759. |
| Choi 2015a | Mol. Immunol. 65: 377-383. |
| Choi 2115b | PLoS One 10: e0145349. |
| Costa 2014 | Crit. Rev. Biotechnol. 34: 281-299. |
| Dall'Acqua 2006 | J. Immunol. 177: 1129-1138. |
| Datta-Mannan 2011 | Drug. Metab.. Dispos 42: 1867-1872. |
| de Jong 2016 | PLoS Biol 14: e1002344. |
| Deng 2010 | Drug Metab. Dispos. 38: 600-605. |
| Dhanda 2019 | Nucleic Acids Research 47: W502-W506. |
| Edelman 1969 | Proc. Natl. Acad. Sci. USA 63: 78-85. |
| Engelsman 2011 | Pharm. Res. 28: 920-933. |
| Fan 2014 | Mol. Cancer Therapeutics 2014: 0715. |
| Finco 2014 | Cytokine 66: 143-155. |
| Findlay 2010 | J. Immunol. Meth. 352: 1-12. |
| Findlay 2011 | Cytokine 55: 141-151. |
| Fleri 2017 | Frontiers in Immunology 8: 278. |
| Greenbaum 2011 | Immunogenetics. 63: 325-35, 2011. |
| Gregorio 2019 | Methods Protocols 2: 24. |
| Grimaldi 2016 | Cytokine 85: 101-108. |
| Gunasekaran 2010 | J. Biol. Chem. 285: 19637-19646. |
| Hale 1983 | Blood 62: 873-882. |
| Hezarah 2001 | J. Virol. 75: 12161-12168 |
| Hinton 2004 | J. Bio. Chem. 279: 6213-6216. |
| Horton 2011 | J. Immunol. 186: 4223-4233. |
| Hsiao 2018 | Breast Cancer Research 20: 43. |
| Kabat 1991 | Sequences of Proteins of Immunological Interest, 5th Ed. Public Health Service, National Institutes of Health, Bethesda, MD. |
| Kim 1999 | Eur. J. Immunol. 29: 2819-2825. |
| Idusogie 2000 | J. Immunol. 164: 4178-4184. |
| Ishino 2013 | J. Biol. Chem. 288: 16529-16537. |
| Jafari 2017 | Curr. Med. Chem. 24: 1228-1237. |
| Jawa 2013 | Clinical Immunology 149: 534-555. |
| Jefferis 2005 | Biotechnol. Prog. 21: 11-16. |

-continued

| | |
|---|---|
| Jensen 2018 | Immunology 154: 394-406. |
| Joubert 2016 | PLoS ONE 11(8): e0159328. |
| Kanda 2006 | Glycobiology 17: 104-118. |
| King 2014 | Proc. Natl. Acad Sci. 111: 8577-8582. |
| Kuo 2011 | mAbs 3: 422-430. |
| Labrijn 2013 | Proc. Natl. Acad. Sci.110: 5145-5150. |
| Lazar 2006 | Proc. Natl. Acad. Sci.103: 4005-4010 |
| Leaver-Fay 2016 | Structure 24: 641-651. |
| Lee 2019 | Nature Communications 10: 5031. |
| Lin 2013 | Cancer Biology & Therapy 14: 1032-1038 |
| Liu 2018 | Protein Cell 9: 15-32. |
| Loureiro 2011 | J. Virology 85: 3010-3014. |
| Lund 1996 | J Immunol. 157: 4963-4969. |
| Mekhaiel 2011 | Sci. Rep. 1: 124. |
| Merchant 1998 | Nat. Biotechnol. 16: 677-681. |
| Michaelsen 2009 | Scand. J. Immunol. 70: 553-564. |
| Moore 2010 | mAbs 2: 181-189. |
| Moore 2011 | mAbs 3: 546-557. |
| Moore 2019 | Methods 154: 38-50. |
| Nardis 2017 | J. Biol. Chem. 292: 14706-14717. |
| Neville 2004 | Anal. Biochem. 331: 275-282. |
| Nielson 2007 | BMC Bioinformatics 8: 238. |
| Niesen 2007 | Nature Protocols 2: 2212-2221. |
| Niles 2007 | Anal. Biochem. 366: 197-206. |
| Oganesyan 2008 | Acta Cryst. D64: 700-704. |
| Paul 2015 | J. Immunol. Meth. 422: 28-34. |
| Petkova 2006 | Int. Immunol. 18: 1759-1769. |
| Proetzel 2014 | Methods 65: 148-153. |
| Remington 1995 | The Science and Practice of Pharmacy, 19th Edition, Gennaro, Ed., Mack Publishing Co. |
| Reutsch 2015a | mAbs, 7: 167-179. |
| Reutsch 2015b | mAbs, 7: 732-742. |
| Ridgway 1996 | Protein Eng. Design 9: 617-621. |
| Romer 2011 | Blood 118: 6772-6782. |
| Rose 2011 | Structure 19: 1274-1282. |
| Rowland 1995 | Clinical Pharmacokinetics: Concepts and Applications, Third Edition, pub Lippincott, Williams & Wilkins. |
| Schlothauer 2016 | Protein Engineering, Design & Selection 29: 457-466. |
| Senisterra 2009 | Mol. BioSyst. 5: 217-223. |
| Shan 2016 | PLoS One 11: e0180345. |
| Shields 2011 | J . Biol. Chem. 276: 6591-6604 |
| Shire 2009 | Current Opin. Biotechnol. 20: 708-714. |
| Sidney 2008 | Immunonome Research 4: 2. |
| Simeon 2018 | Protein Cell 9: 3-14. |
| Stapleton 2018 | Mol. Immunol. 95: 1-9. |
| Strop 2012 | J. Mol. Biol. 420: 204-219. |
| Sturniolo 1999 | Nat. Biotechnology 17: 555-561. |
| Tam 2017 | Antibodies 6: 1-34. |
| Vaccaro 2005 | Nat. Biotechnol. 23: 1283-1288. |
| Vafa 2014 | Methods 65: 114-126. |
| Vessilier 2015 | J. Immunol. Meth. 424: 43-52. |
| Von Kreudenstein 2013 | mAbs 5: 646-654. |
| Wang 2008 | PLoS Comput Biol. 4: e1000048. |
| Werner 2007 | Acta Paediatrica 96: 17-22. |
| Wilkinson 2013 | mAbs 5: 406-417. |
| Wing 1995 | Therapeutic Immunology 2: 183-190. |
| Wolf 2012 | Cytokine 60: 828-837. |
| Wozniak-Knopp 2017 | Protein Eng. Design 30: 657-671. |
| Xu 2000 | Cell. Immunol. 200: 16-26. |
| Yang 2018 | Frontiers in Immunology 8: 1860. |
| Yeung 2009 | J Immunol 2009; 182: 7663-7671. |
| Ying 2012 | J. Biol. Chem. 287: 19399-19408. |
| Ying 2014 | mAbs 6: 1201-1210. |
| Zalevsky 2010 | Nat. Biotechnol 28: 157-159. |
| Zhou 2017 | Biomedicines 5: 64. |

The invention claimed is:

1. A protein comprising a variant IgG Fc region or a variant Cγ2 domain, wherein the variant IgG Fc region or variant Cγ2 domain comprises a combination of amino acids selected from the group consisting of: 234G/235S/236R, 234S/235T/236R, 234S/235V/236R, 234T/235Q/236R, and 234T/235T/236R, wherein the amino acid numbering is according to the EU index as in Kabat, and wherein the binding of the protein to human FcγRI, when measured by surface plasmon resonance, is less than 50% of the binding of a reference protein comprising an Fc region comprising the amino acid sequence of SEQ ID NO: 2.

2. A conjugate comprising the protein of claim 1 which is covalently attached to another substance.

3. A composition comprising the protein of claim 1.

4. The protein of claim 1, wherein reduced effector function of the protein: (a) reduces the likelihood of adverse clinical effects; (b) increases the likelihood of beneficial clinical effects; or (c) facilitates the use of higher doses, more frequent doses or more doses when compared with a reference protein.

5. A test system or kit comprising the protein of claim 1.

6. The protein of claim 1, wherein the protein is an antibody.

7. The protein of claim 1, wherein the variant Fc region or variant Cγ2 domain is or is derived from human IgG1, human IgG2, human IgG3 or human IgG4.

8. The protein of claim 6, wherein the variant Fc region or variant Cγ2 domain is or is derived from human IgG1, human IgG2, human IgG3 or human IgG4.

9. The protein of claim 1, wherein the variant IgG Fc region or variant Cγ2 domain comprises a combination of amino acids comprising 234G/235S/236R, wherein the amino acid numbering is according to the EU index as in Kabat.

10. The protein of claim 9, wherein the protein is an antibody.

11. The protein of claim 9, wherein the variant Fc region or variant Cγ2 domain is or is derived from human IgG1, human IgG2, human IgG3 or human IgG4.

12. The protein of claim 10, wherein the variant Fc region or variant Cγ2 domain is or is derived from human IgG1, human IgG2, human IgG3 or human IgG4.

13. The protein of claim 1, wherein the variant IgG Fc region or variant Cγ2 domain comprises a combination of amino acids comprising 234S/235T/236R, wherein the amino acid numbering is according to the EU index as in Kabat.

14. The protein of claim 13, wherein the protein is an antibody.

15. The protein of claim 13, wherein the variant Fc region or variant Cγ2 domain is or is derived from human IgG1, human IgG2, human IgG3 or human IgG4.

16. The protein of claim 14, wherein the variant Fc region or variant Cγ2 domain is or is derived from human IgG1, human IgG2, human IgG3 or human IgG4.

17. The protein of claim 1, wherein the variant IgG Fc region or variant Cγ2 domain comprises a combination of amino acids comprising 234S/235V/236R, wherein the amino acid numbering is according to the EU index as in Kabat.

18. The protein of claim 17, wherein the protein is an antibody.

19. The protein of claim 17, wherein the variant Fc region or variant Cγ2 domain is or is derived from human IgG1, human IgG2, human IgG3 or human IgG4.

20. The protein of claim 18, wherein the variant Fc region or variant Cγ2 domain is or is derived from human IgG1, human IgG2, human IgG3 or human IgG4.

21. The protein of claim 1, wherein the variant IgG Fc region or variant Cγ2 domain comprises a combination of amino acids comprising 234T/235Q/236R, wherein the amino acid numbering is according to the EU index as in Kabat.

22. The protein of claim 21, wherein the protein is an antibody.

23. The protein of claim 21, wherein the variant Fc region or variant Cγ2 domain is or is derived from human IgG1, human IgG2, human IgG3 or human IgG4.

24. The protein of claim 22, wherein the variant Fc region or variant Cγ2 domain is or is derived from human IgG1, human IgG2, human IgG3 or human IgG4.

25. The protein of claim 1, wherein the variant IgG Fc region or variant Cγ2 domain comprises a combination of amino acids comprising 234T/235T/236R, wherein the amino acid numbering is according to the EU index as in Kabat.

26. The protein of claim 25, wherein the protein is an antibody.

27. The protein of claim 25, wherein the variant Fc region or variant Cγ2 domain is or is derived from human IgG1, human IgG2, human IgG3 or human IgG4.

28. The protein of claim 26, wherein the variant Fc region or variant Cγ2 domain is or is derived from human IgG1, human IgG2, human IgG3 or human IgG4.

* * * * *

SEQUENCE LISTING

```
Sequence total quantity: 25
SEQ ID NO: 1          moltype = AA  length = 232
FEATURE               Location/Qualifiers
source                1..232
```

```
                        mol_type = protein
                        organism = Homo sapiens
SEQUENCE: 1
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 2            moltype = AA  length = 232
FEATURE                 Location/Qualifiers
REGION                  1..232
                        note = Variant of homo sapiens
source                  1..232
                        mol_type = protein
                        organism = synthetic construct
SEQUENCE: 2
EPKSCDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALGAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 3            moltype = AA  length = 232
FEATURE                 Location/Qualifiers
REGION                  1..232
                        note = Variant of homo sapiens
source                  1..232
                        mol_type = protein
                        organism = synthetic construct
SEQUENCE: 3
EPKSCDKTHT CPPCPAPEAA GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232

SEQ ID NO: 4            moltype = AA  length = 330
FEATURE                 Location/Qualifiers
source                  1..330
                        mol_type = protein
                        organism = Homo sapiens
SEQUENCE: 4
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 5            moltype = AA  length = 107
FEATURE                 Location/Qualifiers
source                  1..107
                        mol_type = protein
                        organism = Homo sapiens
SEQUENCE: 5
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 6            moltype = AA  length = 121
FEATURE                 Location/Qualifiers
source                  1..121
                        mol_type = protein
                        organism = Mus musculus
SEQUENCE: 6
QVQLQQPGAE LVKPGASVKM SCKASGYTFT SYNMHWVKQT PGRGLEWIGA IYPGNGDTSY    60
NQKFKGKATL TADKSSSTAY MQLSSLTSED SAVYYCARST YYGGDWYFNV WGAGTTVTVS   120
S                                                                   121

SEQ ID NO: 7            moltype = AA  length = 106
FEATURE                 Location/Qualifiers
source                  1..106
                        mol_type = protein
                        organism = Mus musculus
SEQUENCE: 7
QIVLSQSPAI LSASPGEKVT MTCRASSSVS YIHWFQQKPG SSPKPWIYAT SNLASGVPVR    60
FSGSGSGTSY SLTISRVEAE DAATYYCQQW TSNPPTFGGG TKLEIK                  106

SEQ ID NO: 8            moltype = AA  length = 119
FEATURE                 Location/Qualifiers
source                  1..119
                        mol_type = protein
```

```
                             organism = Mus musculus
SEQUENCE: 8
QVQLQQSGAE LARPGASVKM SCKASGYTFT RYTMHWVKQR PGQGLEWIGY INPSRGYTNY         60
NQKFKDKATL TTDKSSSTAY MQLSSLTSED SAVYYCARYY DDHYCLDYWG QGTTLTVSS          119

SEQ ID NO: 9                 moltype = AA   length = 106
FEATURE                      Location/Qualifiers
source                       1..106
                             mol_type = protein
                             organism = Mus musculus
SEQUENCE: 9
QIVLTQSPAI MSASPGEKVT MTCSASSSVS YMNWYQQKSG TSPKRWIYDT SKLASGVPAH         60
FRGSGSGTSY SLTISGMEAE DAATYYCQQW SSNPFTFGSG TKLEIK                       106

SEQ ID NO: 10                moltype = AA   length = 121
FEATURE                      Location/Qualifiers
REGION                       1..121
                             note = Humanised antibody
source                       1..121
                             mol_type = protein
                             organism = synthetic construct
SEQUENCE: 10
QVQLQESGPG LVRPSQTLSL TCTVSGFTFT DFYMNWVRQP PGRGLEWIGF IRDKAKGYTT         60
EYNPSVKGRV TMLVDTSKNQ FSLRLSSVTA ADTAVYYCAR EGHTAAPFDY WGQGSLVTVS         120
S                                                                        121

SEQ ID NO: 11                moltype = AA   length = 107
FEATURE                      Location/Qualifiers
REGION                       1..107
                             note = Humanised antibody
source                       1..107
                             mol_type = protein
                             organism = synthetic construct
SEQUENCE: 11
DIQMTQSPSS LSASVGDRVT ITCKASQNID KYLNWYQQKP GKAPKLLIYN TNNLQTGVPS         60
RFSGSGSGTD FTFTISSLQP EDIATYYCLQ HISRPRTFGQ GTKLEIK                      107

SEQ ID NO: 12                moltype = AA   length = 451
FEATURE                      Location/Qualifiers
REGION                       1..451
                             note = Chimeric antibody
source                       1..451
                             mol_type = protein
                             organism = synthetic construct
SEQUENCE: 12
QVQLQQPGAE LVKPGASVKM SCKASGYTFT SYNMHWVKQT PGRGLEWIGA IYPGNGDTSY         60
NQKFKGKATL TADKSSSTAY MQLSSLTSED SAVYYCARST YYGGDWYFNV WGAGTTVTVS         120
SASTKGPSVF PLAPSSKSTS GGTAALGCLV KDYFPEPVTV SWNSGALTSG VHTFPAVLQS         180
SGLYSLSSVV TVPSSSLGTQ TYICNVNHKP SNTKVDKKVE PKSCDKTHTC PPCPAPELLG         240
GPSVFLFPPK PKDTLMISRT PEVTCVVVDV SHEDPEVKFN WYVDGVEVHN AKTKPREEQY         300
NSTYRVVSVL TVLHQDWLNG KEYKCKVSNK ALPAPIEKTI SKAKGQPREP QVYTLPPSRD         360
ELTKNQVSLT CLVKGFYPSD IAVEWESNGQ PENNYKTTPP VLDSDGSFFL YSKLTVDKSR         420
WQQGNVFSCS VMHEALHNHY TQKSLSLSPG K                                       451

SEQ ID NO: 13                moltype = AA   length = 213
FEATURE                      Location/Qualifiers
REGION                       1..213
                             note = Chimeric antibody
source                       1..213
                             mol_type = protein
                             organism = synthetic construct
SEQUENCE: 13
QIVLSQSPAI LSASPGEKVT MTCRASSSVS YIHWFQQKPG SSPKPWIYAT SNLASGVPVR         60
FSGSGSGTSY SLTISRVEAE DAATYYCQQW TSNPPTFGGG TKLEIKRTVA APSVFIFPPS         120
DEQLKSGTAS VVCLLNNFYP REAKVQWKVD NALQSGNSQE SVTEQDSKDS TYSLSSTLTL         180
SKADYEKHKV YACEVTHQGL SSPVTKSFNR GEC                                     213

SEQ ID NO: 14                moltype = AA   length = 449
FEATURE                      Location/Qualifiers
REGION                       1..449
                             note = Chimeric antibody
source                       1..449
                             mol_type = protein
                             organism = synthetic construct
SEQUENCE: 14
QVQLQQSGAE LARPGASVKM SCKASGYTFT RYTMHWVKQR PGQGLEWIGY INPSRGYTNY         60
NQKFKDKATL TTDKSSSTAY MQLSSLTSED SAVYYCARYY DDHYCLDYWG QGTTLTVSSA         120
STKGPSVFPL APSSKSTSGG TAALGCLVKD YFPEPVTVSW NSGALTSGVH TFPAVLQSSG         180
LYSLSSVVTV PSSSLGTQTY ICNVNHKPSN TKVDKKVEPK SCDKTHTCPP CPAPELLGGP         240
```

```
SVFLFPPKPK DTLMISRTPE VTCVVVDVSH EDPEVKFNWY VDGVEVHNAK TKPREEQYNS     300
TYRVVSVLTV LHQDWLNGKE YKCKVSNKAL PAPIEKTISK AKGQPREPQV YTLPPSRDEL     360
TKNQVSLTCL VKGFYPSDIA VEWESNGQPE NNYKTTPPVL DSDGSFFLYS KLTVDKSRWQ     420
QGNVFSCSVM HEALHNHYTQ KSLSLSPGK                                      449

SEQ ID NO: 15           moltype = AA  length = 213
FEATURE                 Location/Qualifiers
REGION                  1..213
                        note = Chimeric antibody
source                  1..213
                        mol_type = protein
                        organism = synthetic construct
SEQUENCE: 15
QIVLTQSPAI MSASPGEKVT MTCSASSSVS YMNWYQQKSG TSPKRWIYDT SKLASGVPAH      60
FRGSGSGTSY SLTISGMEAE DAATYYCQQW SSNPFTFGSG TKLEIKRTVA APSVFIFPPS     120
DEQLKSGTAS VVCLLNNFYP REAKVQWKVD NALQSGNSQE SVTEQDSKDS TYSLSSTLTL     180
SKADYEKHKV YACEVTHQGL SSPVTKSFNR GEC                                  213

SEQ ID NO: 16           moltype = AA  length = 451
FEATURE                 Location/Qualifiers
REGION                  1..451
                        note = Humanised antibody
source                  1..451
                        mol_type = protein
                        organism = synthetic construct
SEQUENCE: 16
QVQLQESGPG LVRPSQTLSL TCTVSGFTFT DFYMNWVRQP PGRGLEWIGF IRDKAKGYTT      60
EYNPSVKGRV TMLVDTSKNQ FSLRLSSVTA ADTAVYYCAR EGHTAAPFDY WGQGSLVTVS     120
SASTKGPSVF PLAPSSKSTS GGTAALGCLV KDYFPEPVTV SWNSGALTSG VHTFPAVLQS     180
SGLYSLSSVV TVPSSSLGTQ TYICNVNHKP SNTKVDKKVE PKSCDKTHTC PPCPAPELLG     240
GPSVFLFPPK PKDTLMISRT PEVTCVVVDV SHEDPEVKFN WYVDGVEVHN AKTKPREEQY     300
NSTYRVVSVL TVLHQDWLNG KEYKCKVSNK ALPAPIEKTI SKAKGQPREP QVYTLPPSRD     360
ELTKNQVSLT CLVKGFYPSD IAVEWESNGQ PENNYKTTPP VLDSDGSFFL YSKLTVDKSR     420
WQQGNVFSCS VMHEALHNHY TQKSLSLSPG K                                   451

SEQ ID NO: 17           moltype = AA  length = 214
FEATURE                 Location/Qualifiers
REGION                  1..214
                        note = Humanised antibody
source                  1..214
                        mol_type = protein
                        organism = synthetic construct
SEQUENCE: 17
DIQMTQSPSS LSASVGDRVT ITCKASQNID KYLNWYQQKP GKAPKLLIYN TNNLQTGVPS      60
RFSGSGSGTD FTFTISSLQP EDIATYYCLQ HISRPRTFGQ GTKLEIKRTV AAPSVFIFPP     120
SDEQLKSGTA SVVCLLNNFY PREAKVQWKV DNALQSGNSQ ESVTEQDSKD STYSLSSTLT     180
LSKADYEKHK VYACEVTHQG LSSPVTKSFN RGEC                                 214

SEQ ID NO: 18           moltype = AA  length = 326
FEATURE                 Location/Qualifiers
source                  1..326
                        mol_type = protein
                        organism = Homo sapiens
SEQUENCE: 18
ASTKGPSVFP LAPCSRSTSE STAALGCLVK DYFPEPVTVS WNSGALTSGV HTFPAVLQSS      60
GLYSLSSVVT VPSSNFGTQT YTCNVDHKPS NTKVDKTVER KCCVECPPCP APPVAGPSVF     120
LFPPKPKDTL MISRTPEVTC VVVDVSHEDP EVQFNWYVDG VEVHNAKTKP REEQFNSTFR     180
VVSVLTVVHQ DWLNGKEYKC KVSNKGLPAP IEKTISKTKG QPREPQVYTL PPSREEMTKN     240
QVSLTCLVKG FYPSDIAVEW ESNGQPENNY KTTPPMLDSD GSFFLYSKLT VDKSRWQQGN     300
VFSCSVMHEA LHNHYTQKSL SLSPGK                                          326

SEQ ID NO: 19           moltype = AA  length = 327
FEATURE                 Location/Qualifiers
source                  1..327
                        mol_type = protein
                        organism = Homo sapiens
SEQUENCE: 19
ASTKGPSVFP LAPCSRSTSE STAALGCLVK DYFPEPVTVS WNSGALTSGV HTFPAVLQSS      60
GLYSLSSVVT VPSSSLGTKT YTCNVDHKPS NTKVDKRVES KYGPPCPSCP APEFLGGPSV     120
FLFPPKPKDT LMISRTPEVT CVVVDVSQED PEVQFNWYVD GVEVHNAKTK PREEQFNSTY     180
RVVSVLTVLH QDWLNGKEYK CKVSNKGLPS SIEKTISKAK GQPREPQVYT LPPSQEEMTK     240
NQVSLTCLVK GFYPSDIAVE WESNGQPENN YKTTPPVLDS DGSFFLYSRL TVDKSRWQEG     300
NVFSCSVMHE ALHNHYTQKS LSLSLGK                                         327

SEQ ID NO: 20           moltype = AA  length = 330
FEATURE                 Location/Qualifiers
source                  1..330
                        mol_type = protein
                        organism = Mus musculus
```

```
SEQUENCE: 20
AKTTAPSVYP  LAPVCGDTTG  SSVTLGCLVK  GYFPEPVTLT  WNSGSLSSGV  HTFPAVLQSD   60
LYTLSSSVTV  TSSTWPSQSI  TCNVAHPASS  TKVDKKIEPR  GPTIKPCPPC  KCPAPNLLGG  120
PSVFIFPPKI  KDVLMISLSP  IVTCVVVDVS  EDDPDVQISW  FVNNVEVHTA  QTQTHREDYN  180
STLRVVSALP  IQHQDWMSGK  EFKCKVNNKD  LPAPIERTIS  KPKGSVRAPQ  VYVLPPPEEE  240
MTKKQVTLTC  MVTDFMPEDI  YVEWTNNGKT  ELNYKNTEPV  LDSDGSYFMY  SKLRVEKKNW  300
VERNSYSCSV  VHEGLHNHHT  TKSFSRTPGK                                      330

SEQ ID NO: 21           moltype = AA  length = 107
FEATURE                 Location/Qualifiers
source                  1..107
                        mol_type = protein
                        organism = Mus musculus
SEQUENCE: 21
RADAAPTVSI  FPPSSEQLTS  GGASVVCFLN  NFYPKDINVK  WKIDGSERQN  GVLNSWTDQD   60
SKDSTYSMSS  TLTLTKDEYE  RHNSYTCEAT  HKTSTSPIVK  SFNRNEC                 107

SEQ ID NO: 22           moltype = AA  length = 333
FEATURE                 Location/Qualifiers
source                  1..333
                        mol_type = protein
                        organism = Rattus norvegicus
SEQUENCE: 22
AQTTAPSVYP  LAPGCGDTTS  STVTLGCLVK  GYFPEPVTVT  WNSGALSSDV  HTFPAVLQSG   60
LYTLTSSVTS  STWPSQTVTC  NVAHPASSTK  VDKKVERRNG  GIGHKCPTCP  TCHKCPVPEL  120
LGGPSVFIFP  PKPKDILLIS  QNAKVTCVVV  DVSEEEPDVQ  FSWFVNNVEV  HTAQTQPREE  180
QYNSTFRVVS  ALPIQHQDWM  SGKEFKCKVN  NKALPSPIEK  TISKPKGLVR  KPQVYVMGPP  240
TEQLTEQTVS  LTCLTSGFLP  NDIGVEWTSN  GHIEKNYKNT  EPVMDSDGSF  FMYSKLNVER  300
SRWDSRAPFV  CSVVHEGLHN  HHVEKSISRP  PGK                                 333

SEQ ID NO: 23           moltype = AA  length = 107
FEATURE                 Location/Qualifiers
source                  1..107
                        mol_type = protein
                        organism = Rattus norvegicus
SEQUENCE: 23
RADAAPTVSI  FPPSTEQLAT  GGASVVCLMN  NFYPRDISVK  WKIDGTERRD  GVLDSVTDQD   60
SKDSTYSMSS  TLSLTKADYE  SHNLYTCEVV  HKTSSSPVVK  SFNRNEC                 107

SEQ ID NO: 24           moltype = AA  length = 323
FEATURE                 Location/Qualifiers
source                  1..323
                        mol_type = protein
                        organism = Oryctolagus cuniculus
SEQUENCE: 24
GQPKAPSVFP  LAPCCGDTPS  STVTLGCLVK  GYLPEPVTVT  WNSGTLTNGV  RTFPSVRQSS   60
GLYSLSSVVS  VTSSSQPVTC  NVAHPATNTK  VDKTVAPSTC  SKPTCPPPEL  LGGPSVFIFP  120
PKPKDTLMIS  RTPEVTCVVV  DVSEDDPEVQ  FTWYINNEQV  RTARPPLREQ  QFNSTIRVVS  180
TLPIAHEDWL  RGKEFKCKVH  NKALPAPIEK  TISKARGQPL  EPKVYTMGPP  REELSSRSVS  240
LTCMINGFYP  SDISVEWEKN  GKAEDNYKTT  PAVLDSDGSY  FLYSKLSVPT  SEWQRGDVFT  300
CSVMHEALHN  HYTQKSISRS  PGK                                             323

SEQ ID NO: 25           moltype = AA  length = 106
FEATURE                 Location/Qualifiers
source                  1..106
                        mol_type = protein
                        organism = Oryctolagus cuniculus
SEQUENCE: 25
RDPVAPSVLL  FPPSKEELTT  GTATIVCVAN  KFYPSDITVT  WKVDGTTQQS  GIENSKTPQS   60
PEDNTYSLSS  TLSLTSAQYN  SHSVYTCEVV  QGSASPIVQS  FNRGDC                  106
```

UNITED STATES PATENT AND TRADEMARK OFFICE
CERTIFICATE OF CORRECTION

| | | |
|---|---|---|
| PATENT NO. | : 12,037,380 B2 | Page 1 of 1 |
| APPLICATION NO. | : 18/057420 | |
| DATED | : July 16, 2024 | |
| INVENTOR(S) | : Geoffrey Hale et al. | |

It is certified that error appears in the above-identified patent and that said Letters Patent is hereby corrected as shown below:

In the Specification

Column 1, Line 8 CROSS-REFERENCE TO RELATED APPLICATIONS paragraph:
Delete "PCT/GB2021/051223" and replace with PCT/GB2021/051233

Signed and Sealed this
Ninth Day of December, 2025

John A. Squires
*Director of the United States Patent and Trademark Office*